(12) United States Patent
Hatakeyama et al.

(10) Patent No.: US 10,844,257 B2
(45) Date of Patent: *Nov. 24, 2020

(54) ADHESIVE COMPOSITION, BIO-ELECTRODE, AND METHOD FOR MANUFACTURING A BIO-ELECTRODE

(71) Applicant: SHIN-ETSU CHEMICAL Co., LTD., Tokyo (JP)

(72) Inventors: Jun Hatakeyama, Jyoetsu (JP); Motoaki Iwabuchi, Jyoetsu (JP); Masaki Ohashi, Jyoetsu (JP); Yasuyoshi Kuroda, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 647 days.

This patent is subject to a terminal disclaimer.

(21) Appl. No.: 15/683,914

(22) Filed: Aug. 23, 2017

(65) Prior Publication Data

US 2018/0072930 A1    Mar. 15, 2018

(30) Foreign Application Priority Data

Sep. 13, 2016   (JP) ................................. 2016-178937

(51) Int. Cl.
*C09J 9/02*         (2006.01)
*C09J 183/04*    (2006.01)
(Continued)

(52) U.S. Cl.
CPC ......... *C09J 183/04* (2013.01); *A61B 5/04087* (2013.01); *A61B 5/6832* (2013.01);
(Continued)

(58) Field of Classification Search
CPC ..... C09J 9/02; C09J 11/04; C09J 11/06; C09J 133/04; C09J 175/04; C09J 183/04;
(Continued)

(56) References Cited

U.S. PATENT DOCUMENTS 4,777,954 A  * 10/1988  Keusch ............... A61B 5/0408
                                                         600/392
5,981,680 A      11/1999  Petroff et al.
(Continued)

FOREIGN PATENT DOCUMENTS

| JP | H05-095924 A | 4/1993 |
| JP | H10-158457 A | 6/1998 |

(Continued)

OTHER PUBLICATIONS

Jan. 8, 2019 Office Action issued in Korean Patent Application No. 10-2017-0115718.
(Continued)

*Primary Examiner* — Eun Hwa Kim
*Assistant Examiner* — Adam Z Minchella
(74) *Attorney, Agent, or Firm* — Oliff PLC

(57) ABSTRACT

An adhesive composition including resin and electro-conductive material, wherein the electro-conductive material is one or more salts from sodium salt, potassium salt, and calcium salt of fluorosulfonic acid having 5 or more carbon atoms shown by the general formula (1): $(R^1—X—Y—SO_3^-)_n M^{n+}$ (1), wherein, $R^1$ represents a monovalent hydrocarbon group having 1-30 carbon atoms and optionally substituted by a heteroatom or optionally interposed by a heteroatom; X represents any of a single bond, ether group, ester group, and amide group; Y represents a linear or branched alkylene group having 2-4 carbon atoms, containing 1-6 fluorine atoms, and optionally containing a carbonyl group; $M^{n+}$ represents any of a sodium ion, potassium ion, and calcium ion. This can form a living body contact layer for a bio-electrode with electric conductivity, biocompatibility, and light weight, which can be manufactured at low cost and without electric conductivity large lowering even when wetted with water or dried.

20 Claims, 2 Drawing Sheets

(51) Int. Cl.
| | |
|---|---|
| *A61L 15/24* | (2006.01) |
| *C09J 183/08* | (2006.01) |
| *A61L 15/58* | (2006.01) |
| *A61L 15/26* | (2006.01) |
| *A61B 5/0408* | (2006.01) |
| *A61B 5/00* | (2006.01) |
| *H01B 1/02* | (2006.01) |
| *H01B 13/06* | (2006.01) |
| *C08G 77/26* | (2006.01) |
| *C08G 77/28* | (2006.01) |
| *C08G 77/20* | (2006.01) |

(52) U.S. Cl.
CPC ............ *A61L 15/24* (2013.01); *A61L 15/26* (2013.01); *A61L 15/58* (2013.01); *C09J 183/08* (2013.01); *H01B 1/023* (2013.01); *H01B 1/026* (2013.01); *H01B 13/06* (2013.01); *A61L 2400/12* (2013.01); *C08G 77/20* (2013.01); *C08G 77/26* (2013.01); *C08G 77/28* (2013.01)

(58) Field of Classification Search
CPC .... C09J 183/08; A61B 5/0245; A61B 5/0408; A61B 5/0531; A61B 5/6832; A61B 5/0478; A61B 5/0492; A61B 2562/0209; A61B 2562/14; C07C 211/63; C07C 215/12; C07C 217/28; C07C 219/06; C07C 309/12; C07C 309/17; C07C 309/19; C07C 309/24; C07C 311/48; C07C 2603/74; C07C 2601/14; C07D 211/06; C07J 31/006; C08F 290/068; C08F 299/065; C08F 299/08; C08G 18/4833; C08G 18/61; C08G 18/755; C08G 18/8116; C08G 77/12; C08G 77/20; C08K 3/04; C08K 5/42

See application file for complete search history.

(56) References Cited

U.S. PATENT DOCUMENTS

| | | | |
|---|---|---|---|
| 2002/0009650 A1* | 1/2002 | Michot | ................ B01J 31/0215 |
| | | | 429/314 |
| 2002/0188069 A1 | 12/2002 | Sugo et al. | |
| 2008/0032231 A1 | 2/2008 | Hatakeyama et al. | |
| 2008/0118860 A1 | 5/2008 | Harada et al. | |
| 2009/0061358 A1 | 3/2009 | Ohashi et al. | |
| 2010/0119970 A1 | 5/2010 | Ohsawa et al. | |
| 2015/0275060 A1 | 10/2015 | Kuroda et al. | |
| 2016/0155530 A1* | 6/2016 | Someya | ................. A61B 5/686 |
| | | | 174/257 |

FOREIGN PATENT DOCUMENTS

| | | |
|---|---|---|
| JP | 2002-332305 A | 11/2002 |
| JP | 2002-356661 A | 12/2002 |
| JP | 2003-225217 A | 8/2003 |
| JP | 2003-272695 A | 9/2003 |
| JP | 2004-033468 A | 2/2004 |
| JP | 2005-320418 A | 11/2005 |
| JP | 2008-039815 A | 2/2008 |
| JP | 2008-111103 A | 5/2008 |
| JP | 2009-080474 A | 4/2009 |
| JP | 2010-113209 A | 5/2010 |
| JP | 2011-079946 A | 4/2011 |
| JP | 2015-019806 A | 2/2015 |
| JP | 2015-100673 A | 6/2015 |
| JP | 2015-193803 A | 11/2015 |
| JP | 2016-011338 A | 1/2016 |
| JP | 2016-065238 A | 4/2016 |
| WO | 2013/039151 A1 | 3/2013 |

OTHER PUBLICATIONS

Apr. 7, 2020 Office Action issued in Japanese Patent Application No. 2017-152270.

* cited by examiner

ADHESIVE COMPOSITION, BIO-ELECTRODE, AND METHOD FOR MANUFACTURING A BIO-ELECTRODE

TECHNICAL FIELD

The present invention relates to a bio-electrode, which is in contact with living skin and can detect physical conditions such as a heart rate on the basis of electric signals from the skin, and a method for manufacturing the same, as well as an adhesive composition that can be suitably used for a bio-electrode.

BACKGROUND ART

In recent years, wearable devices have been developed progressively with the spread of Internet of Things (IoT). Representative examples thereof include a watch and glasses that can be connected with internet. Wearable devices that can always monitor physical conditions are also necessary in a medical field and a sports field, and are expected to be a growth field in the future.

In the medical field, wearable devices have been investigated to monitor organic conditions by sensing a weak current such as an electrocardiogram measurement, which detects heart beats by electric signals. The electrocardiogram is measured by fitting a body with electrodes on which electro-conductive paste is applied, and this measurement is performed only once in a short period of time. On the other hand, the aim of development of the foregoing medical wearable device is to develop devices that monitor health conditions continuously for several weeks. Accordingly, bio-electrodes used for a medical wearable device have to keep the electric conductivity unchanged and not to cause skin allergies even when being used for a long time. In addition to these, it is desirable that the bio-electrode is light in weight and can be manufactured at low cost.

Medical wearable devices include a type in which the device is attached to a body and a type in which the device is incorporated into clothes. As the type in which the device is attached to a body, it has been proposed a bio-electrode using water soluble gel containing water and electrolyte, which are materials of the foregoing electro-conductive paste (Patent Document 1). The water soluble gel contains sodium, potassium, or calcium as the electrolyte in a water soluble polymer for retaining water, and converts changes of ion concentration from skin into electricity. On the other hand, as the type in which the device is incorporated into clothes, it has been proposed a means to use cloth in which an electro-conductive polymer such as poly-3,4-ethylenedioxythiophene-polystyrenesulfonate (PEDOT-PSS) or silver paste is incorporated into the fibers for electrodes (Patent Document 2).

When using the foregoing water soluble gel containing water and electrolyte, however, the electric conductivity is lost as the water is lost due to drying. On the other hand, some people can cause skin allergies by the use of metal with high ionization tendency such as copper. The use of an electro-conductive polymer such as PEDOT-PSS also has a risk of skin allergies due to the strong acidity of the electro-conductive polymer.

As the electrode material, it has been investigated to use metal nanowire, carbon black, and carbon nanotube since they have excellent electric conductivity (Patent Documents 3, 4, and 5). The metal nanowire can conduct electricity in a small loading amount since the wires are brought into contact with each other in high probability. The metal nanowire, however, can cause skin allergies since they are thin material with sharp tips. The carbon nanotube also has stimuli to a living body by the same reason. The carbon black has some irritativeness to skin, although the toxicity is lower than the carbon nanotube. As described above, the biocompatibility is sometimes worsened due to the shape and irritativeness of a material, even though the material itself does not cause an allergic reaction. Accordingly, it has been difficult to achieve both the electric conductivity and the biocompatibility.

As a means for solving these problems, it has been investigated to use electro-conductive metal particles as an electrode material. Among metals, noble metals such as gold, platinum, and silver, which have lowest ionization tendencies, are hard to cause skin allergies. Accordingly, it is possible to achieve both the electric conductivity and the biocompatibility by using these noble metal particles. When mixing these noble metal particles into a resin, however, electricity is not conducted unless the particles are brought into contact with each other in the resin, which is an insulator. In order to bring the particles into contact with each other, the noble metal particles have to be loaded in a volume ratio of 70% or more. As described above, when using metal particles, it is necessary to load a large amount of expensive noble metal particles, and accordingly, the production cost becomes very high and the weight increases, thereby making it impossible to achieve weight reduction, which is necessary for wearable devices.

When the bio-electrode is away from skin, it becomes impossible to obtain information from the body. Just the change of contact area fluctuates the quantity of electricity to be conducted, thereby fluctuating the baseline of an electrocardiogram (electric signals). Accordingly, the bio-electrode have to be in contact with skin continually without changing the contact area in order to obtain stable electric signals from a body. For that purpose, the bio-electrode preferably has tackiness. It also needs elasticity and flexibility to cope with expansion and contraction as well as change of bending of skin.

PRIOR ART DOCUMENTS

Patent Documents

Patent Document 1: International Patent Laid-Open Publication No. WO 2013/039151
Patent Document 2: Japanese Unexamined Patent Application (Kokai) No. 2015-100673
Patent Document 3: Japanese Unexamined Patent Application Publication (Kokai) No. H5-095924
Patent Document 4: Japanese Unexamined Patent Application Publication (Kokai) No. 2003-225217
Patent Document 5: Japanese Unexamined Patent Application Publication (Kokai) No. 2015-019806

SUMMARY OF INVENTION

Technical Problem

The present invention has been accomplished to solve the foregoing problems, and an object thereof is to provide an adhesive composition that can form a living body contact layer for a bio-electrode with excellent electric conductivity and biocompatibility as well as light weight, which can be manufactured at low cost and does not cause large lowering of the electric conductivity even when it is wetted with water or dried; a bio-electrode in which the living body contact layer is formed from the adhesive composition; and a method for manufacturing the same.

Solution to Problem

To achieve the object, the present invention provides an adhesive composition comprising a resin and an electro-conductive material, wherein the electro-conductive material is one or more salts selected from the group consisting of sodium salt, potassium salt, and calcium salt of fluorosulfonic acid having 5 or more carbon atoms shown by the following general formula (1), $$(R^1\text{—}X\text{—}Y\text{—}SO_3^-)_n\,M^{n+} \tag{1}$$

wherein, $R^1$ represents a linear, branched, or cyclic monovalent hydrocarbon group having 1 to 30 carbon atoms and optionally substituted by a heteroatom or optionally interposed by a heteroatom; X represents any of a single bond, an ether group, an ester group, and an amide group; Y represents a linear or branched alkylene group having 2 to 4 carbon atoms, containing 1 to 6 fluorine atoms, and optionally containing a carbonyl group; $M^{n+}$ represents any of a sodium ion, a potassium ion, and a calcium ion; and "n" is 1 when $M^{n+}$ is a sodium ion or a potassium ion, or is 2 when $M^{n+}$ is a calcium ion.

Such an adhesive composition can be an adhesive composition that can form a living body contact layer for a bio-electrode with excellent electric conductivity and biocompatibility as well as light weight, which can be manufactured at low cost and does not cause large lowering of the electric conductivity even when it is wetted with water or dried.

It is preferable that the electro-conductive material be shown by the following general formula (1-1), (1-2), or (1-3),

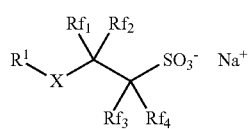

(1-1)

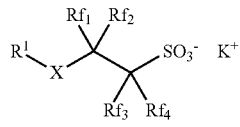

(1-2)

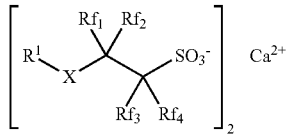

(1-3)

wherein, $R^1$ and X have the same meanings as defined above; $Rf_1$ to $Rf_4$ each independently represent an atom or a group selected from a hydrogen atom, a fluorine atom, a methyl group, an ethyl group, and a trifluoromethyl group, with the proviso that one or more of $Rf_1$ to $Rf_4$ is a fluorine atom or a trifluoromethyl group, and $Rf_1$ and $Rf_2$ are optionally combined with each other to form a carbonyl group.

The bio-electrode, containing such an electro-conductive material, is more superior in electric conductivity and biocompatibility, and causes less lowering of the electric conductivity when it is wetted with water or dried.

It is preferable that the electro-conductive material have a polymerizable double bond or a hydroxy group in the anion.

The bio-electrode, containing such an electro-conductive material, causes less lowering of the electric conductivity when it is wetted with water or dried because the electro-conductive material reacts with the resin and binds thereto when the adhesive composition is cured.

It is preferable that the resin be one or more resins selected from silicone resin, acrylic resin, and urethane resin.

The adhesive composition that contains such resin can form a living body contact layer that is excellent in compatibility with the electro-conductive material, adhesion properties to the electro-conductive material, tackiness to skin, elasticity, and repellency, in particular.

It is preferable that the adhesive composition further comprise a carbon material.

Such an adhesive composition containing a carbon material can form a living body contact layer that has more favorable electric conductivity.

It is preferable that the carbon material be either or both of carbon black and carbon nanotube.

Such a carbon material can be particularly preferably used in the inventive adhesive composition.

The present invention also provides a bio-electrode comprising an electro-conductive base material and a living body contact layer formed on the electro-conductive base material, wherein the living body contact layer is a cured material of the foregoing adhesive composition.

Such a bio-electrode can be a bio-electrode having a living body contact layer with excellent electric conductivity and biocompatibility as well as light weight, which can be manufactured at low cost and does not cause large lowering of the electric conductivity even when it is wetted with water or dried.

It is preferable that the electro-conductive base material comprises one or more species selected from gold, silver, silver chloride, platinum, aluminum, magnesium, tin, tungsten, iron, copper, nickel, stainless steel, chromium, titanium, and carbon.

Such an electro-conductive base material can be particularly preferably used in the inventive bio-electrode.

The present invention also provides a method for manufacturing a bio-electrode having an electro-conductive base material and a living body contact layer formed on the electro-conductive base material, comprising: applying the foregoing adhesive composition onto the electro-conductive base material; and curing the adhesive composition; thereby forming the living body contact layer.

Such a production method makes it possible to manufacture a bio-electrode having a living body contact layer easily and at low cost, which is excellent in electric conductivity and biocompatibility as well as light in weight without causing large lowering of the electric conductivity even when it is wetted with water or dried.

It is preferable that the electro-conductive base material comprise one or more species selected from gold, silver, silver chloride, platinum, aluminum, magnesium, tin, tungsten, iron, copper, nickel, stainless steel, chromium, titanium, and carbon.

Such an electro-conductive base material can be particularly preferably used in the inventive method for manufacturing a bio-electrode.

Advantageous Effects of Invention

As described above, the inventive adhesive composition can form a living body contact layer for a bio-electrode that can efficiently conduct electric signals from skin to a device (i.e., having excellent electric conductivity), is free from the risk of causing allergies even when it is worn on skin for a long time (i.e., having excellent biocompatibility is light in weight, can be manufactured at low cost, and does not cause large lowering of the electric conductivity even when it is wetted with water or dried. The elasticity and tackiness to skin can be improved by additives, and can be adjusted by adjusting the composition of the resin and the thickness of the living body contact layer appropriately. Accordingly, the inventive bio-electrode, with the living body contact layer being formed by using such an inventive adhesive composition, is particularly suitable as a bio-electrode used for a medical wearable device. Moreover, the inventive method for manufacturing a bio-electrode can manufacture such a bio-electrode easily at low cost.

DESCRIPTION OF EMBODIMENTS

Figure 1:
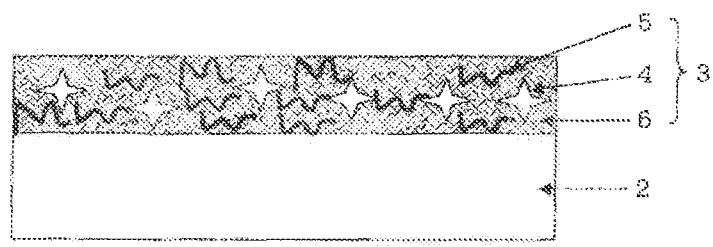
FIG. 1 is a schematic sectional view showing an example of the inventive bio-electrode.

As described above, it has been desired to develop an adhesive composition that can form a living body contact layer for a bio-electrode with excellent electric conductivity and biocompatibility as well as light weight, which can be manufactured at low cost and does not cause large lowering of the electric conductivity even when it is wetted with water or dried; a bio-electrode in which the living body contact layer is formed from the adhesive composition; and a method for manufacturing the same.

The present inventors noticed alkali metal salt and alkaline earth metal salt such as sodium salt, potassium salt, and calcium salt as an electro-conductive material to be blended to an adhesive composition for forming a living body contact layer for a bio-electrode. However, these salts are generally liable to hydrate, thereby causing a bio-electrode to lower the electric conductivity due to extraction of the salt with perspiration or by washing when these salts are added to an adhesive composition to form the living body contact layer.

The present inventors have diligently investigated to solve the foregoing subject and have consequently found that sodium salt, potassium salt, and calcium salt of fluorosulfonic acid having 5 or more carbon atoms and containing 1 to 6 fluorine atoms in a particular moiety have very low solubility in water, thereby considerably decreasing the risk of causing rough dry skin and lowering of the electric conductivity due to extraction with perspiration. The present inventors also have found that these salts, being mixed into an adhesive mass (resin such as silicone type, acrylic type, and urethane type) to form a living body contact layer, enable a bio-electrode to cope with both electric conductivity and biocompatibility without causing large lowering of the electric conductivity even when it is wetted with water or dried, and to function as a bio-electrode that can be in contact with skin continually to obtain stable electric signals from a body in a long period; thereby completing the present invention.

That is, the present invention is an adhesive composition comprising a resin and an electro-conductive material, wherein the electro-conductive material is one or more salts selected from the group consisting of sodium salt, potassium salt, and calcium salt of fluorosulfonic acid having 5 or more carbon atoms shown by the following general formula (1), $$(R^1-X-Y-SO_3^-)_n M^{n+} \quad (1)$$

wherein, $R^1$ represents a linear, branched, or cyclic monovalent hydrocarbon group having 1 to 30 carbon atoms and optionally substituted by a heteroatom or optionally interposed by a heteroatom; X represents any of a single bond, an ether group, an ester group, and an amide group; Y represents a linear or branched alkylene group having 2 to 4 carbon atoms, containing 1 to 6 fluorine atoms, and optionally containing a carbonyl group; $M^{n+}$ represents any of a sodium ion, a potassium ion, and a calcium ion; and "n" is 1 when $M^{n+}$ is a sodium ion or a potassium ion, or is 2 when $M^{n+}$ is a calcium ion.

Hereinafter, the present invention will be specifically described, but the present invention is not limited thereto.

<Adhesive Composition>

The inventive adhesive composition contains an electro-conductive material and resin. Hereinafter, each component will be described further specifically.

[Electro-Conductive Material (Salt)]

The salt to be blended as an electro-conductive material to the inventive adhesive composition is one or more salts selected from the sodium salt, potassium salt, and calcium salt of fluorosulfonic acid having 5 or more carbon atoms shown by the following general formula (1), $$(R^1-X-Y-SO_3^-)_n M^{n+} \quad (1)$$

wherein, $R^1$ represents a linear, branched, or cyclic monovalent hydrocarbon group having 1 to 30 carbon atoms and optionally substituted by a heteroatom or optionally interposed by a heteroatom; X represents any of a single bond, an ether group, an ester group, and an amide group; Y represents a linear or branched alkylene group having 2 to 4 carbon atoms, containing 1 to 6 fluorine atoms, and optionally containing a carbonyl group; $M^{n+}$ represents any of a sodium ion, a potassium ion, and a calcium ion; and "n" is 1 when $M^{n+}$ is a sodium ion or a potassium ion, or is 2 when $M^{n+}$ is a calcium ion.

The salt to be blended as an electro-conductive material to the inventive adhesive composition is preferably a salt shown by the following general formula (1-1), (1-2), or (1-3),

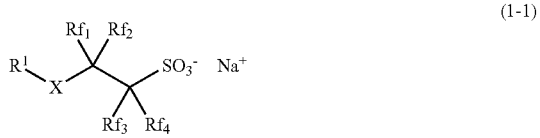

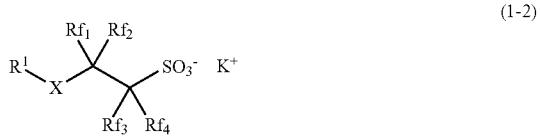

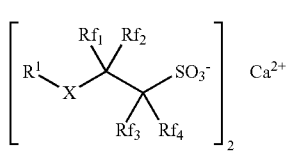

(1-3)

wherein, $R^1$ and X have the same meanings as defined above; $Rf_1$ to $Rf_4$ each independently represent an atom or a group selected from a hydrogen atom, a fluorine atom, a methyl group, an ethyl group, and a trifluoromethyl group, with the proviso that one or more of $Rf_1$ to $Rf_4$ is a fluorine atom or a trifluoromethyl group, and $Rf_1$ and $Rf_2$ are optionally combined with each other to form a carbonyl group.

$R^1$ represents a linear, branched, or cyclic monovalent hydrocarbon group having 1 to 30 carbon atoms and optionally substituted by a heteroatom or optionally interposed by a heteroatom. Illustrative examples of $R_1$ include an alkyl group, an alkenyl group, an alkynyl group having 1 to 30, preferably 3 to 30 carbon groups, an aryl group, an aralkyl group, and a heteroaromatic group having 4 to 16, preferably 6 to 12 carbon atoms; which may have a halogen atom, a silicon atom, a sulfur atom, a nitrogen atom, a hydroxy group, a carboxy group, a carbonyl group, an ether group, a thiol group, an ester group, a carbonate group, an amide group, an urethane group, an amino group, an alkoxycarbonyl-substituted amino group, a sultone group, a lactam group, a sulfoneamide group, an azide group, a sulfonyl group, a sulfonyloxy group, a cyano group, and/or a nitro group.

Illustrative examples of the fluorosulfonate anion of the salt shown by the foregoing general formula (1-1), (1-2), or (1-3) include the following.

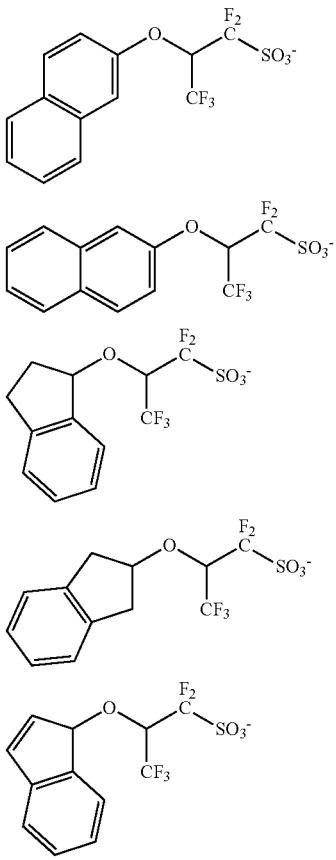

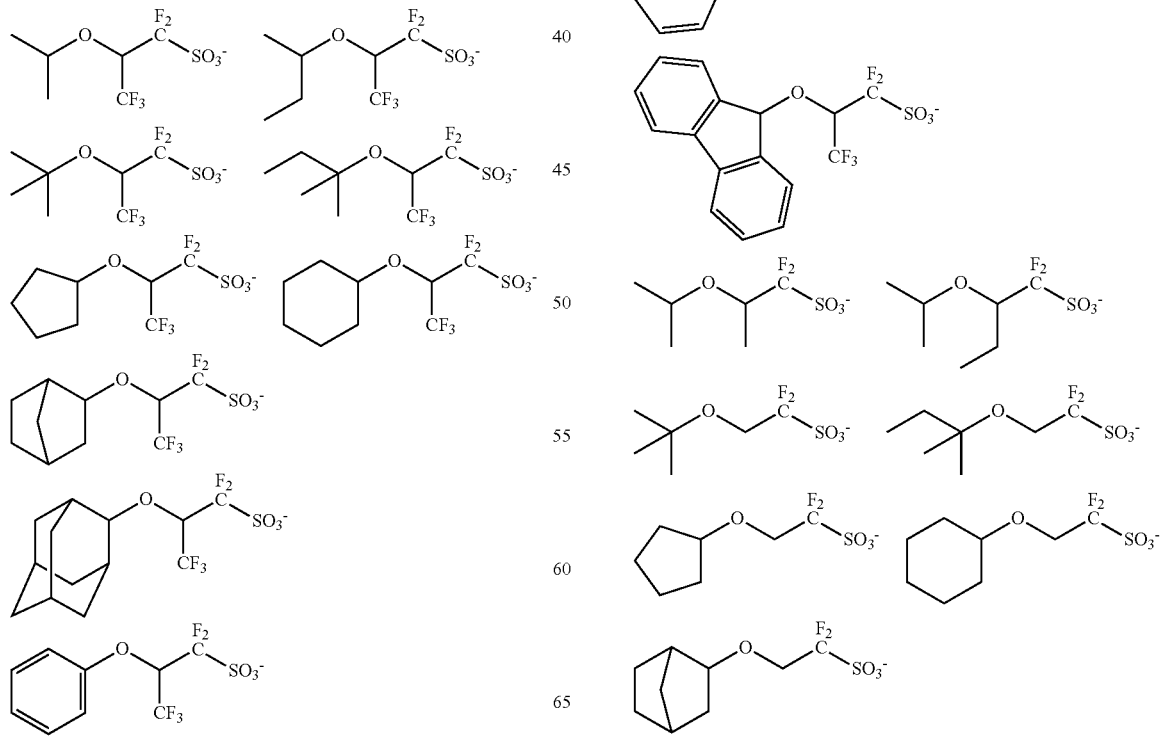

-continued
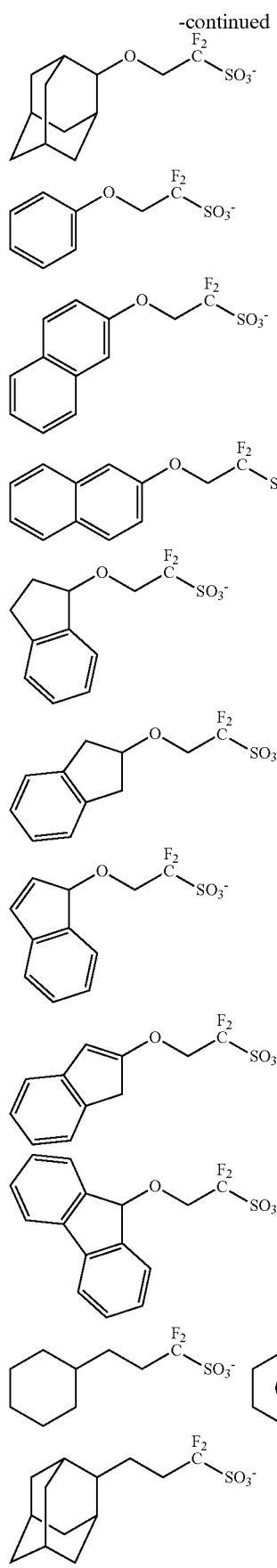
-continued
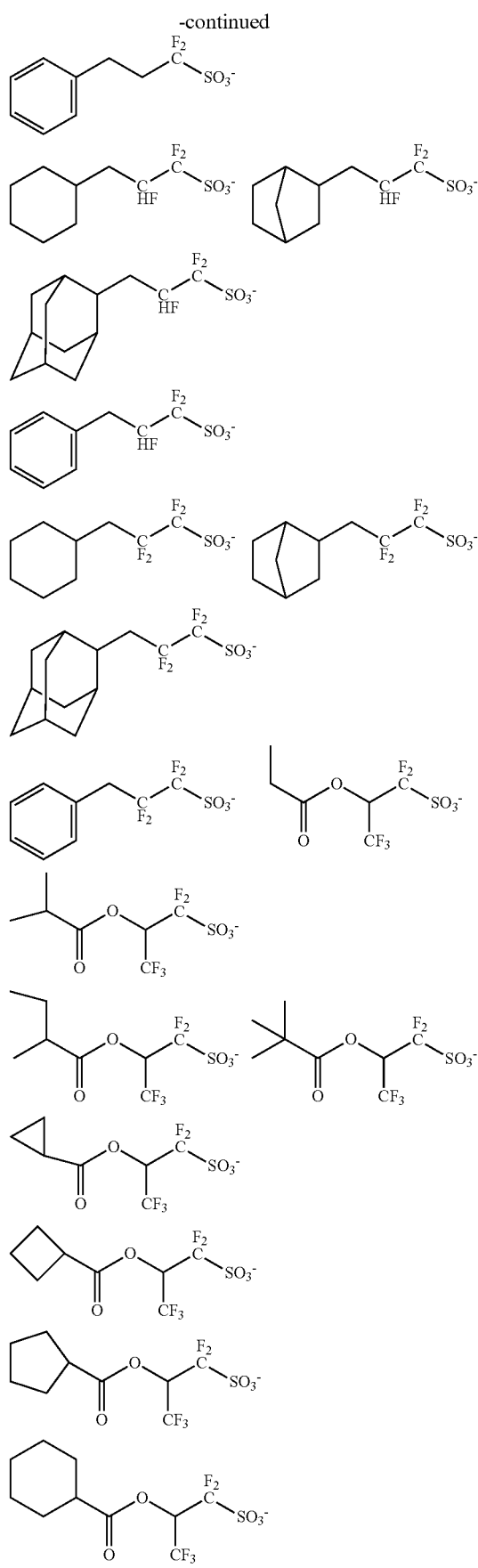

-continued
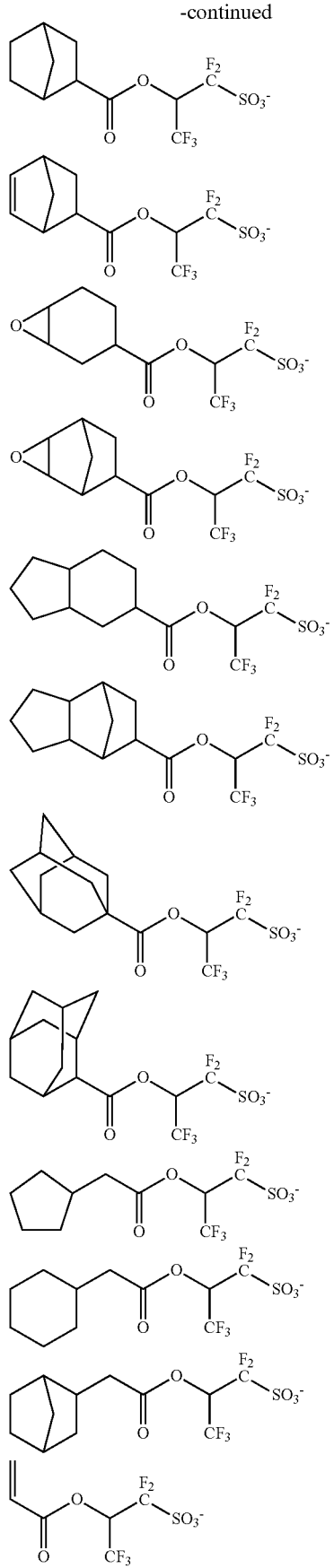
-continued
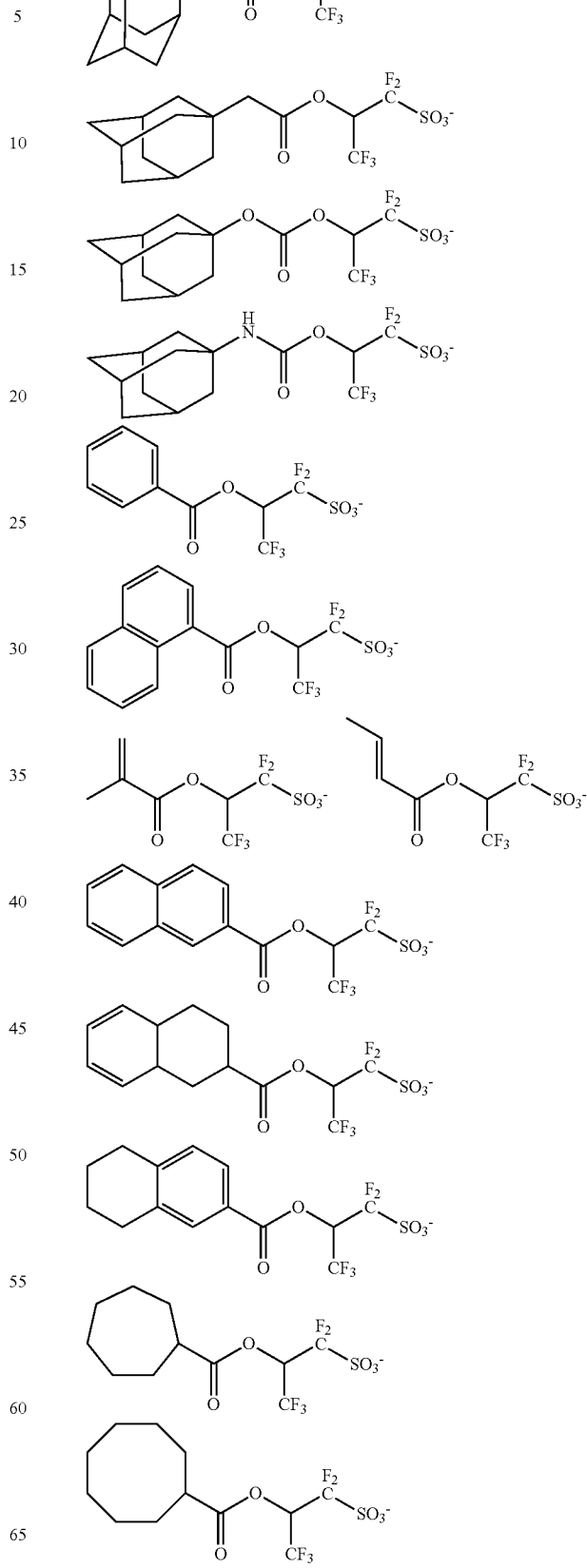

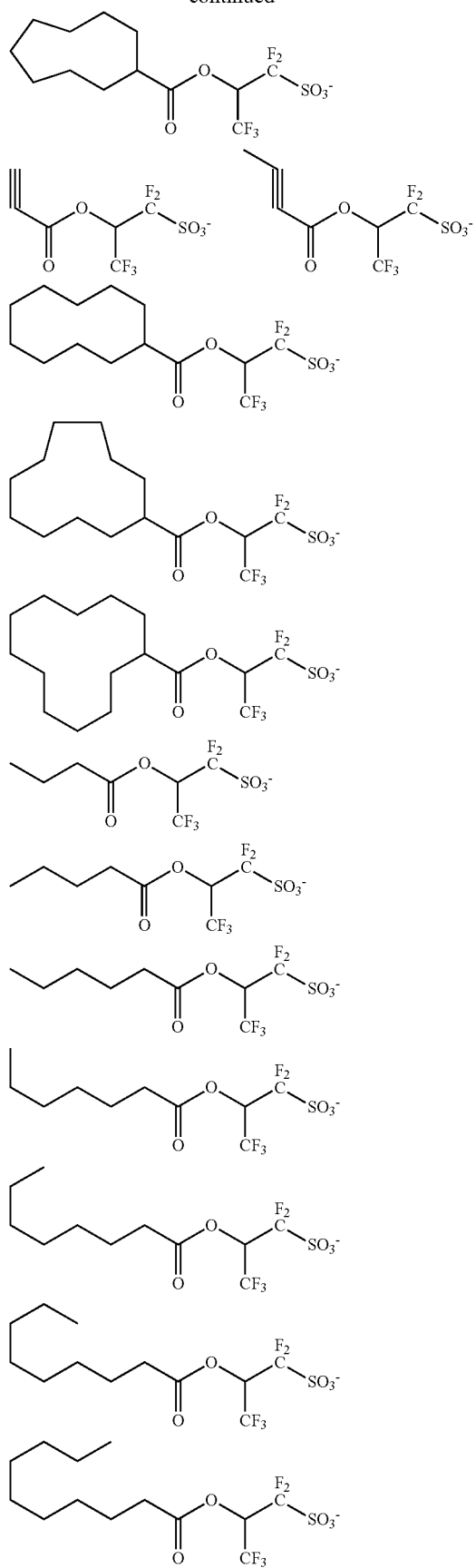
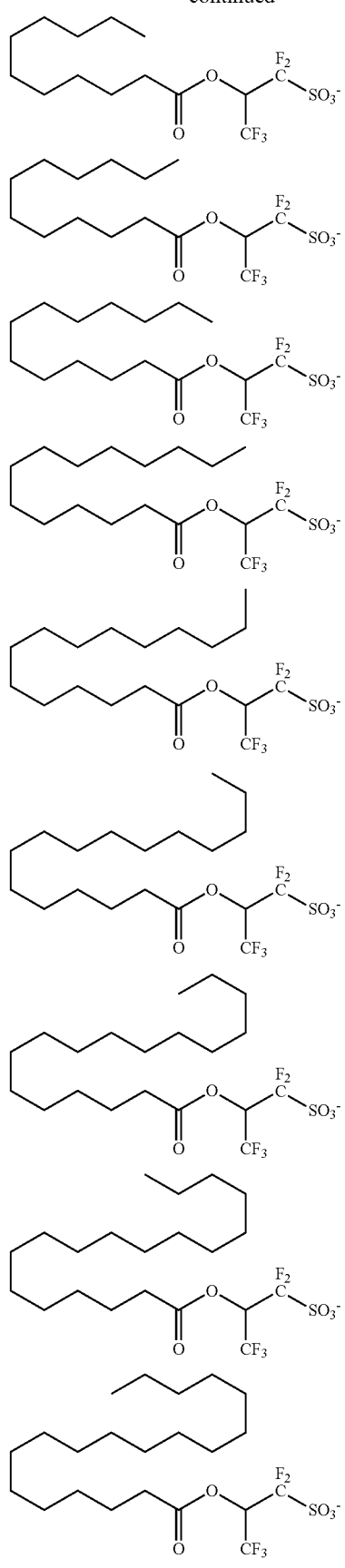

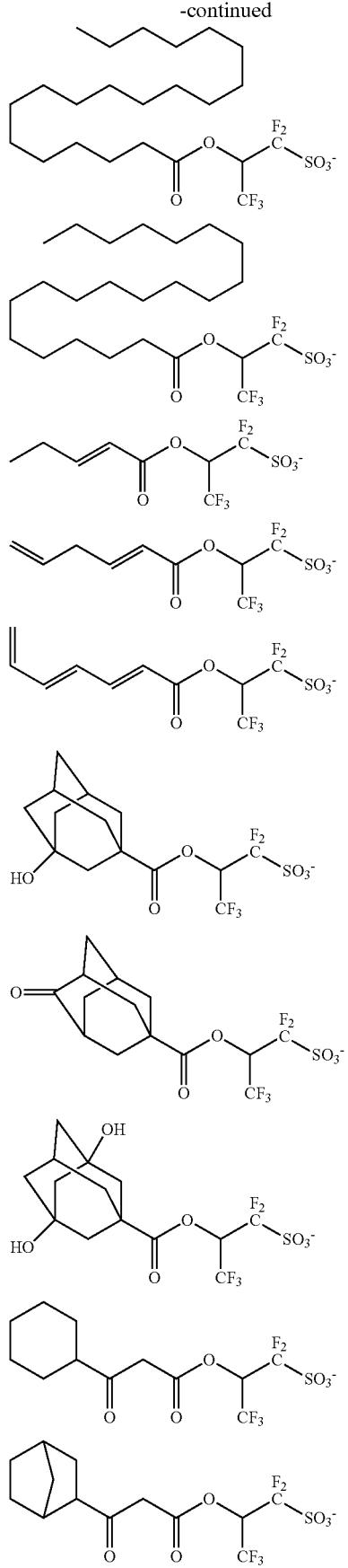
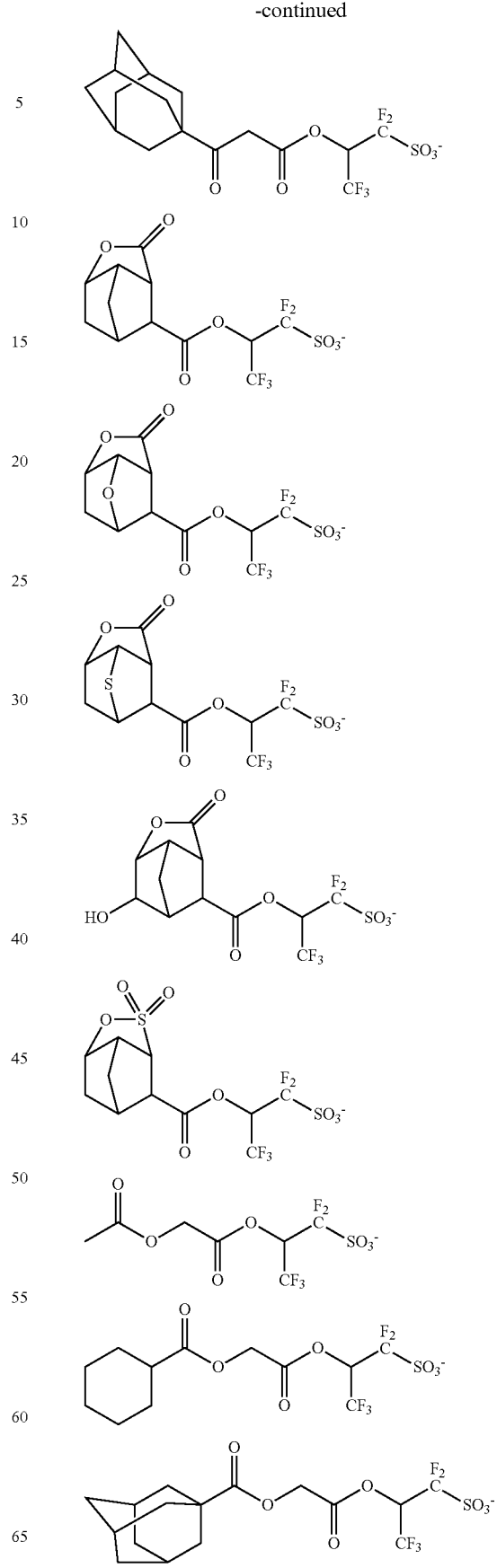

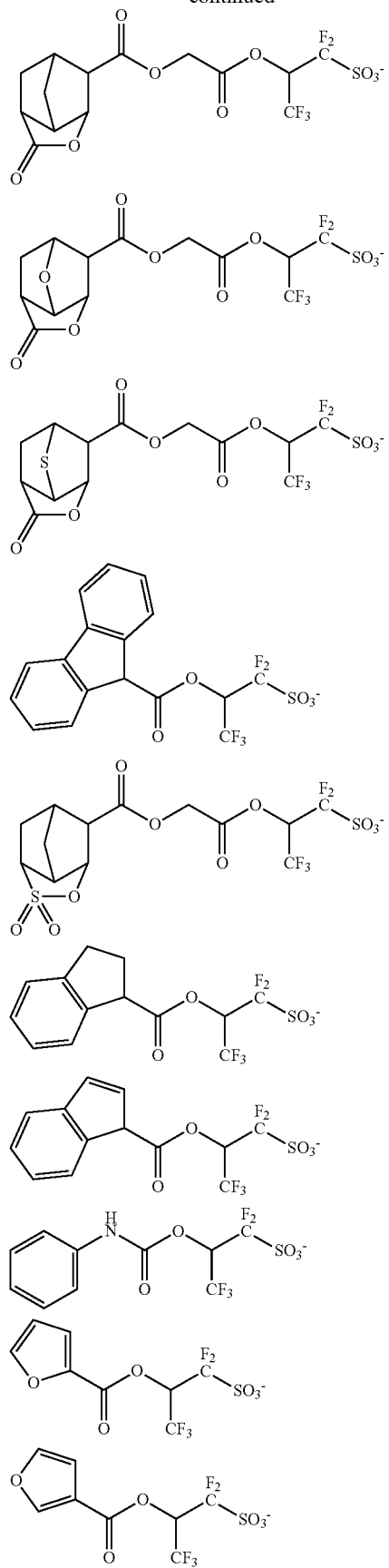
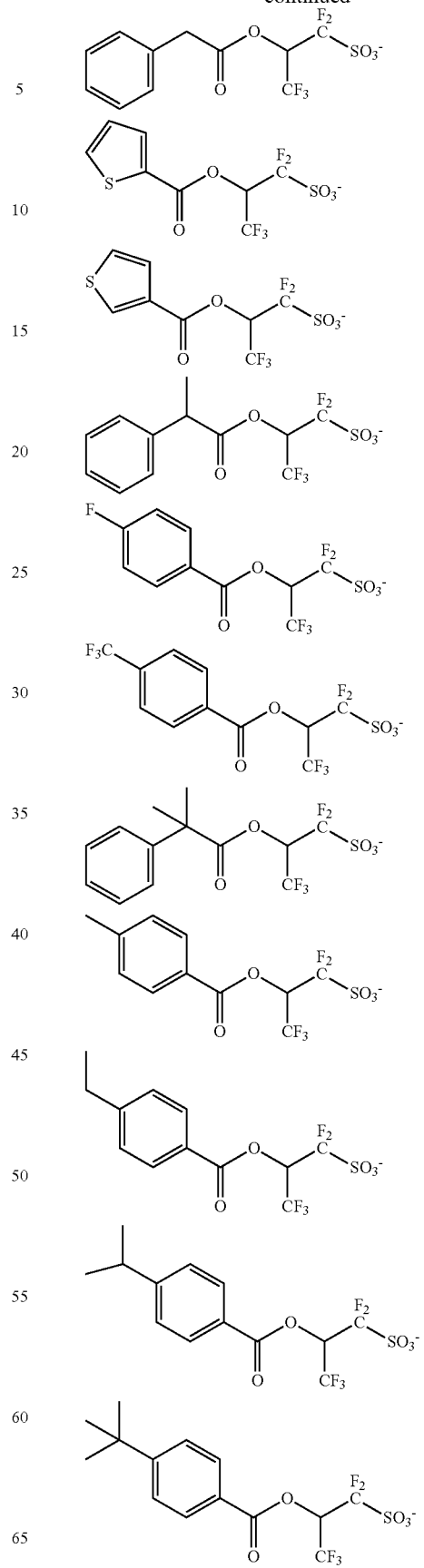

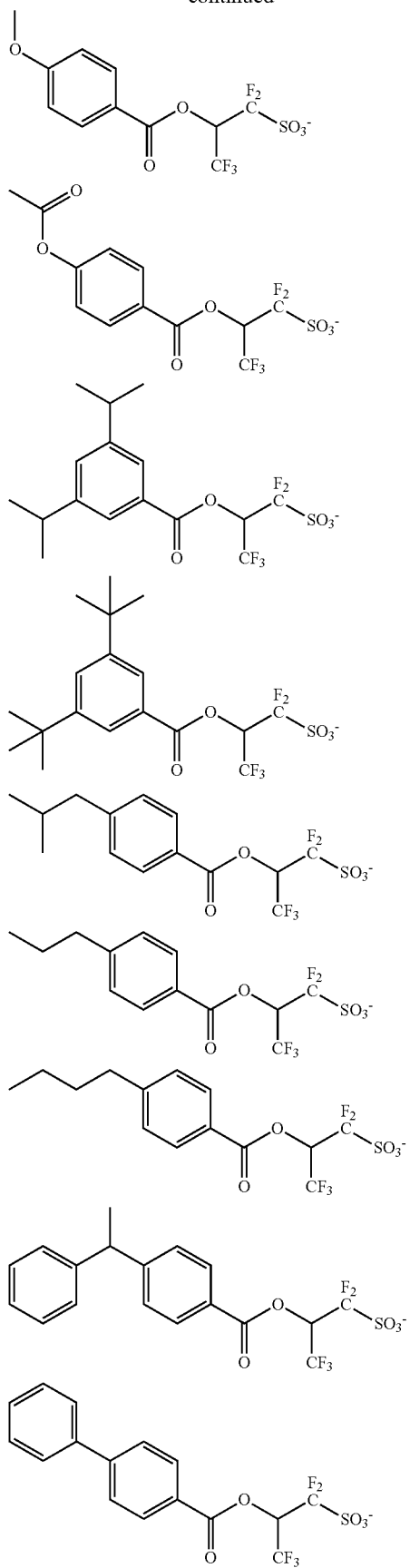
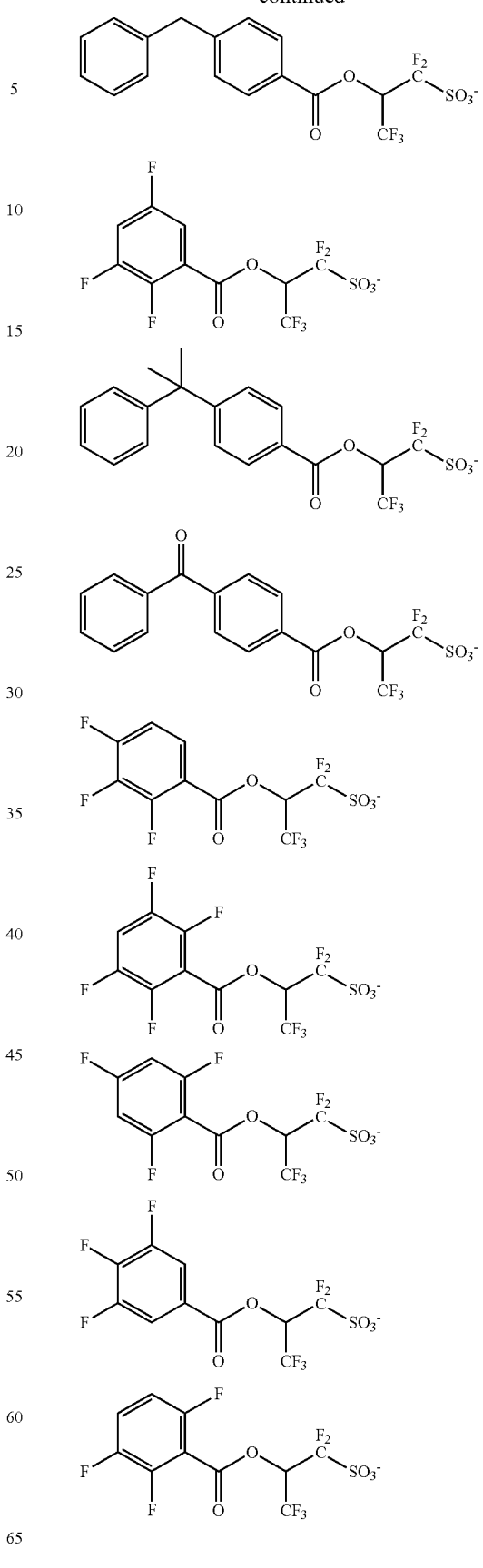

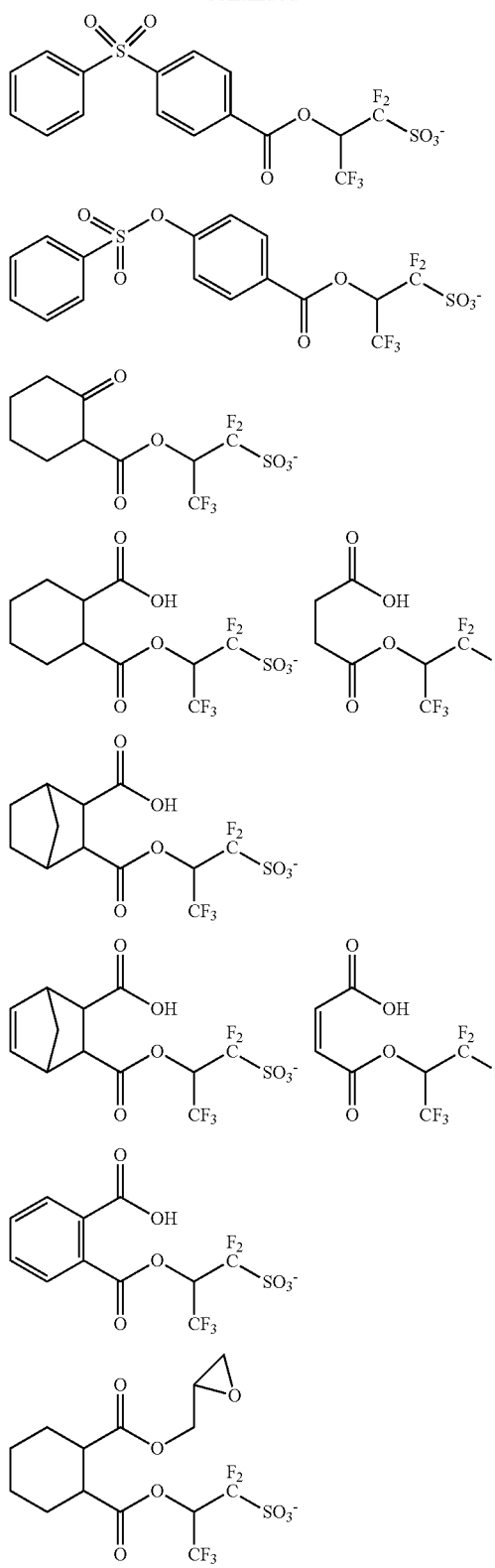
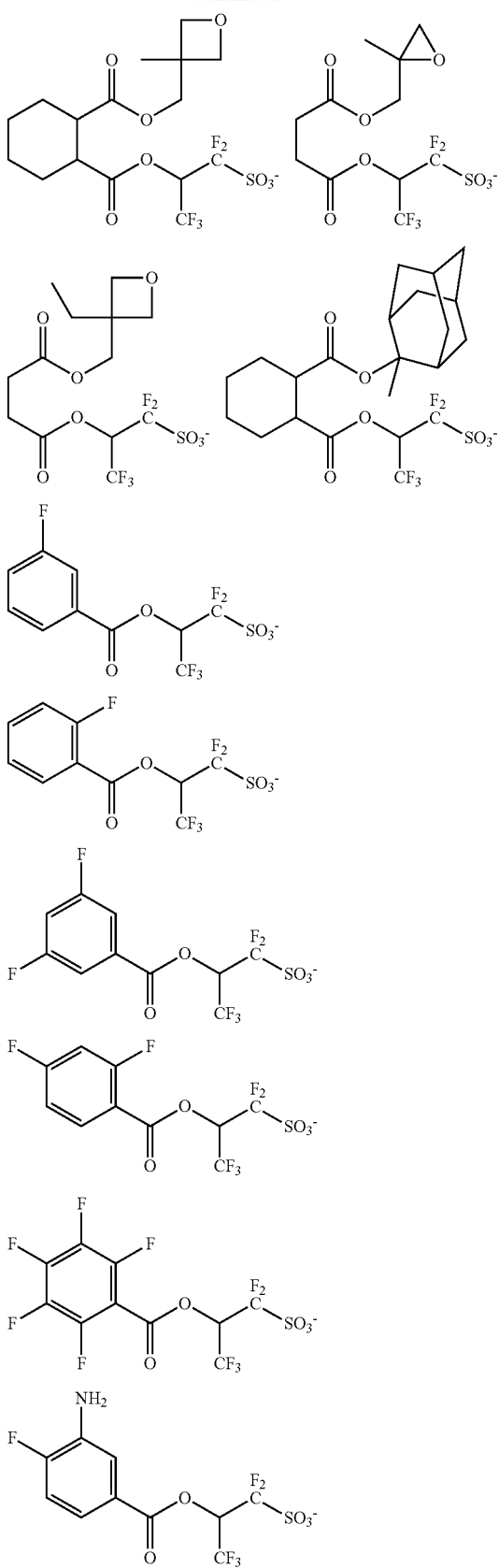

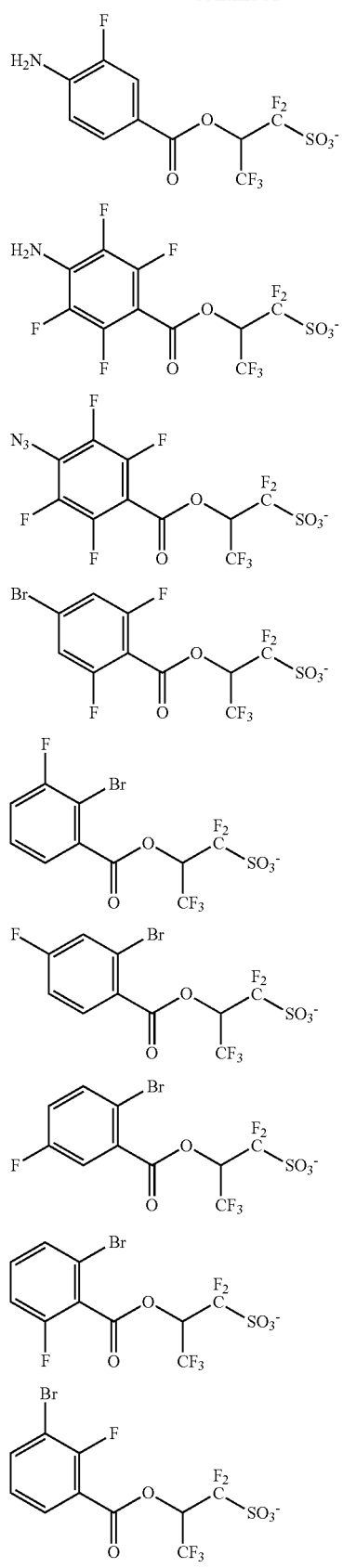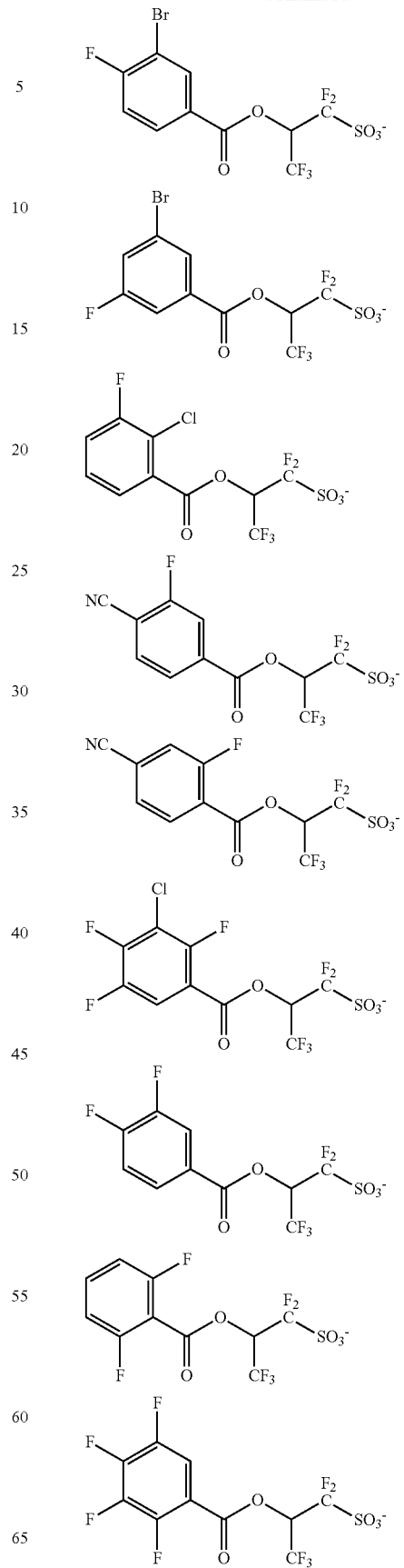

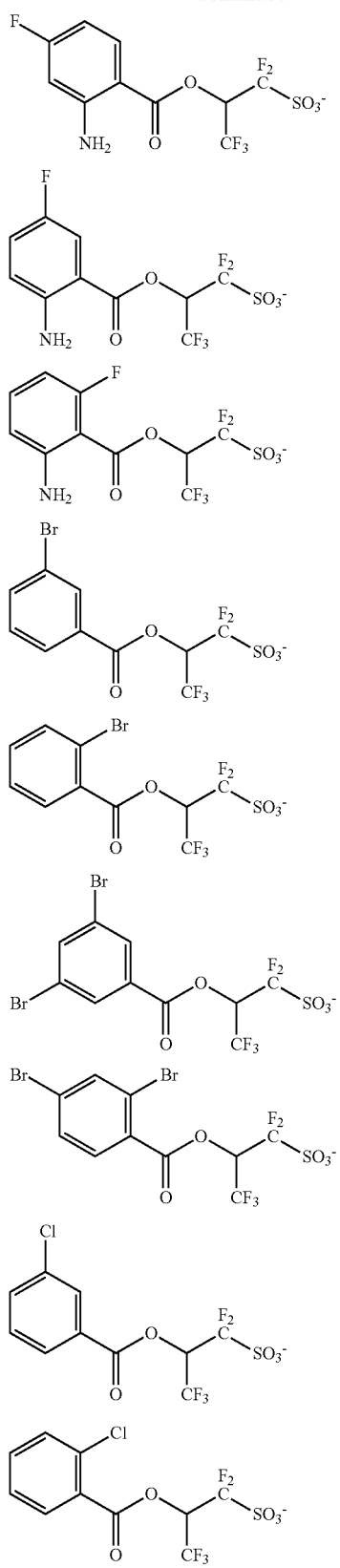
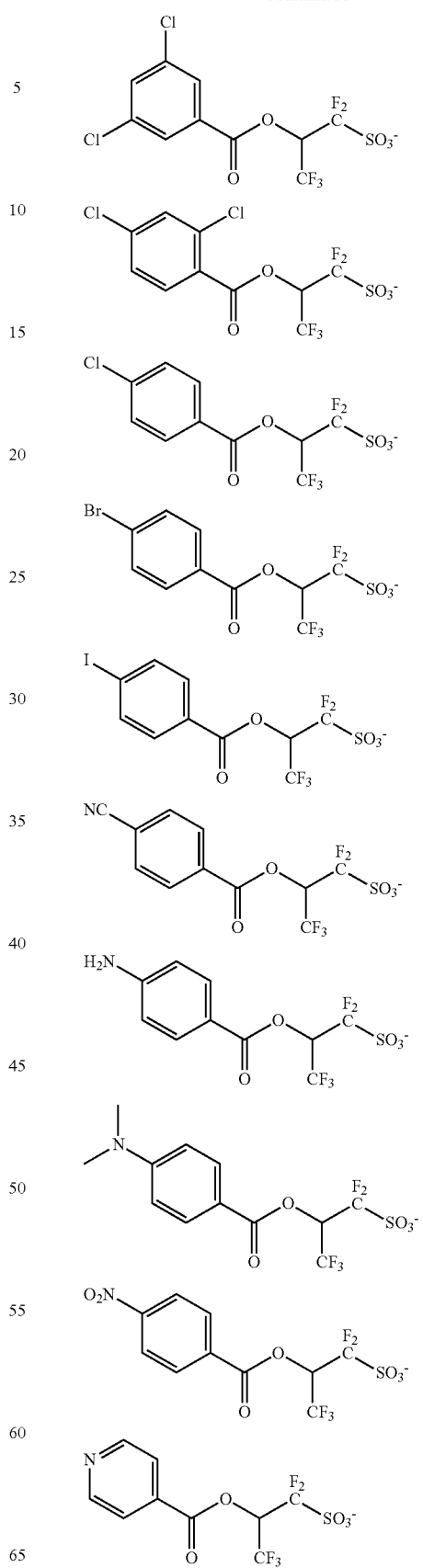

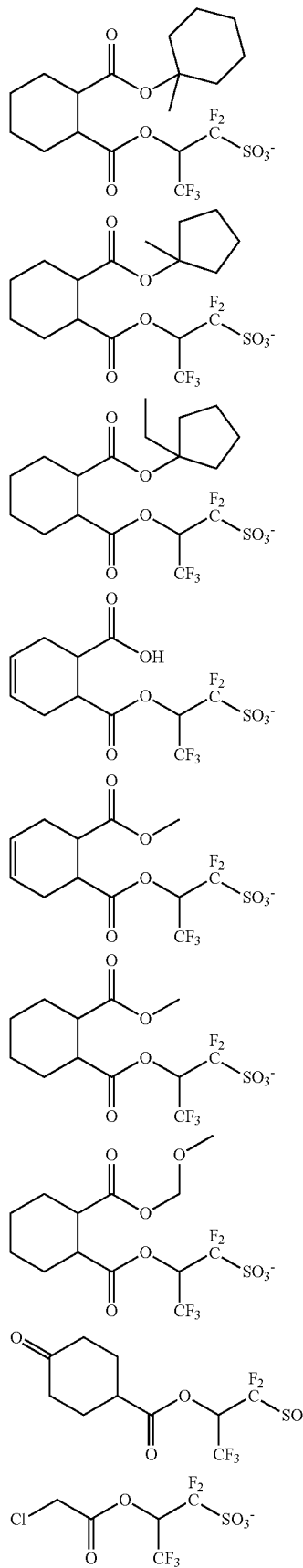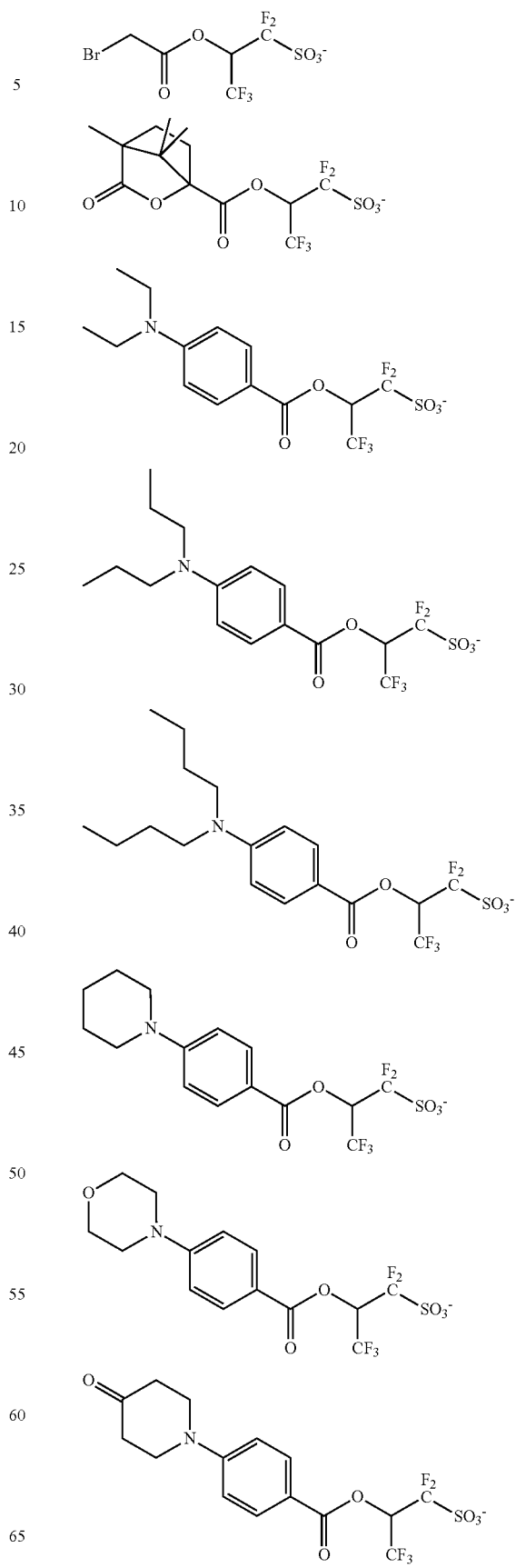

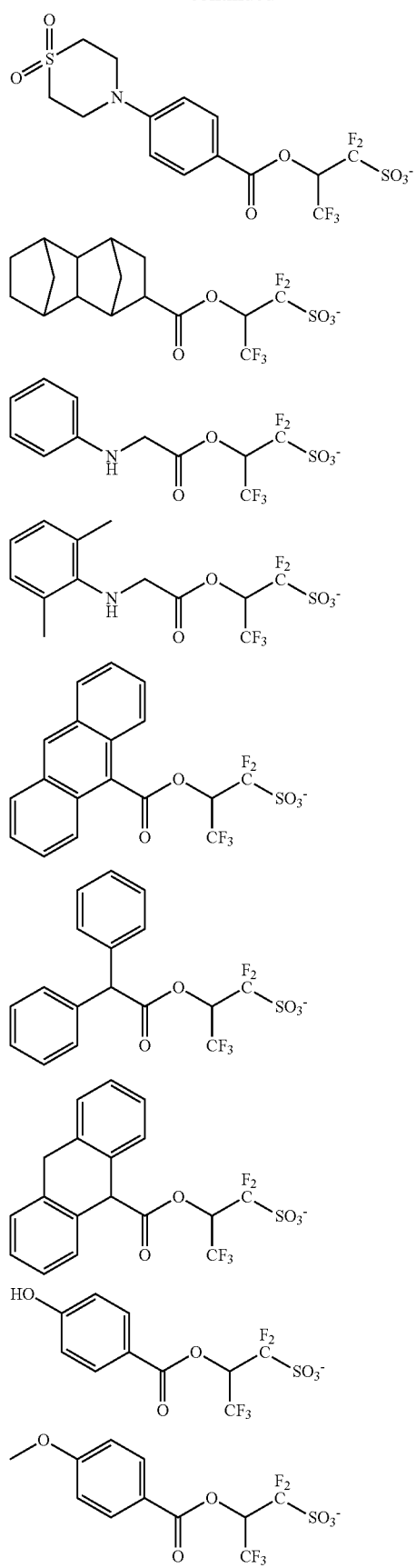
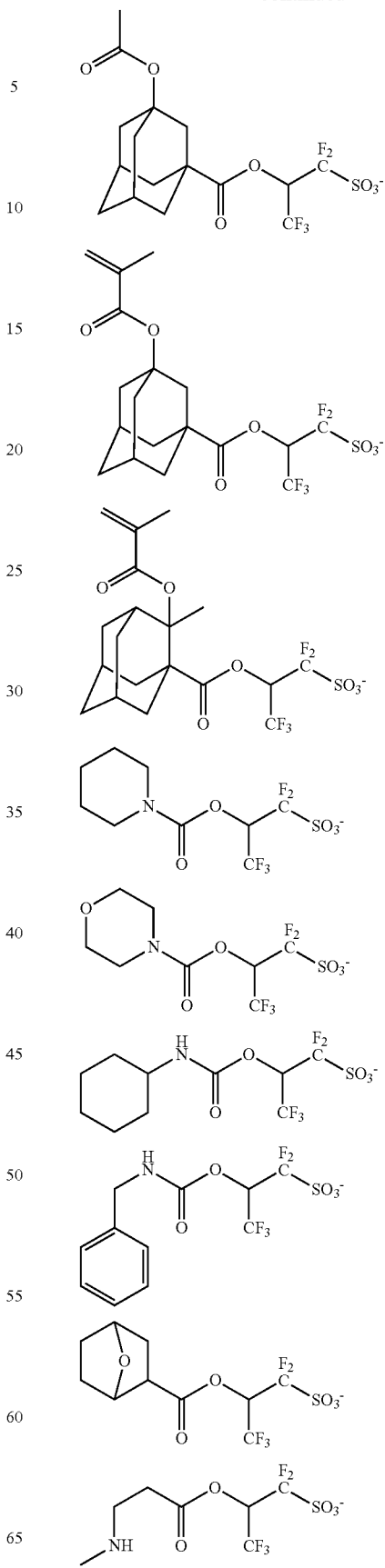

31
-continued
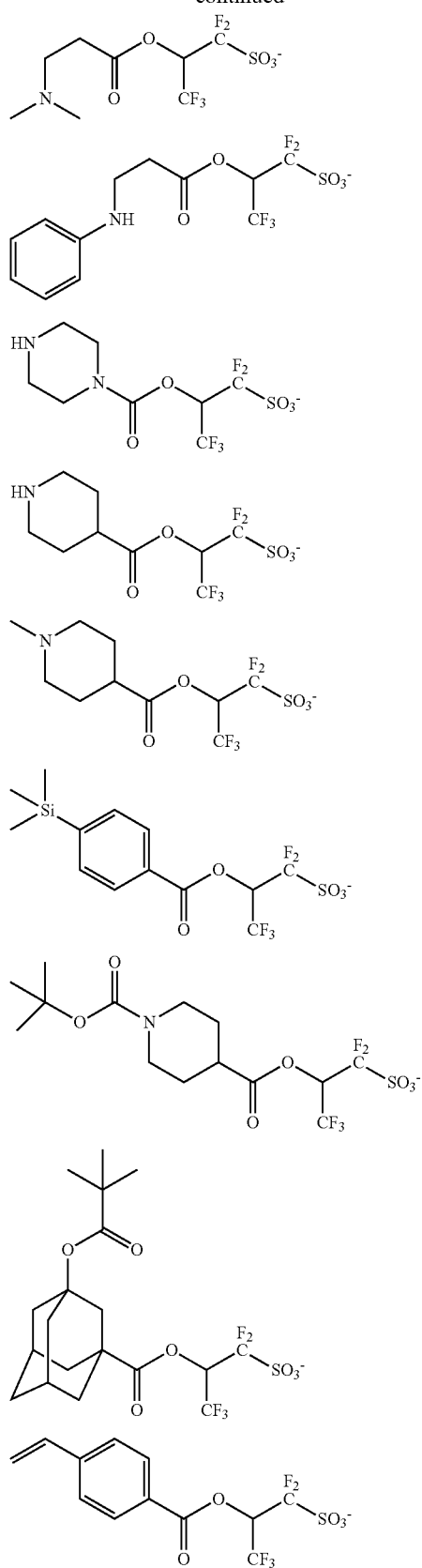
32
-continued
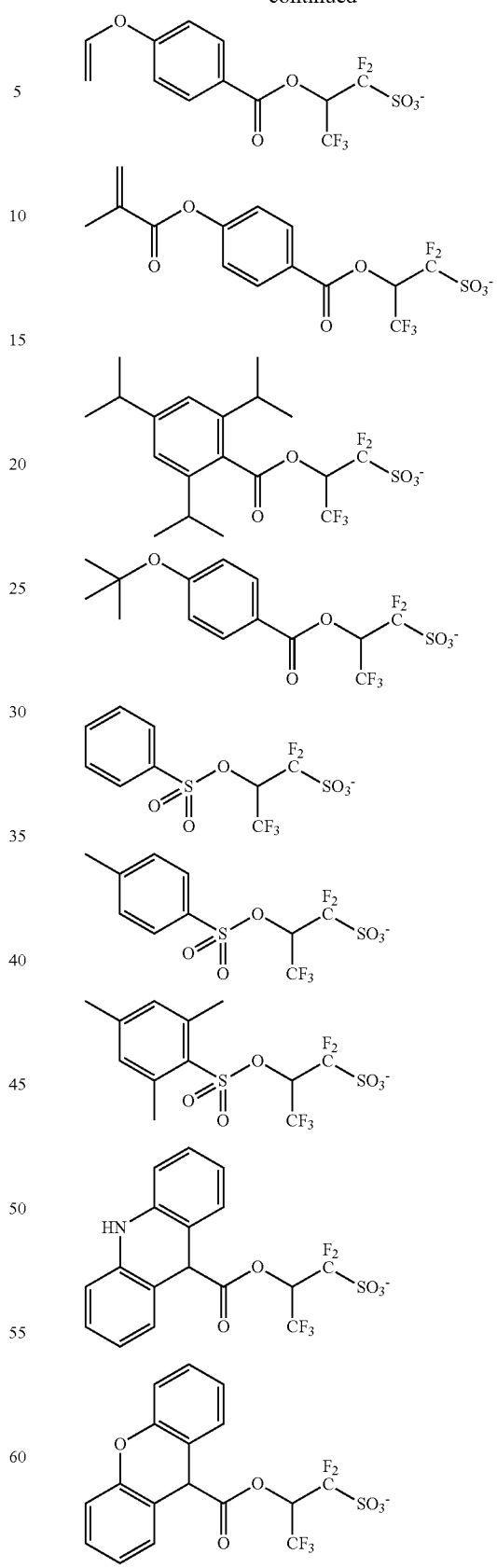

33
-continued
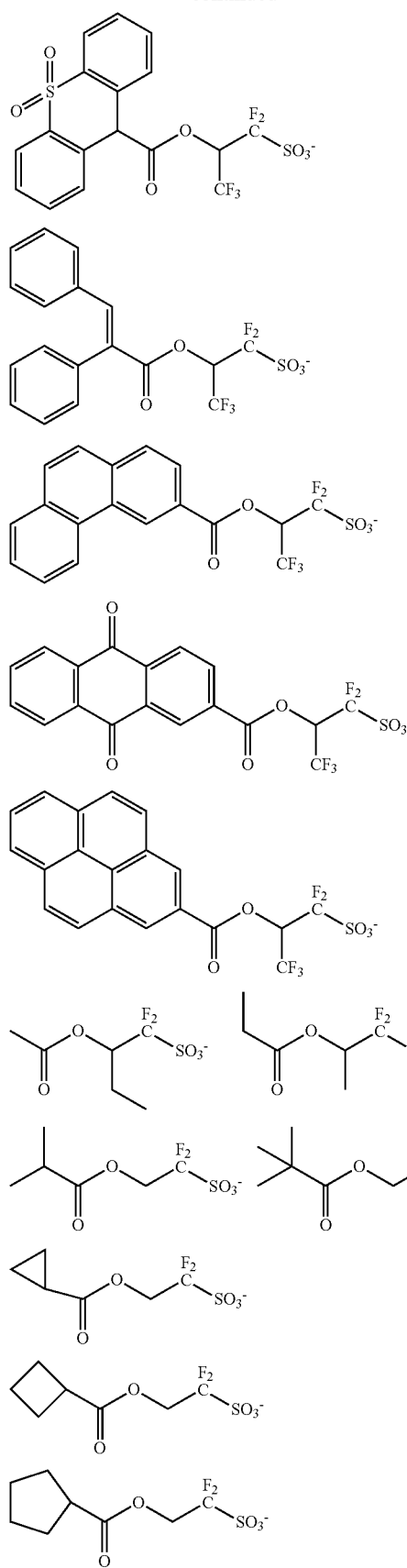
34
-continued
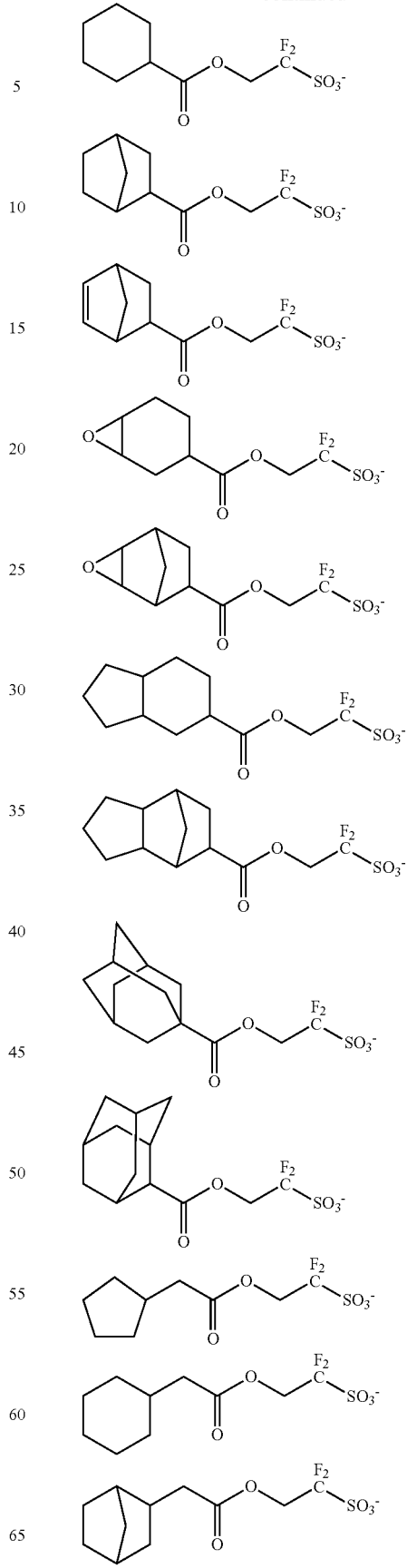

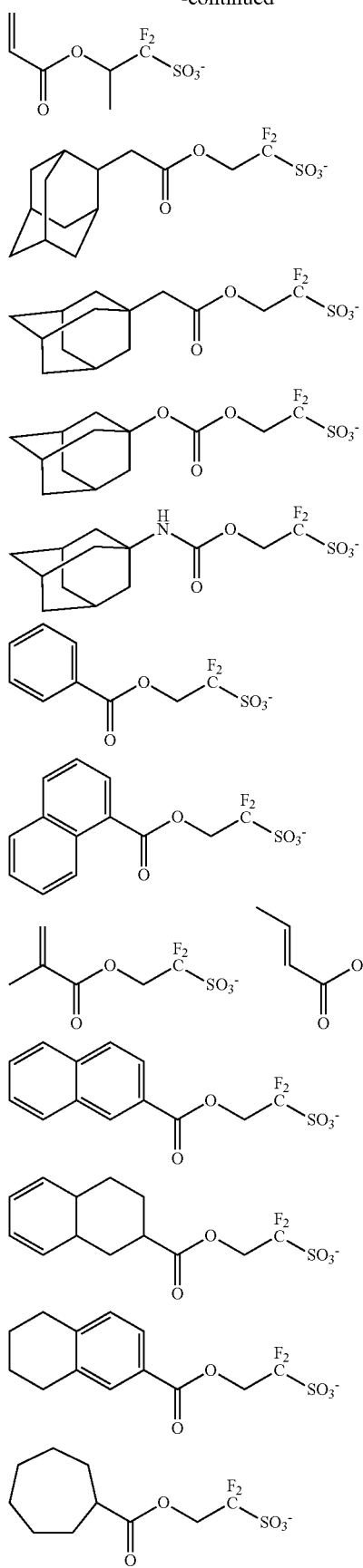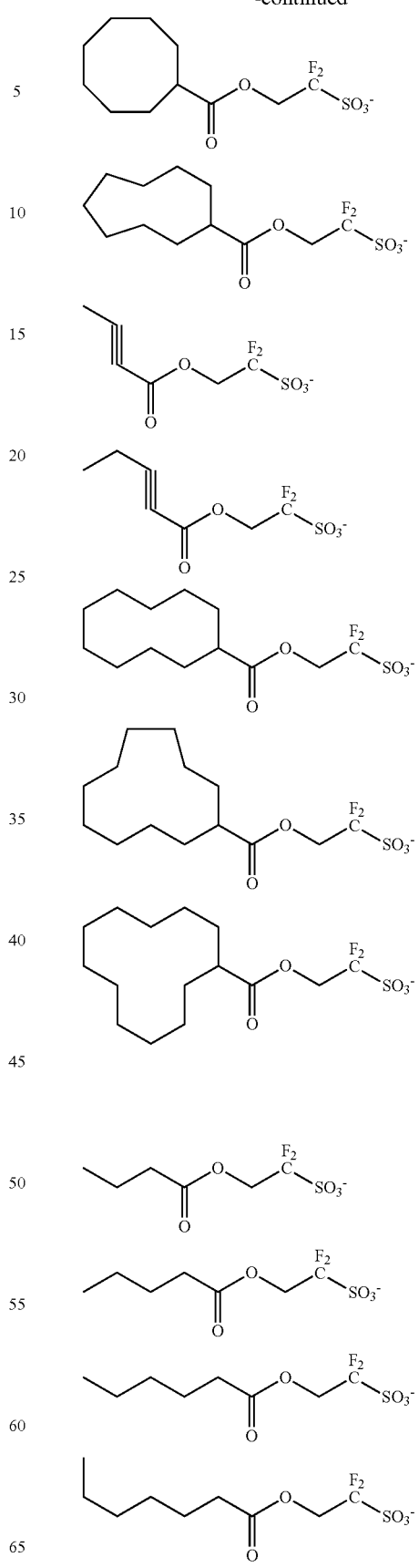

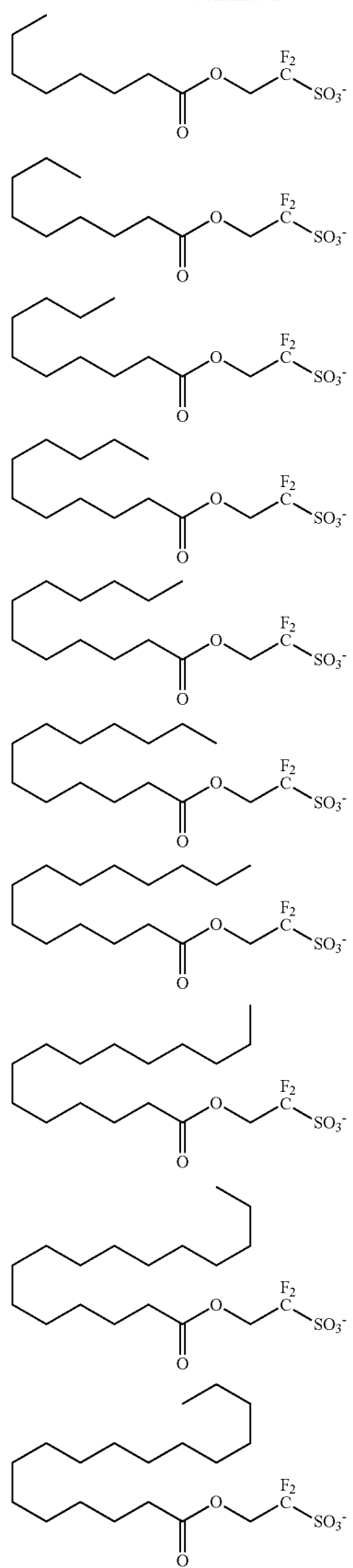
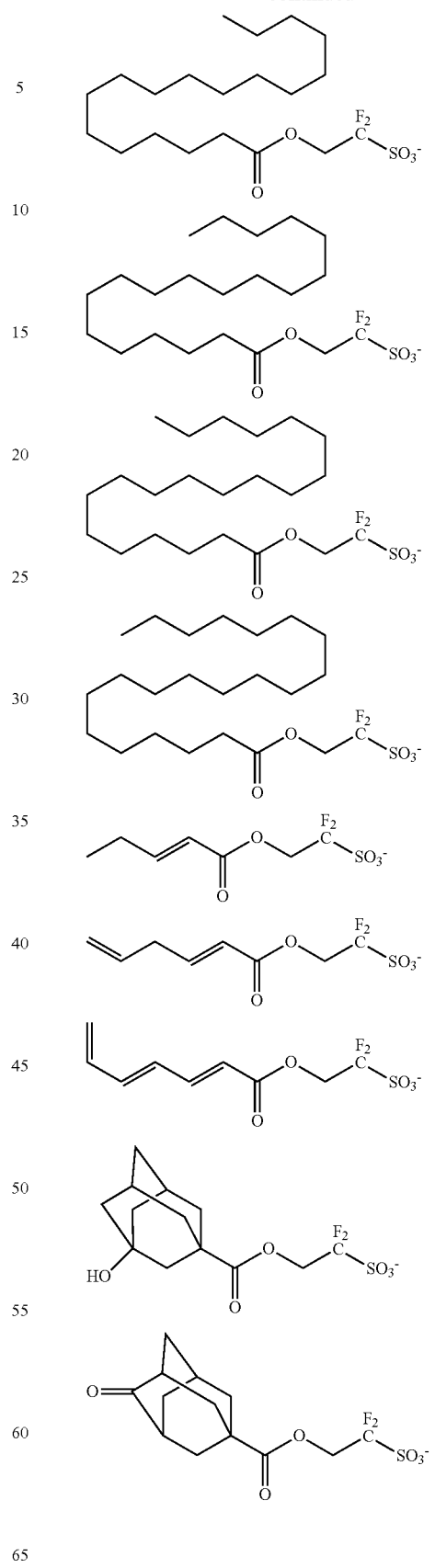

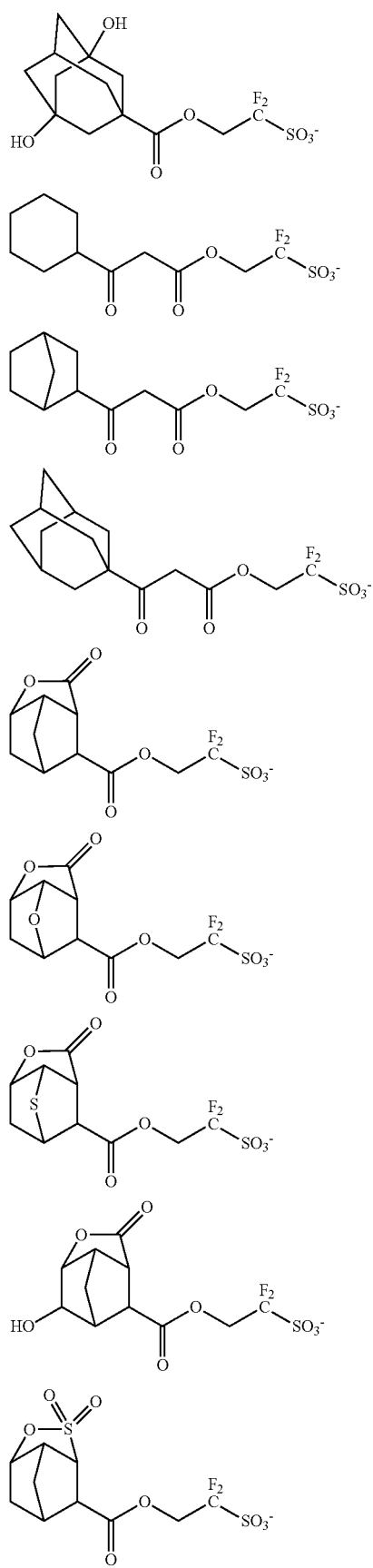
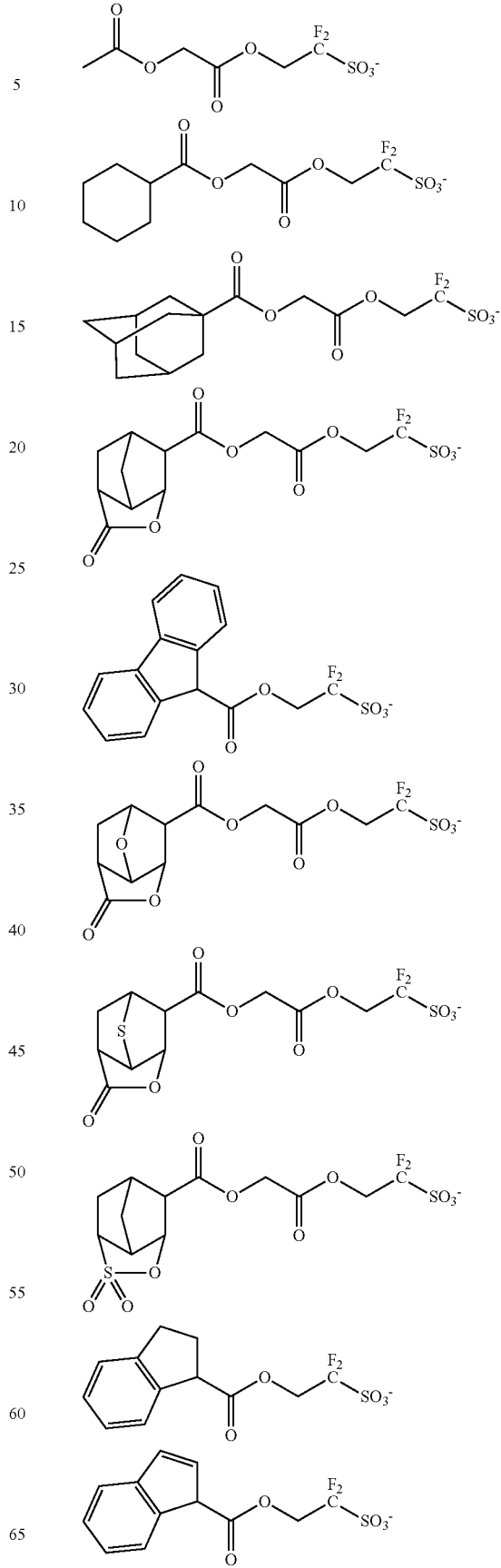

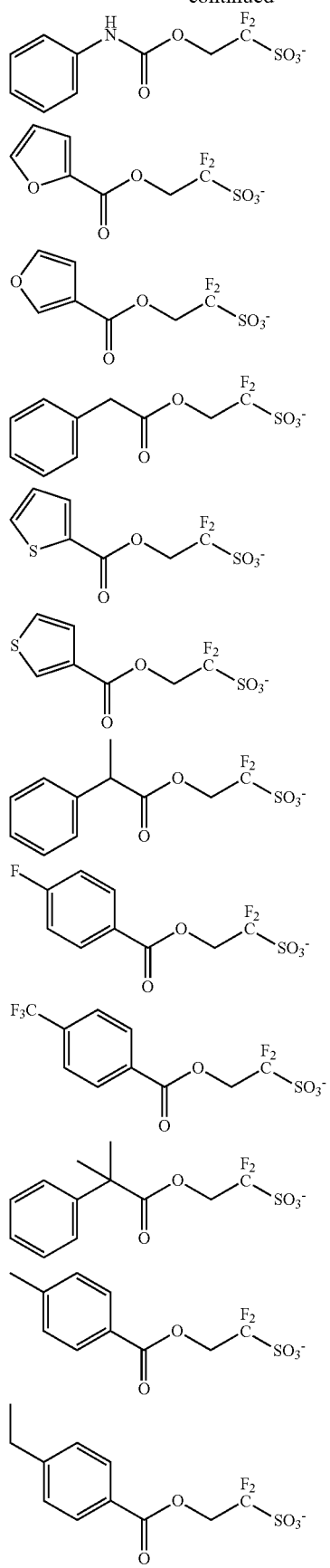
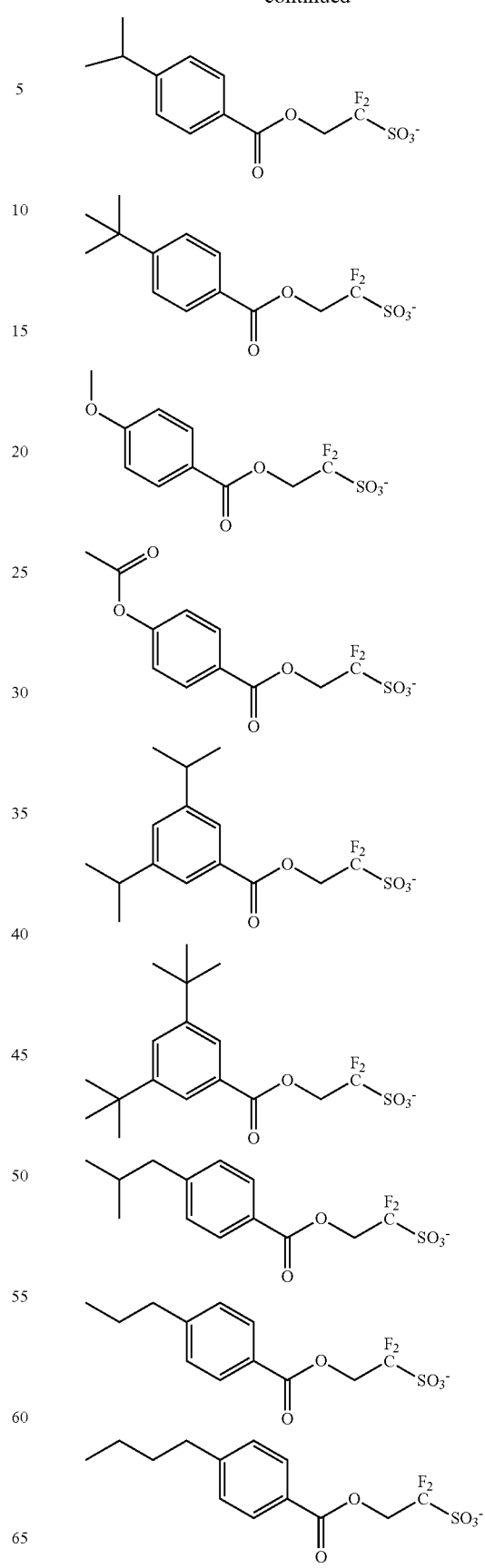

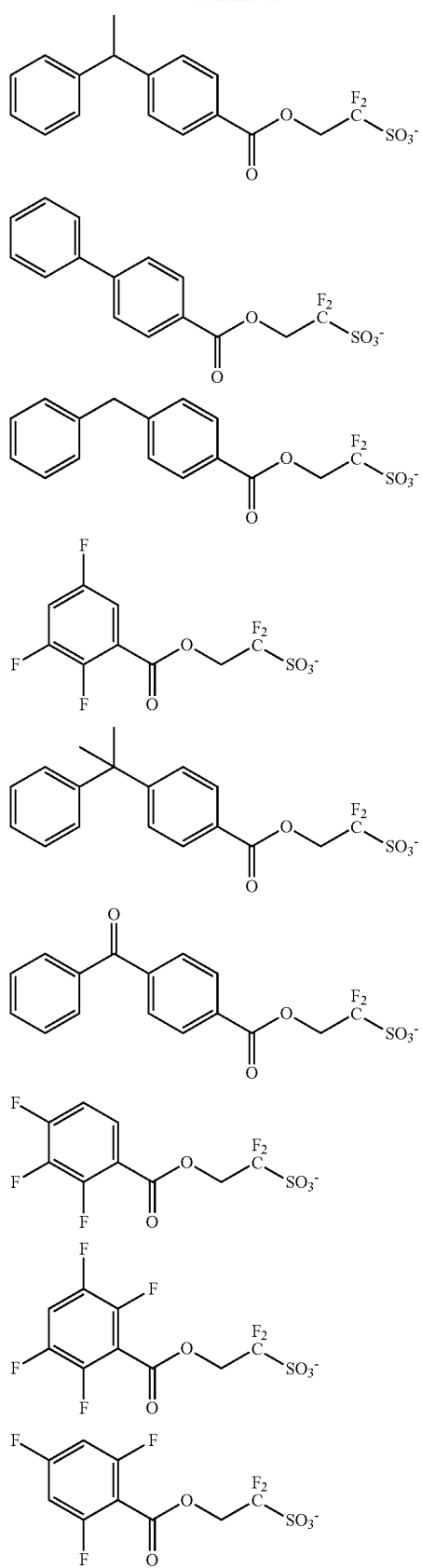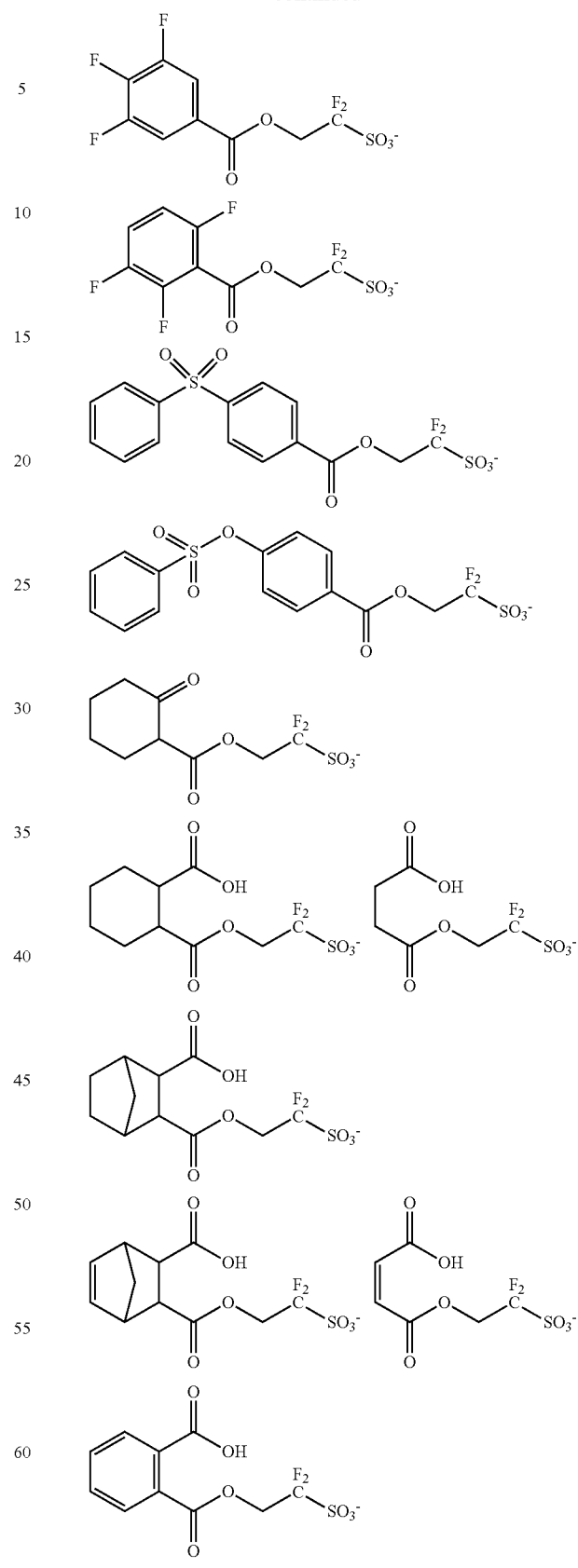

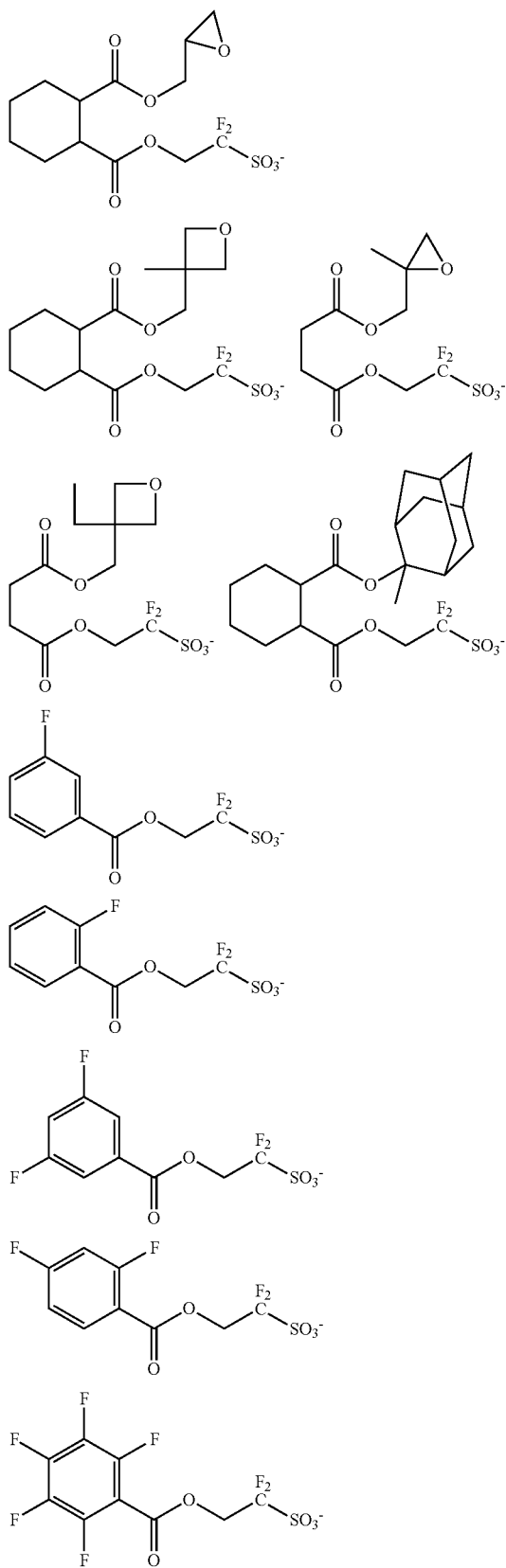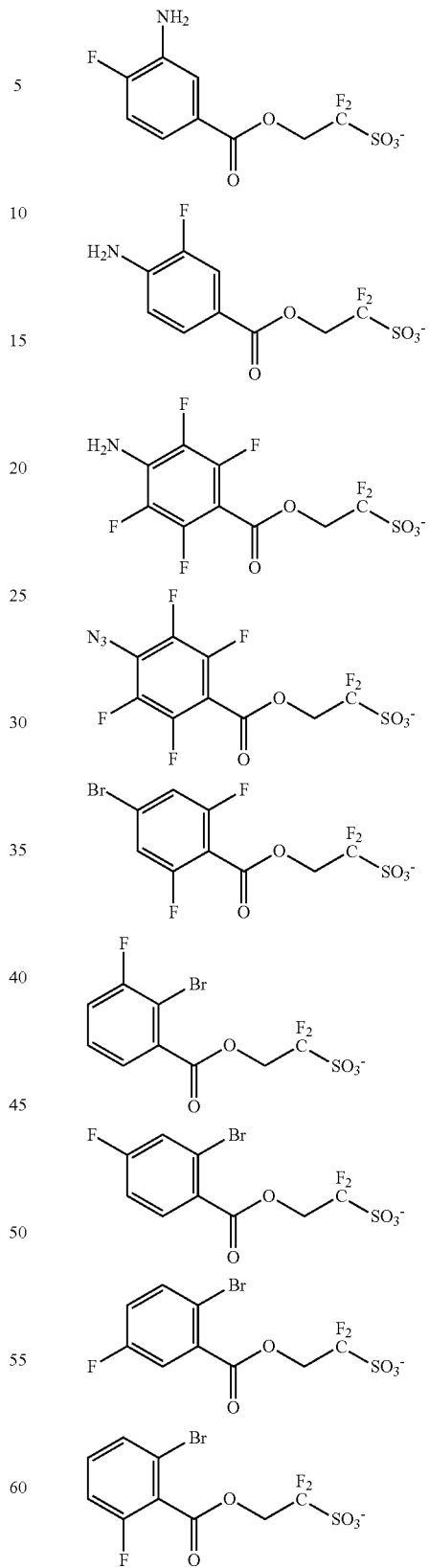

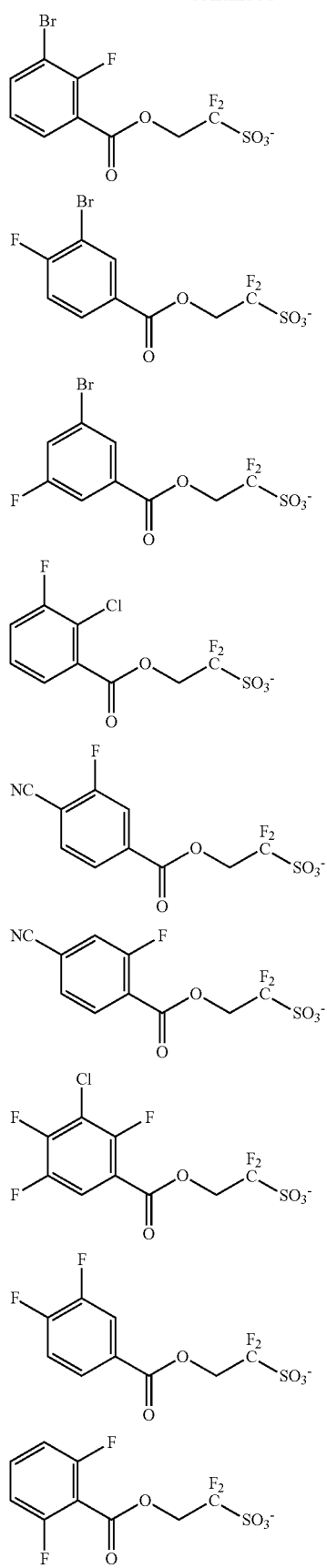
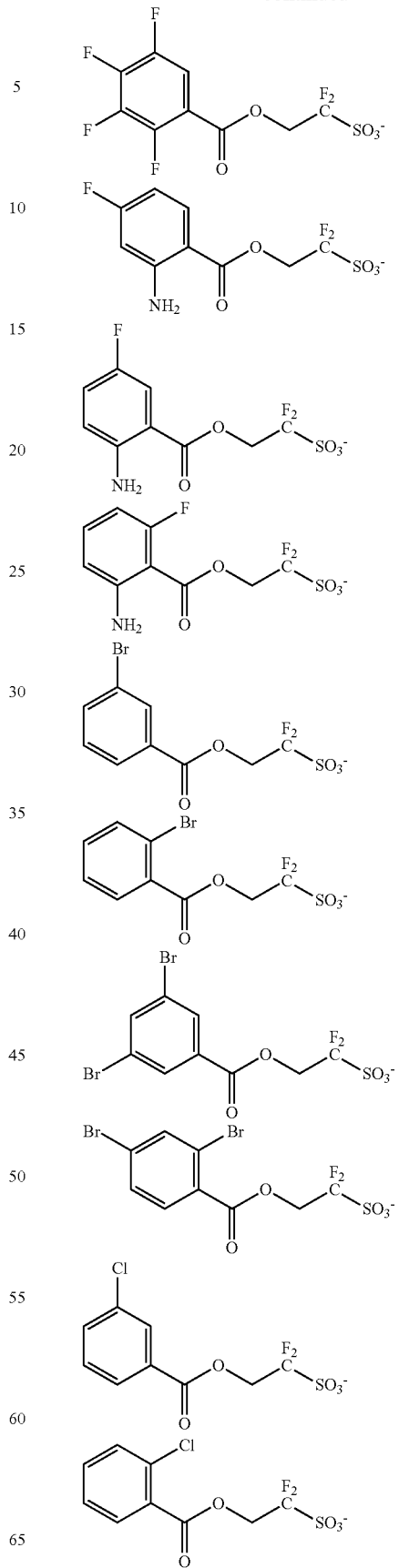

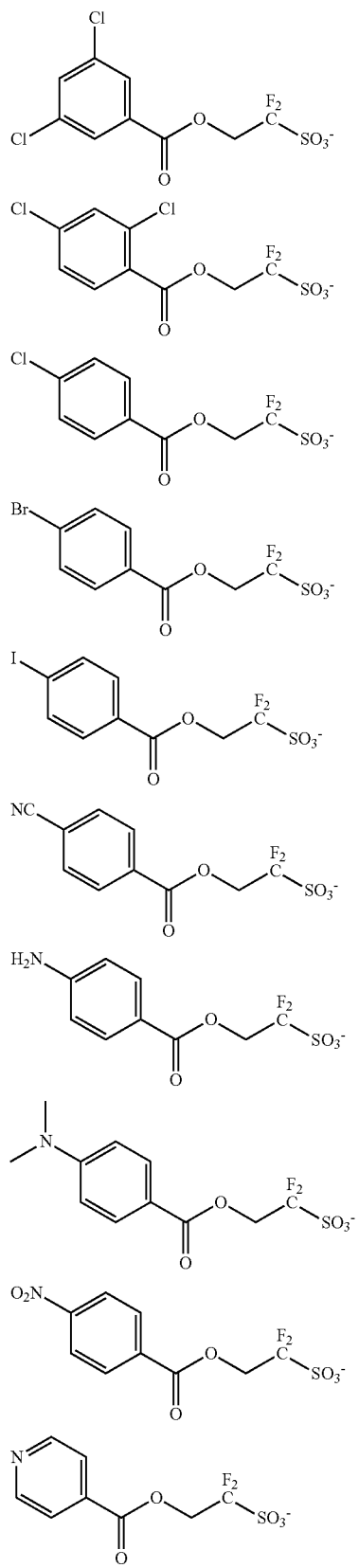
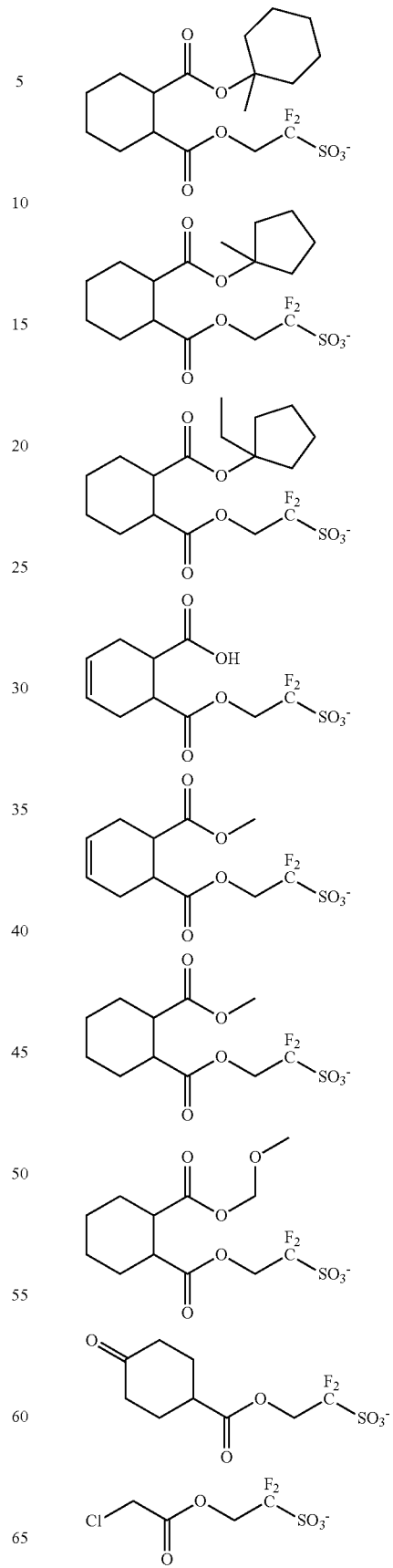

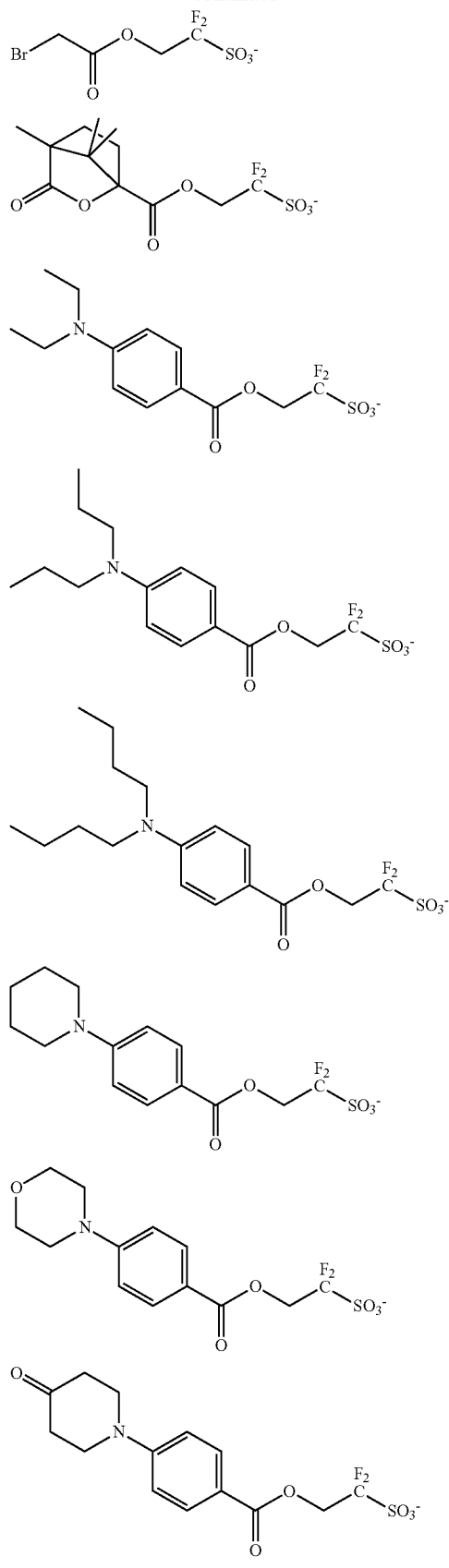
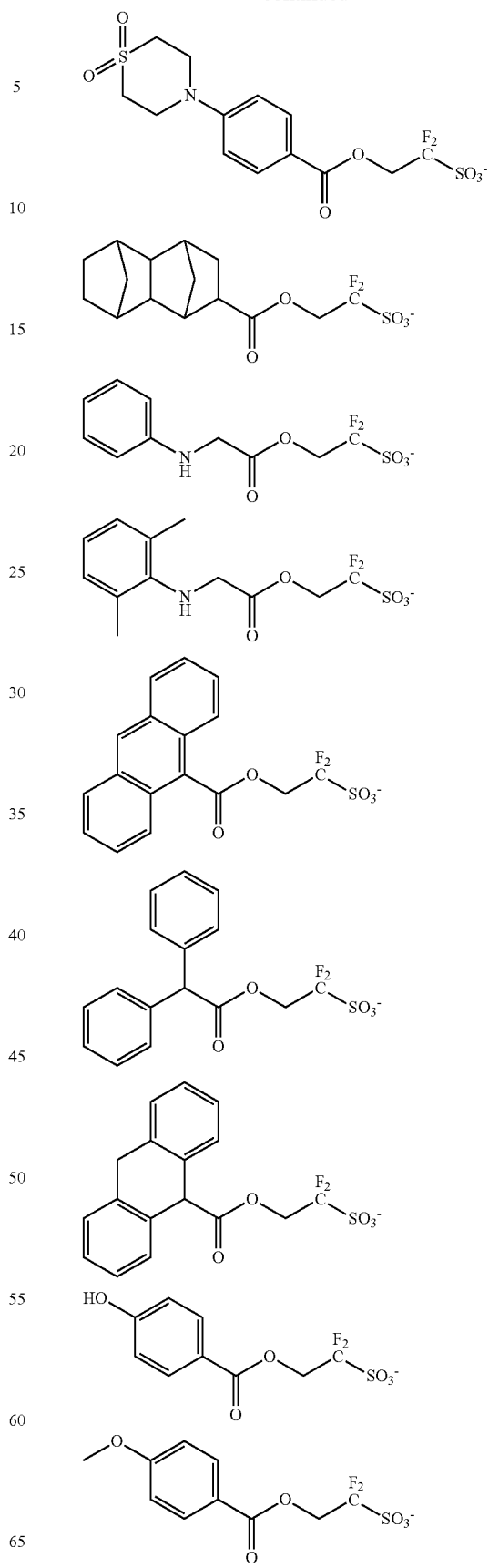

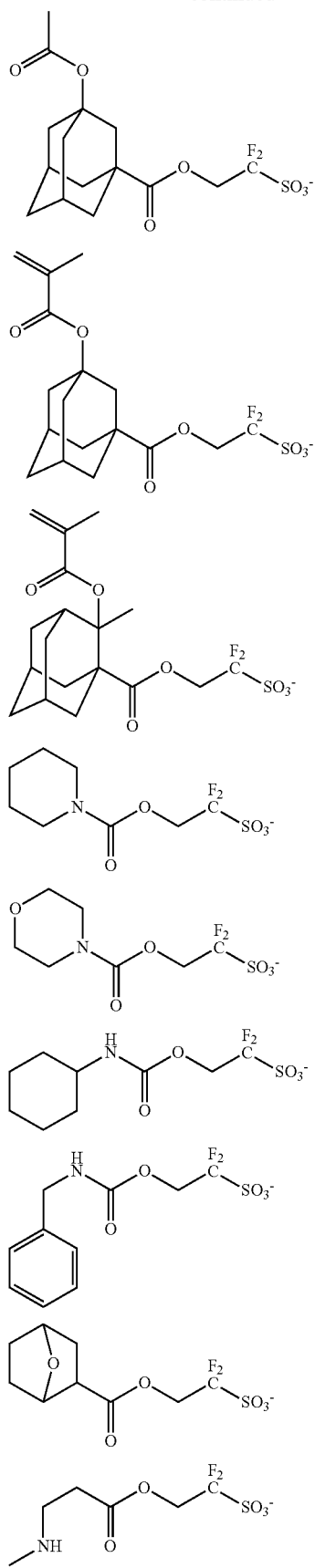
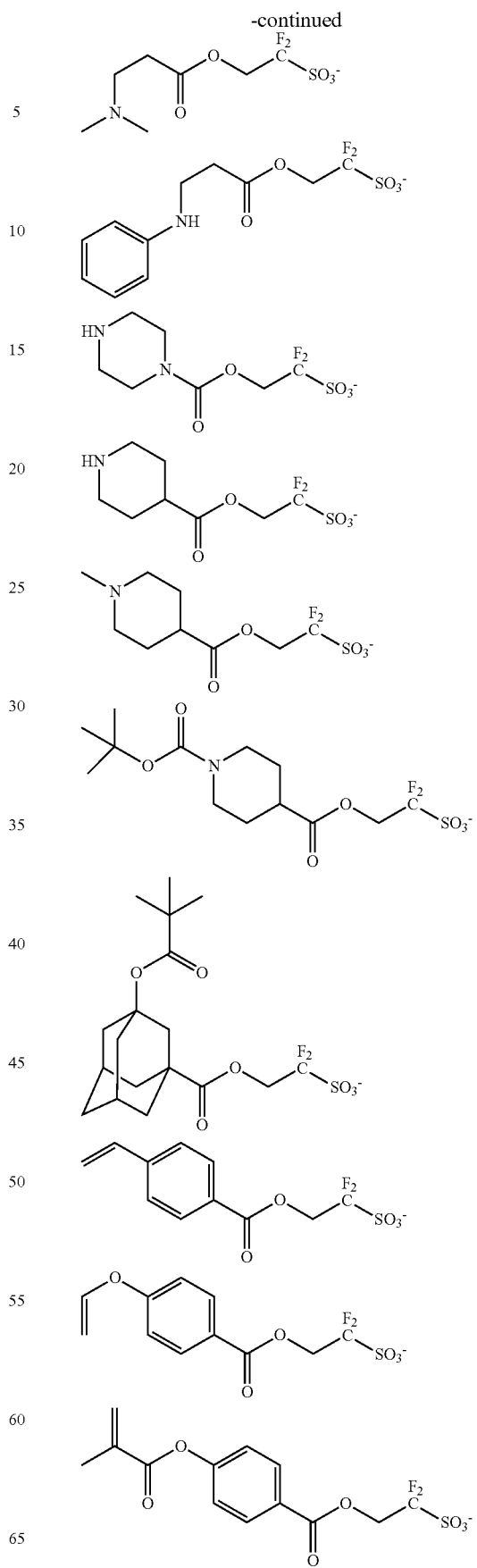

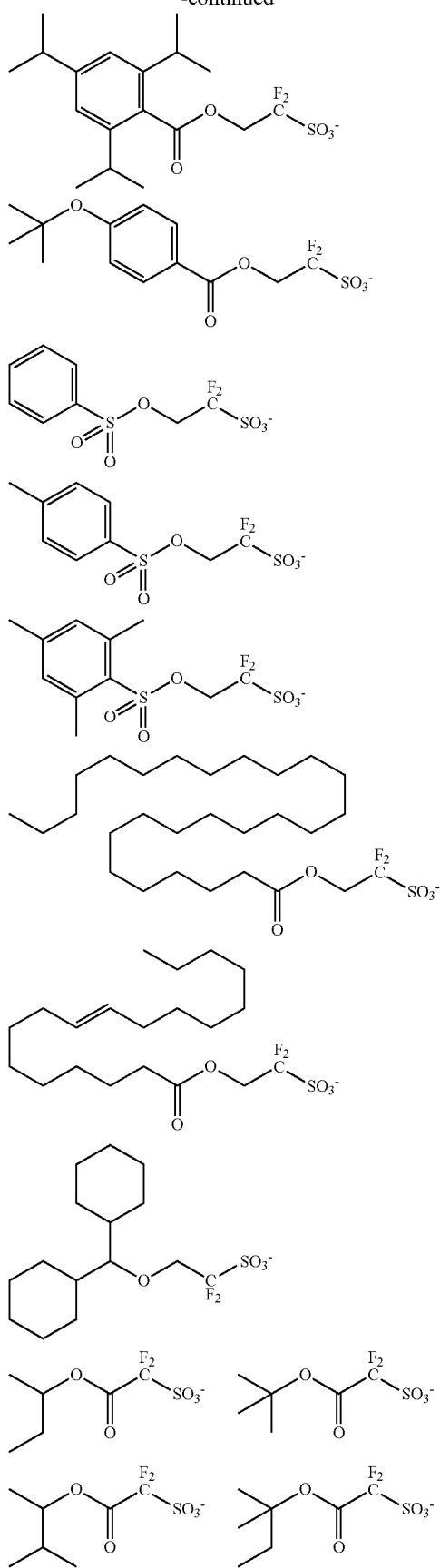
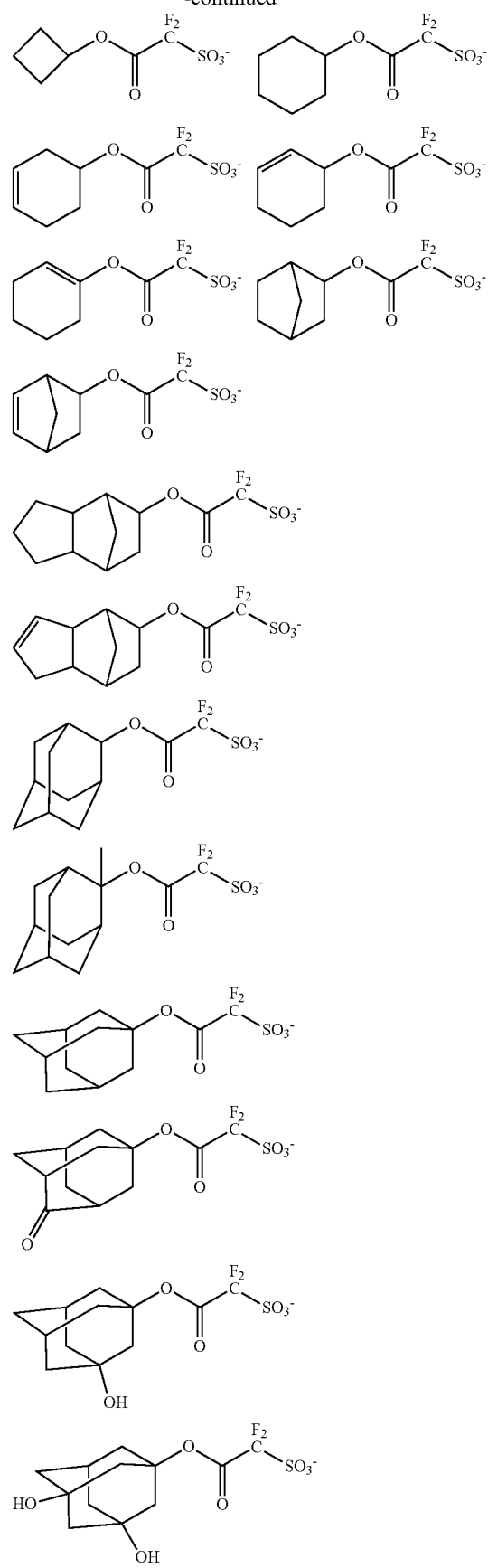

-continued
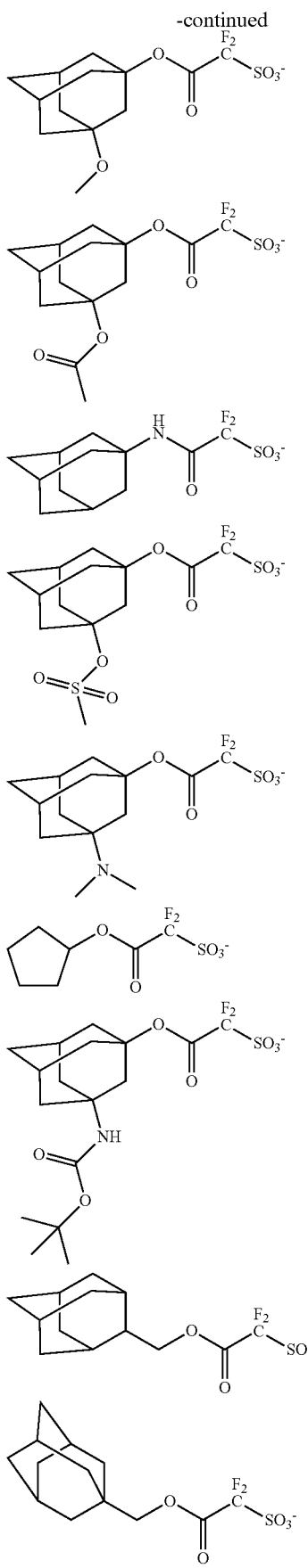

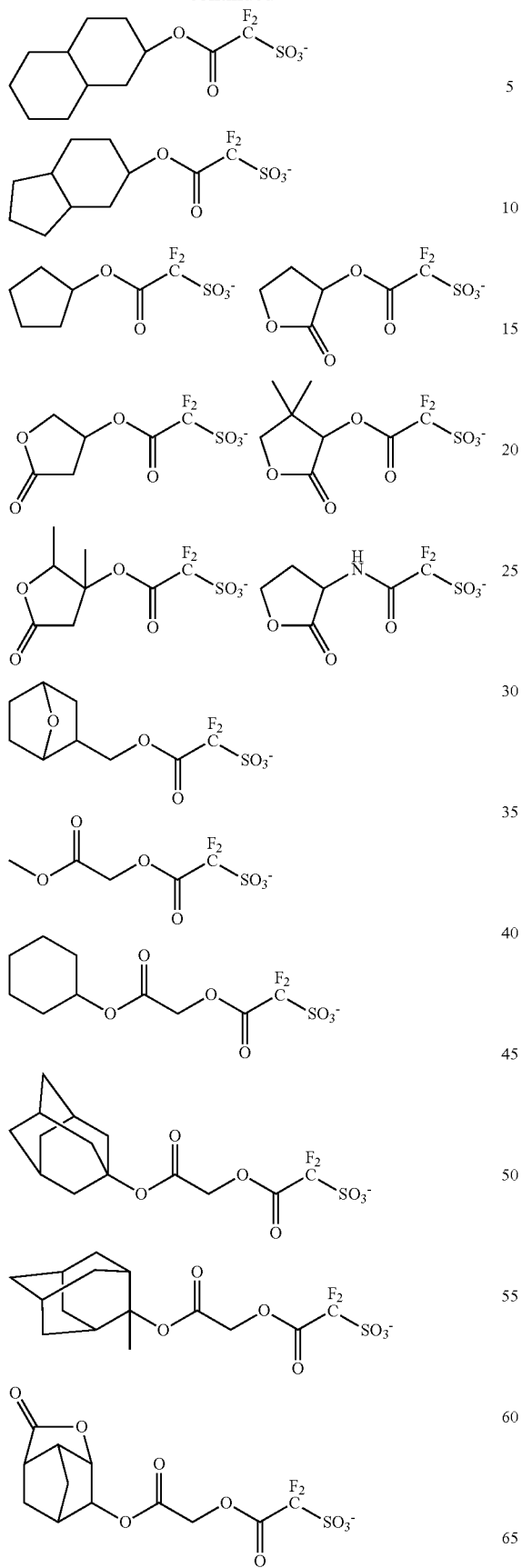
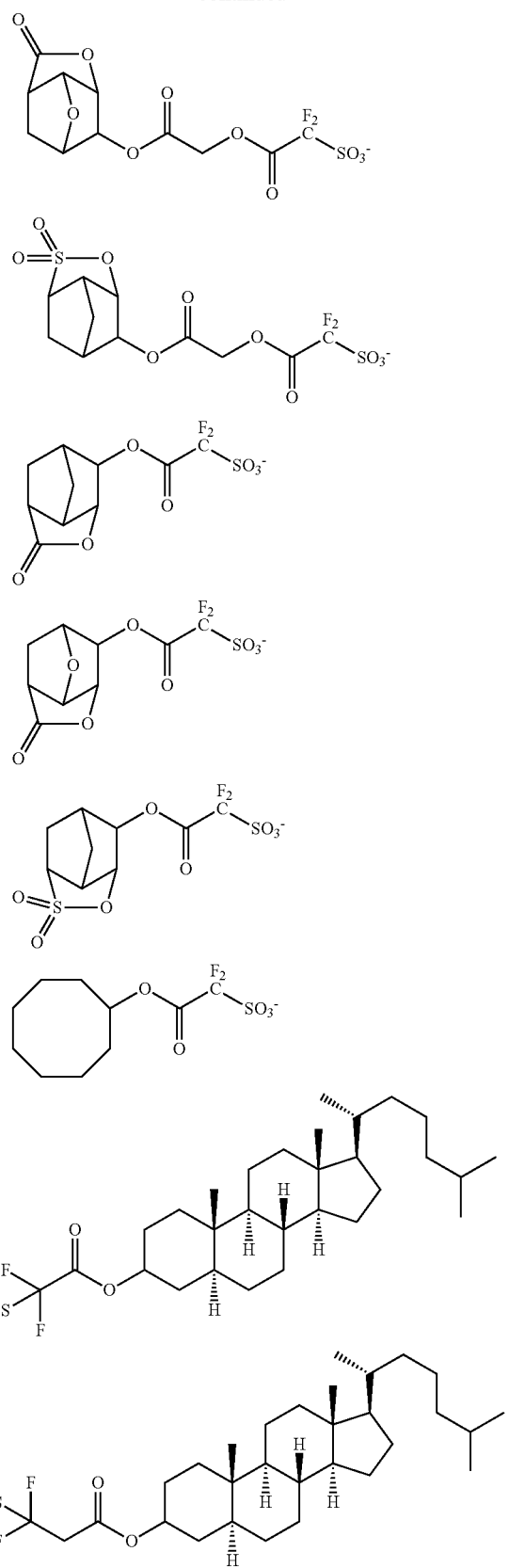

-continued
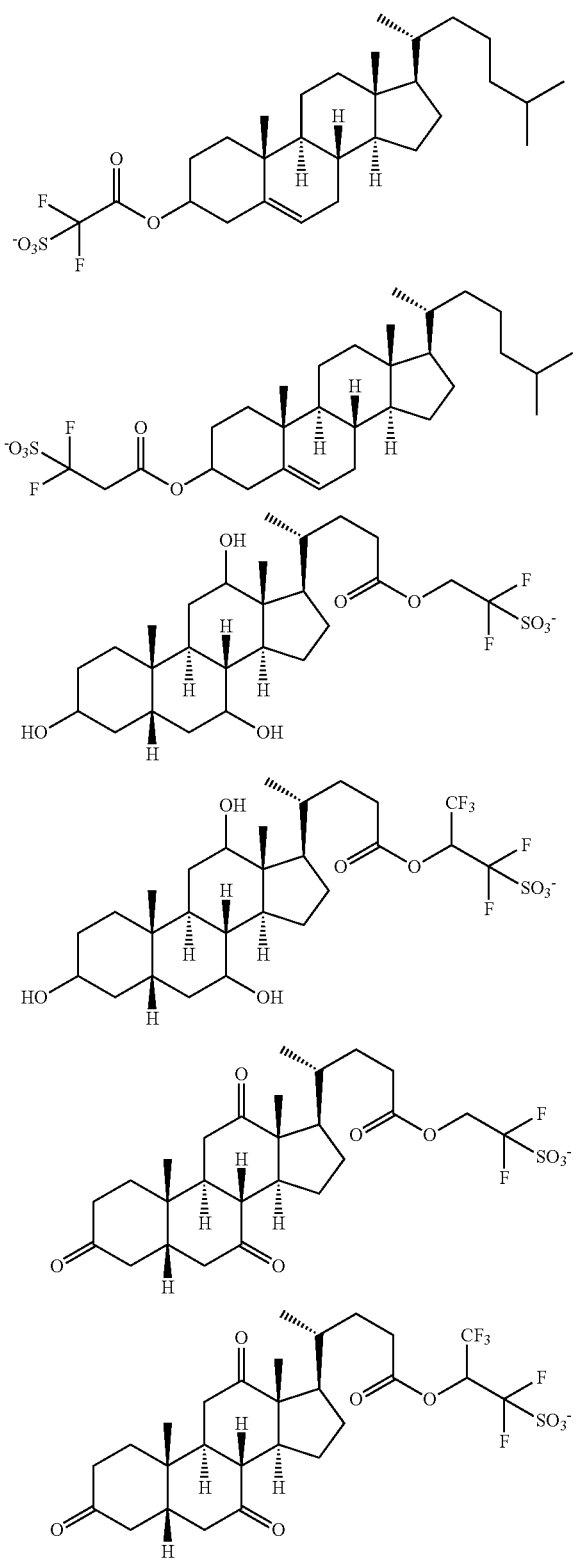
-continued
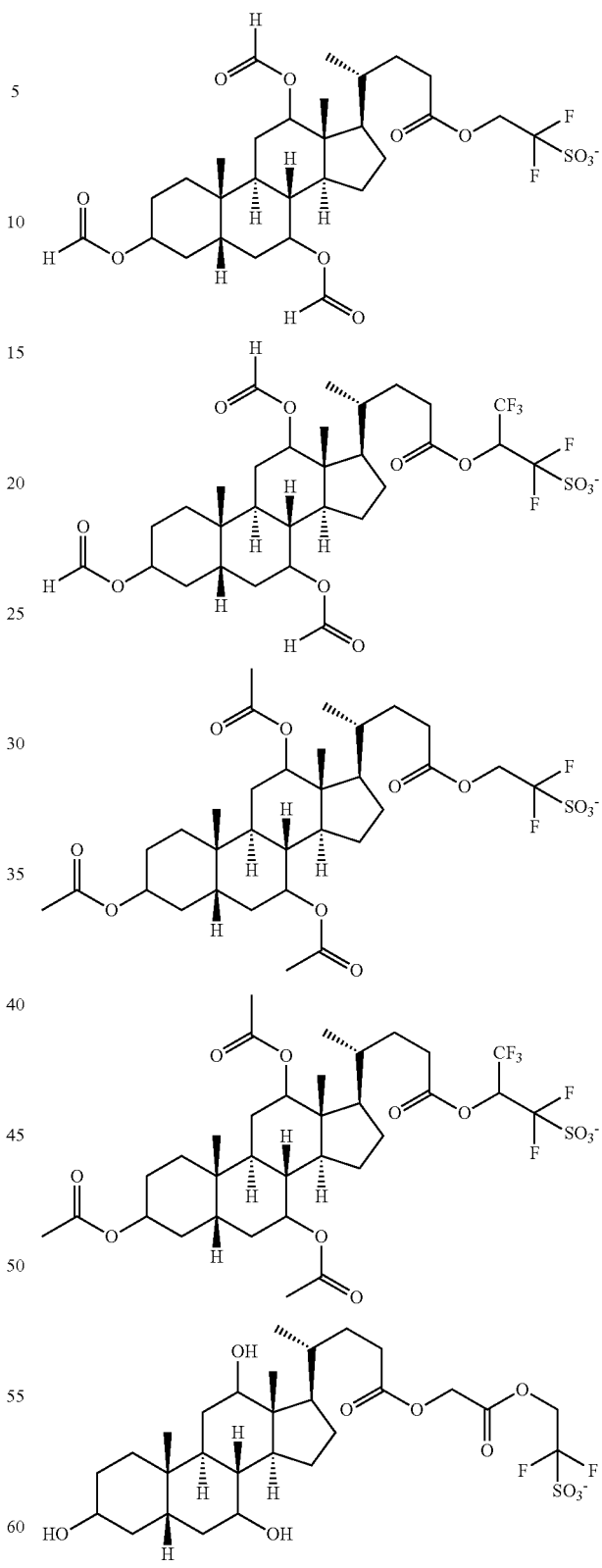

63
-continued
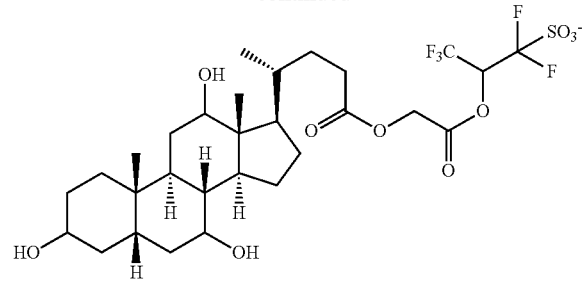
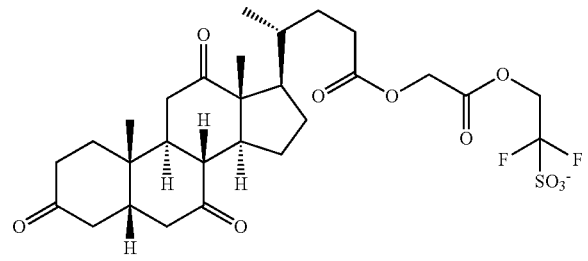
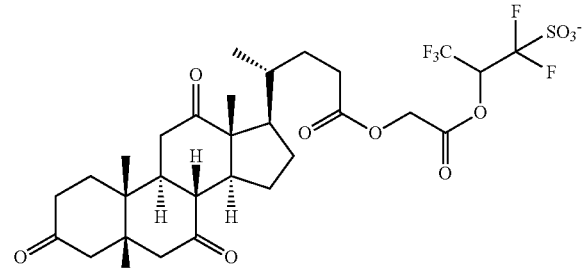
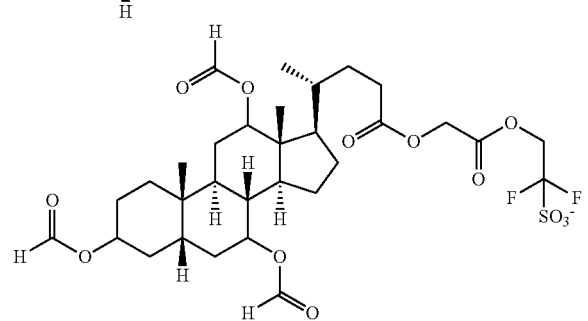
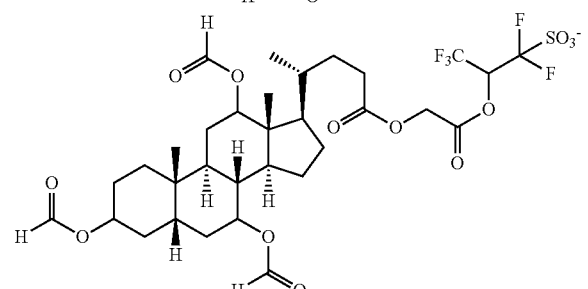
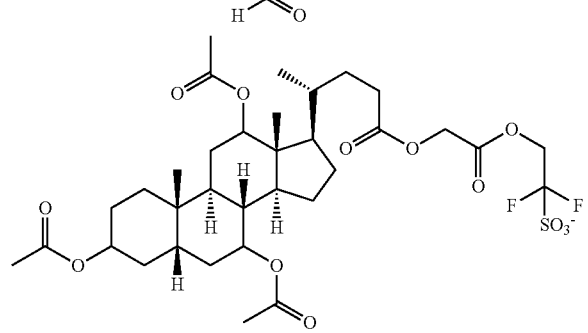
64
-continued
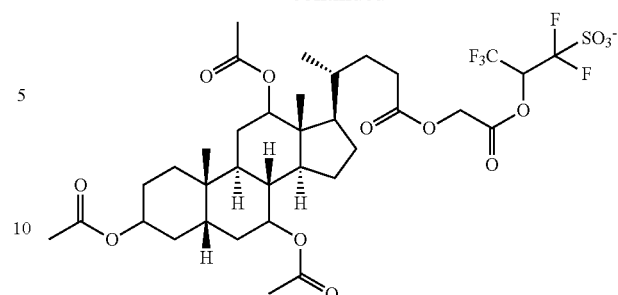
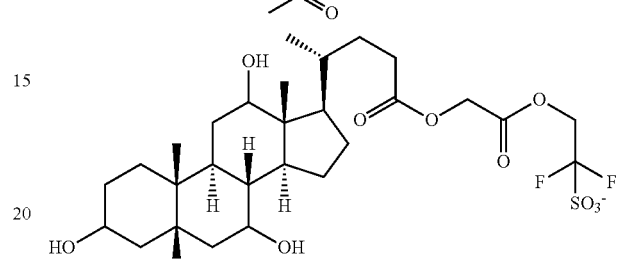
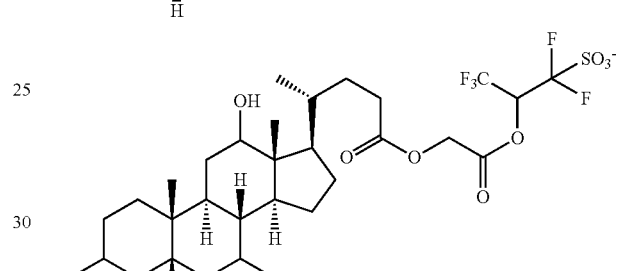
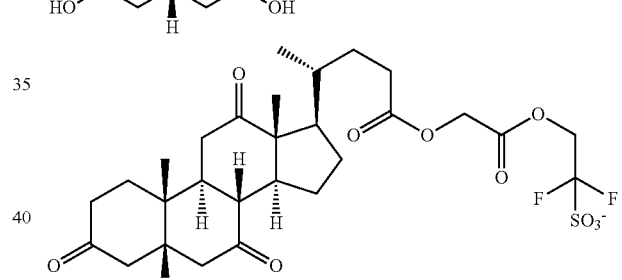
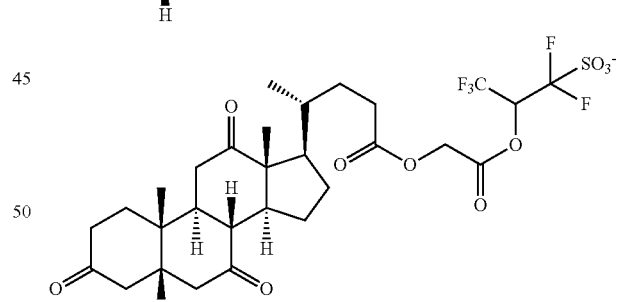
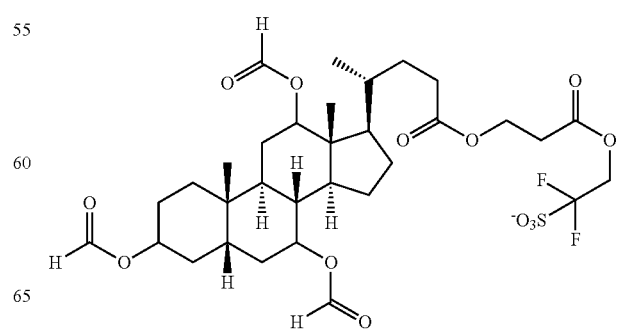

65
-continued
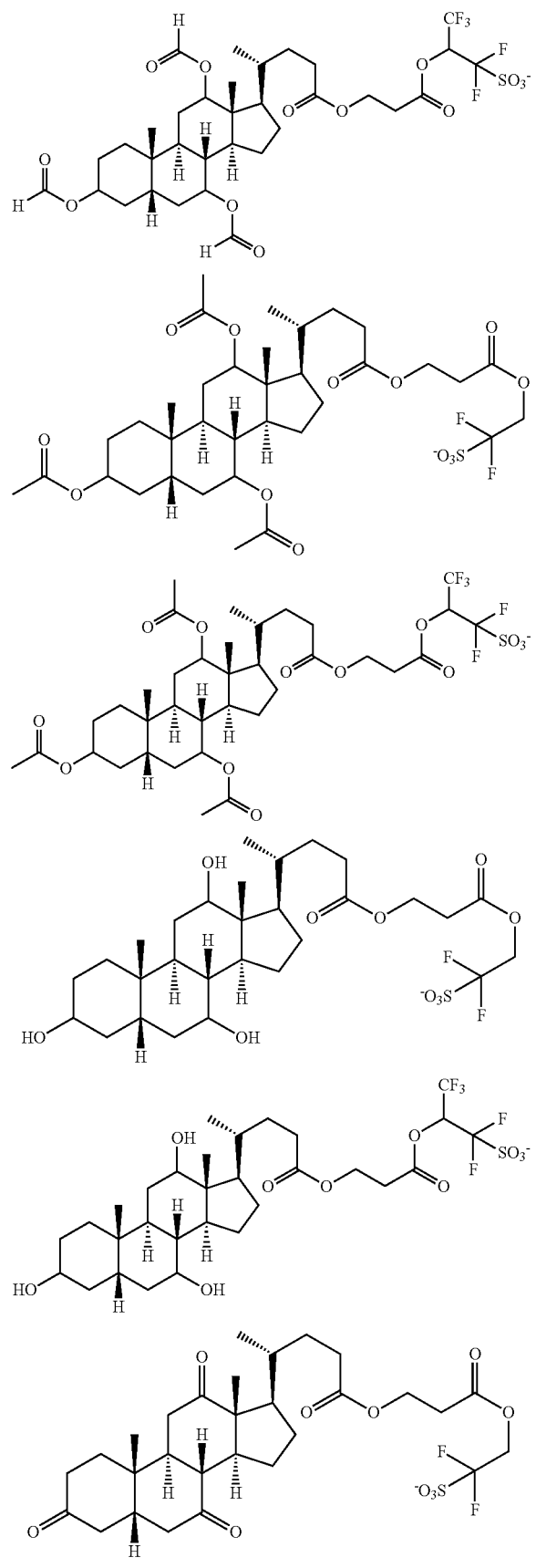
66
-continued
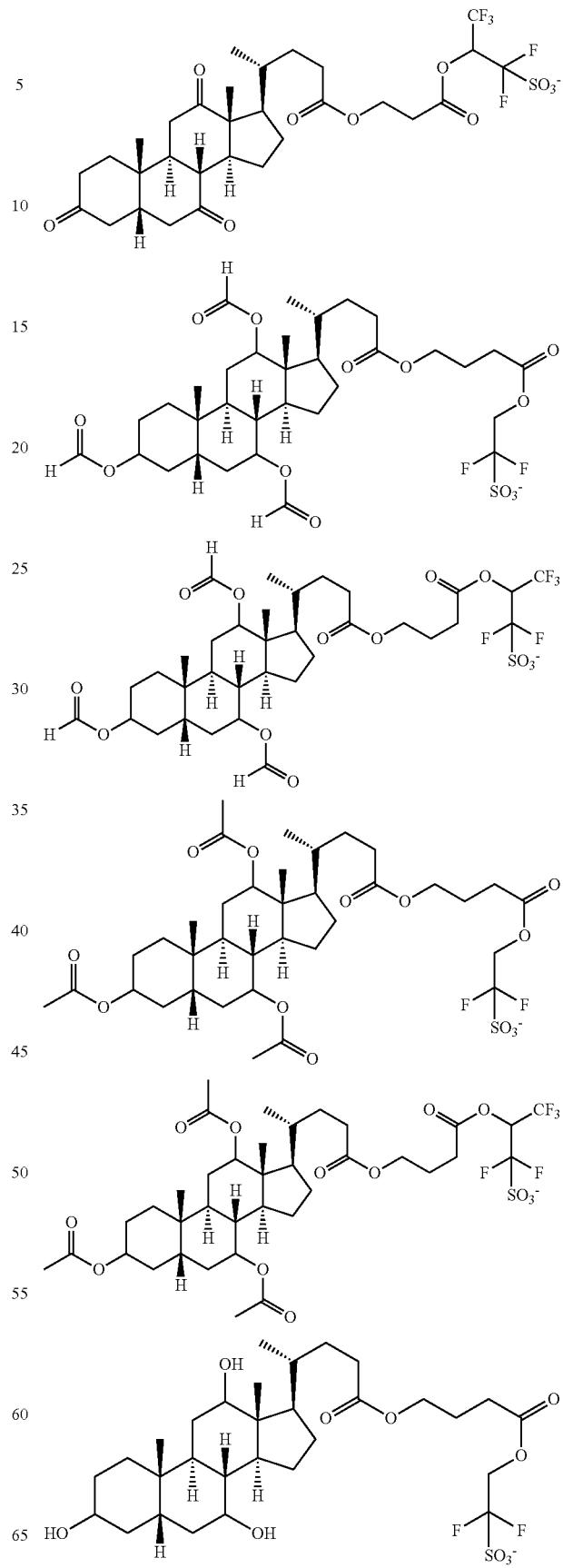

-continued
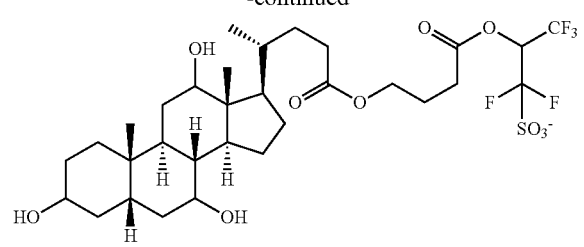
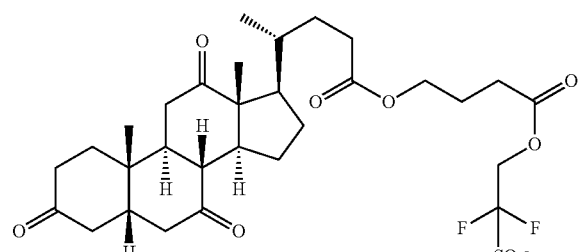
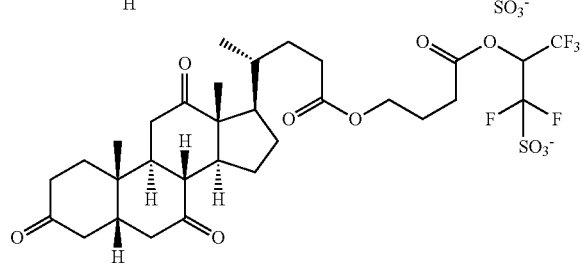
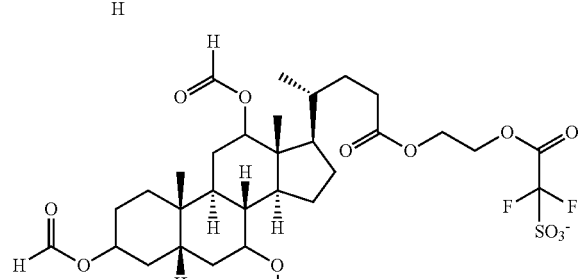
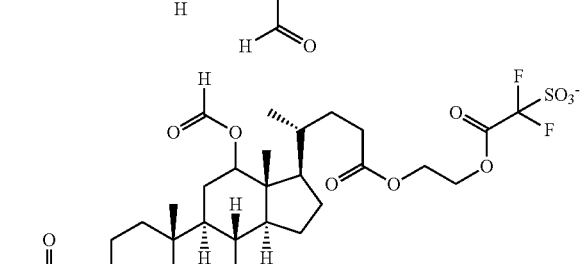
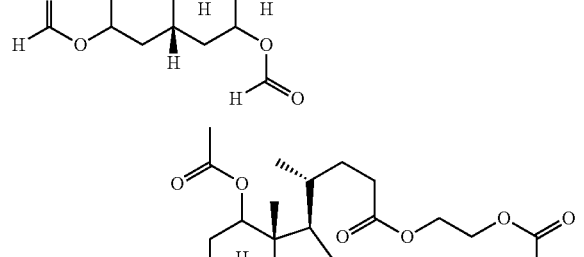
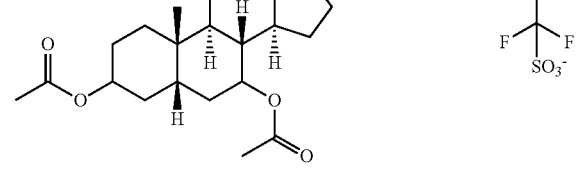
-continued
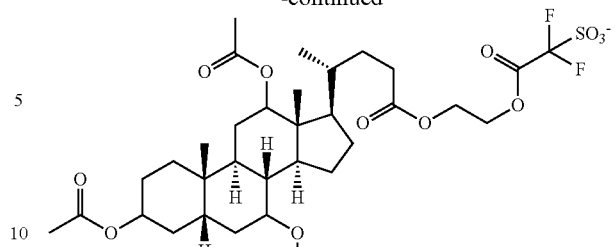
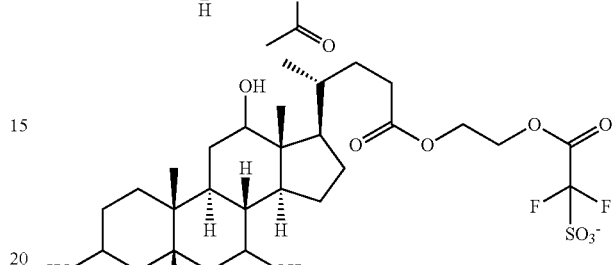
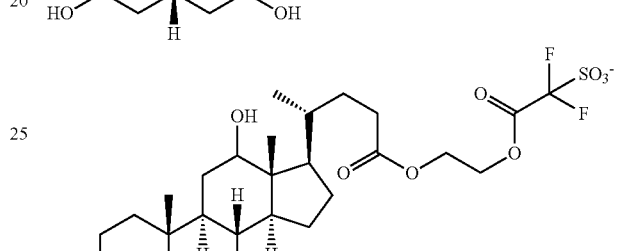
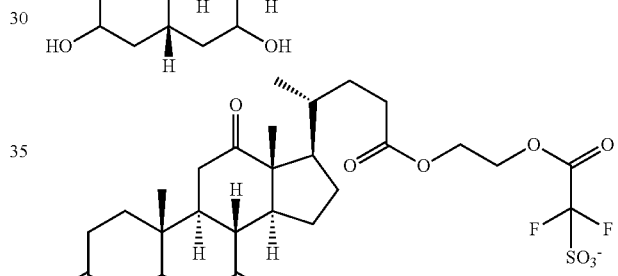
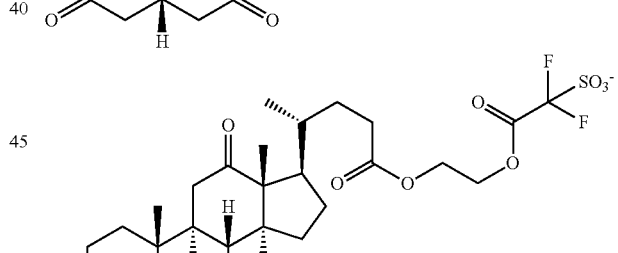
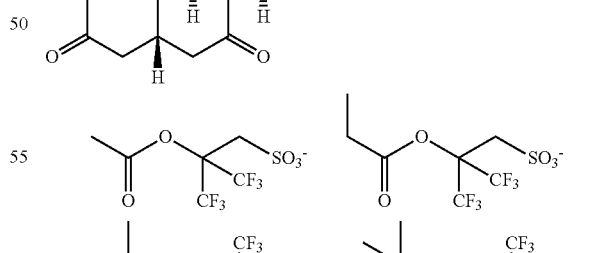
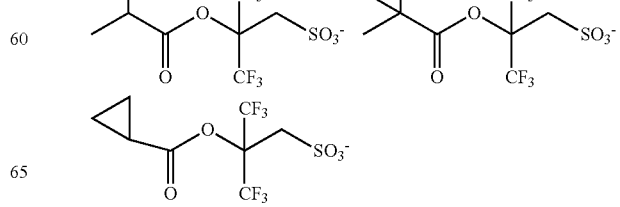

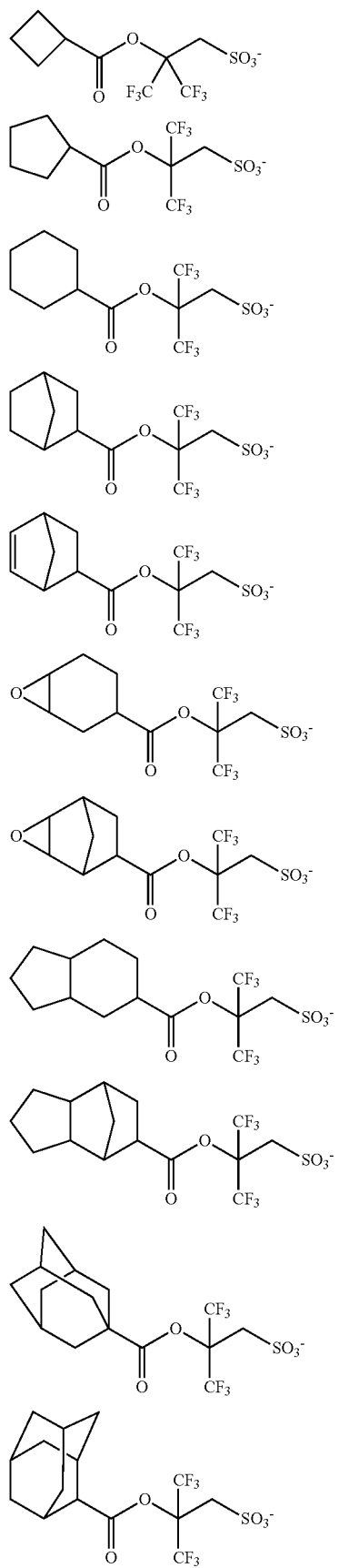
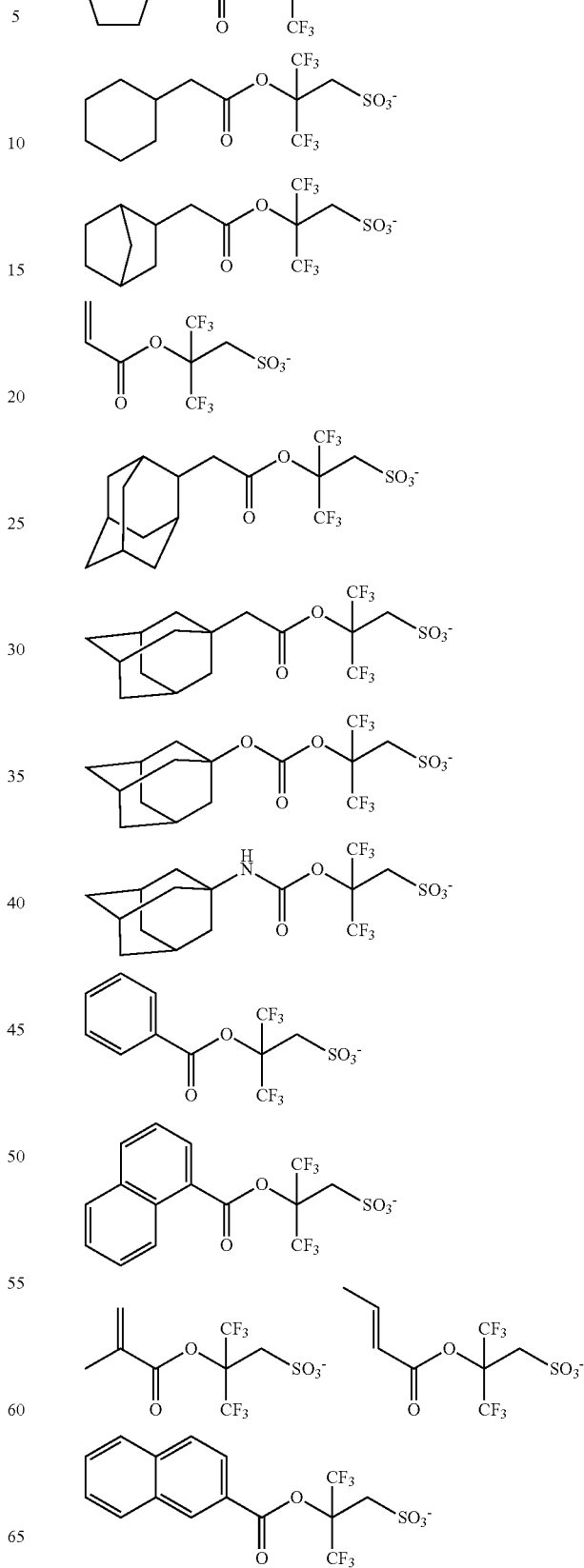

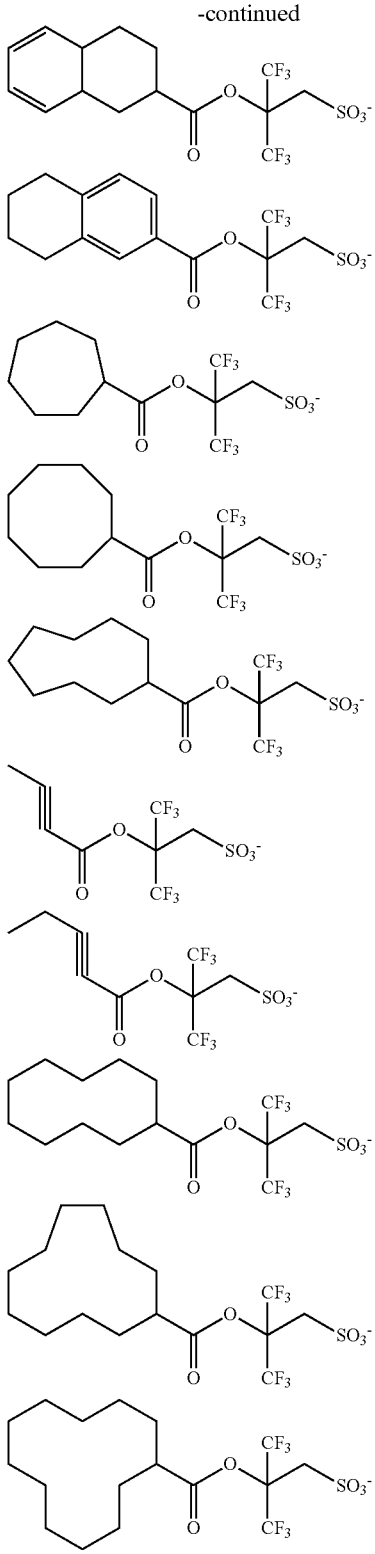

Among the foregoing anions, the ones having a polymerizable double bond or a hydroxy group are particularly preferable because they each react with the resin (base resin) and binds thereto when the adhesive composition is cured to remain in the living body contact layer even when it is wetted with water, not being extracted from the living body contact layer.

The salt shown by the foregoing general formula (1-1), (1-2), or (1-3) can be synthesized by a method of mixing an ammonium salt composed of the foregoing fluorosulfonate anion and an ammonium cation with sodium chloride, potassium chloride, or calcium chloride in organic solvent, for example. In this case, ammonium chloride formed as a bi-product is preferably removed by washing with water.

The amount of the salt to be blended as an electro-conductive material is preferably in a range of 0.1 to 200 parts by mass, more preferably in a range of 1 to 100 parts by mass on the basis of 100 parts by mass of the resin. The salt may be blended alone or in combination of two or more kinds.

It is to be noted that Japanese Unexamined Patent Application Publication (Kokai) No. 2008-039815 and Japanese Unexamined Patent Application Publication (Kokai) No. 2010-113209 describe part of the salts blended as an electro-conductive material in the inventive adhesive composition. However, these Patent Application Publication only describe the salt as a material of thermal-acid generator blended to a resist underlayer film material.

[Resin]

The resin to be blended to the inventive adhesive composition is a component to prevent elution of the foregoing electro-conductive material (salt) from a living body contact layer to retain the salt. The resin is preferably either or both of heat-curable (thermosetting) resin or photo-curable resin, particularly one or more resins selected from silicone resin, acrylic resin, and urethane resin.

The silicone resin include an addition-curable (addition reaction-curable) type and a radical curable (radical cross-linking reaction-curable) type. As the addition-curable type, it is possible to use one that contains diorganosiloxane having an alkenyl group(s), MQ resin having an $R^{20}_3SiO_{0.5}$ unit and an $SiO_2$ unit, organohydrogenpolysiloxane having plurality of SiH groups, platinum catalyst, an addition reaction inhibitor, and organic solvent, for example, described in Japanese Unexamined Patent Application Publication (Kokai) No. 2015-193803. As the radical curable type, it is possible to use one that contains diorganopolysiloxane with or without an alkenyl group, MQ resin having an $R^{20}_3SiO_{0.5}$ unit and an $SiO_2$ unit, organic peroxide, and organic solvent, for example, described in Japanese Unexamined Patent Application Publication (Kokai) No. 2015-193803. Herein, $R^{20}$ represents substituted or unsubstituted monovalent hydrocarbon group having 1 to 10 carbon atoms.

It is also possible to use a polysiloxane-resin integrated compound that is formed by condensation reaction of MQ resin and polysiloxane having silanol at the terminal or the side chain of the polymer. The MQ resin improves the tackiness by the addition thereof because it contains many silanol, but does not bind to polysiloxane in molecular level because it is not crosslinkable. The tackiness can be increased by integrating the polysiloxane and the MQ resin as described above.

The silicone resin may contain modified siloxane that has a group selected from an amino group, an oxirane group, an oxetane group, a polyether group, a hydroxy group, a carboxy group, a mercapto group, a methacryl group, an acryl group, a phenol group, a silanol group, a carboxylic anhydride group, an aryl group, an aralkyl group, an amide group, an ester group, and a lactone ring. The addition of modified siloxane improves dispersibility of the electro-conductive material (salt) in the silicone resin. The modified siloxane may be modified at any of the single terminal, the both terminal, or the side chain of the siloxane.

As the acrylic resin, it is possible to use one having hydrophilic (meth) acrylic ester and hydrophobic long chain (meth)acrylic ester as the repeating units described in Japanese Unexamined Patent Application Publication (Kokai) No. 2016-011338, for example. In some cases, it is also possible to copolymerize (meth)acrylic ester having a functional group or (meth)acrylic ester having a siloxane bond.

As the urethane resin, it is possible to use one having an urethane bond with a polyether bond, polyester bond, polycarbonate bond, or siloxane bond described in Japanese Unexamined Patent Application Publication (Kokai) No. 2016-065238, for example.

In the inventive adhesive composition, the resin preferably has high compatibility with the foregoing salt to prevent lowering of the electric conductivity due to elation of salt from the living body contact layer. In the inventive adhesive composition, the resin preferably has high adhesive properties to the electro-conductive base material to prevent delamination of the living body contact layer from the electro-conductive base material. In order to increase the compatibility of resin with the salt and the adhesive properties of resin to the electro-conductive base material, the use of resin with high polarity is effective. Illustrative examples of such resin include resin having one or more moieties selected from an ether bond, an ester bond, an amide bond, an imide bond, an urethane bond, a thiourethane bond, and a thiol group; as well as polyacrylic resin, polyamide resin, polyimide resin, polyurethane resin, and polythiourethane resin. On the other hand, the living body contact layer is in contact with a living body, thereby being susceptible to perspiration. Accordingly, in the inventive adhesive composition, the resin preferably has high repellency, and is hardly hydrolyzed. To make the resin be highly repellent and hardly hydrolyzed, the use of silicon-containing resin is effective.

The silicon atom-containing polyacrylic resin includes a polymer that has a silicone main chain and a polymer that has a silicon atom(s) on the side chain, each of which can be suitably used. As the polymer that has a silicone main chain, silsesquioxane or siloxane having a (meth)acrylpropyl group and so on can be used. In this case, an addition of a photoradical generator allows the (meth)acryl moiety to polymerize to cure.

As the silicon atom-containing polyamide resin, it is possible to suitable use polyamide silicone resins described in Japanese Unexamined Patent Application Publication (Kokai) No. 2011-079946 and U.S. Pat. No. 5,981,680, for example. Such a polyamide silicone resin can be synthesized by combining a silicone or non-silicone compound having amino groups at the both terminals and a non-silicone or silicone compound having carboxy groups at the both terminals.

It is also possible to use polyamic acid before cyclization thereof, which is obtained by reacting carboxylic anhydride and amine. The carboxy group of the polyamic acid may be crosslinked by using a crosslinking agent such as an epoxy type and an oxetane type. It is also possible to esterify the carboxy group with hydroxyethyl (meth)acrylate to perform photoradical crosslinking of the (meth)acrylate moiety.

As the silicon atom-containing polyimide resin, it is possible to suitably use polyimide silicone resins described in Japanese Unexamined Patent Application Publication (Kokai) No. 2002-332305, for example. Although polyimide resins have very high viscosity, it can be changed to have low viscosity by blending a (meth)acrylic monomer as a solvent and a crosslinking agent.

Illustrative examples of the silicon atom-containing polyurethane resin include polyurethane silicone resins. These polyurethane silicone resins can be crosslinked through urethane bond by blending a compound having isocyanate groups at the both terminals and a compound having a hydroxy group(s) at the terminal(s), followed by heating thereof. In this case, a silicon atom(s) (siloxane bond) have to be contained in either or both of the compound having isocyanate groups at the both terminals and the compound having a hydroxy group(s) at the terminal(s). Alternatively, an urethane (meth)acrylate monomer and polysiloxane can be blended and photo-crosslinked as described in Japanese Unexamined Patent Application Publication (Kokai) No. 2005-320418. It is also possible to photo-crosslink a polymer having both of a siloxane bond(s) and an urethane bond(s), with the terminal having a (meth)acrylate group(s).

The silicon atom-containing polythiourethane resin can be obtained by reacting a compound having a thiol group(s) and a compound having an isocyanate group(s), provided that either or them have to contain a silicon atom(s). It can also be photo-cured if (meth)acrylate groups are contained at the terminals.

The silicone resin improves the compatibility with the foregoing salt by adding modified siloxane that has a group selected from an amino group, an oxirane group, an oxetane group, a polyether group, a hydroxy group, a carboxy group, a mercapto group, a methacryl group, an acryl group, a phenol group, a silanol group, a carboxylic anhydride group, an aryl group, an aralkyl group, an amine group, an ester group, and a lactone ring in addition to the diorganosiloxane having an alkenyl group(s), MQ resin having an $R^{20}{}_3SiO_{0.5}$ unit and an $SiO_2$ unit, and organohydrogenpolysiloxane having plurality of SiH groups.

As will be described later, the living body contact layer is a cured material of the adhesive composition. Curing thereof improves the adhesion properties of the living body contact layer to both of skin and the electro-conductive base material. The curing means is not limited, and common means can be used, including crosslinking reaction by either or both of heat and light, an acid catalyst, or a base catalyst. The crosslinking reaction can be performed by appropriately selecting a crosslinking method described in "Kakyou hannou handbook (handbook of crosslinking reaction)", Yasuharu Nakamura, Maruzen shuppan (2013).

The diorganosiloxane having an alkenyl group(s) and organohydrogenpolysiloxane having plurality of SiH groups can be crosslinked through an addition reaction with a platinum catalyst.

Illustrative examples of the platinum catalyst include platinum-based catalysts such as platinic chloride, alcohol solution of platinic chloride, reaction product of platinic chloride and alcohol, reaction product of platinic chloride and an olefin compound, reaction product of platinic chloride and vinyl group-containing siloxane, a platinum-olefin complex, a complex of platinum and vinyl group-containing siloxane; platinum group metal-based catalysts such as a rhodium complex and a ruthenium complex. These catalysts may be used after dissolved or dispersed in alcohol solvent, hydrocarbon solvent, or siloxane solvent.

The amount of platinum catalyst is preferably in a range of 5 to 2,000 ppm, particularly in a range of 10 to 500 ppm on the basis of 100 parts by mass of the resin.

When the addition curable silicone resin is used, an addition reaction inhibitor may be added. This addition reaction inhibitor is added as a quencher to prevent the platinum catalyst from acting in the solvent or under a low temperature circumstance after forming the coating film and before heat curing. Illustrative examples thereof include 3-methyl-1-butyn-3-ol, 3-methyl-1-penthyn-3-ol, 3,5-dimethyl-1-hexyn-3-ol, 1-ethynylcyclohexanol, 3-methyl-3-trimethylsiloxy-1-butyne, 3-methyl-3-trimethylsiloxyl-3-penthyne, 3,5-dimethyl-3-trimethylsiloxy-1-hexyne, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, and 1,1,3,3-tetramethyl-1,3-divinyldisiloxane.

The amount of addition reaction inhibitor is preferably in a range of 0 to 10 parts by mass, particularly in a range of 0.05 to 3 parts by mass on the basis of 100 parts by mass of the resin.

Illustrative examples of photo-curing method include a method of adding a photoradical generator to generate radical by light, together with using resin having a (meth)acrylate terminal(s) or an olefin terminal(s) or adding a crosslinking agent with the terminal(s) being (meth)acrylate, olefin, or a thiol group(s); and a method of adding a photo-acid generator to generate acid by light, together with using resin or a crosslinking agent having an oxirane group(s), an oxetane group(s), or a vinyl ether group(s).

Illustrative examples of the photoradical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoic acid, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorchenzophenone, 2,2-diethoxyacetophenone, 2,2-dimethoxy-2-phenylacetophenone, 2,4-diethylthioxanthen-9-one, diphenyl(2,4,6-trimethylbenzoyl)phosphine oxide, 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone (BAPO).

The curing can also be performed by adding a radical generator of a heat decomposition type. Illustrative examples of the thermal radical generator include 2,2'-azobis(isobutyronitrile), 2,2'-azobis(2,4-dimethylvaleronitrile), 2,2'-azobis(2-methylbutyronitrile), 4,4'-azobis(4-cyanovaleric acid), 2,2'-azobis(methylpropionamidine) hydrochloride, 2,2'-azobis[2-(2-imidazolin-2-yl)propane] hydrochloride, 2,2'-azobis(4-methoxy-2,4-dimethylvaleronitrile), 2,2'-azobis(cyclohexane-1-carbonitrile), 1[(1-cyano-1-methylethyl)azo]formamide, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide), dimethyl-2,2'-azobis(isobutylate), 4,4'-azobis(4-cyanopentanoic acid), dimethyl-2,2'-azobis(2-methylpropionate), benzoyl peroxide, tert-butyl hydroperoxide, cumene hydroperoxide, di-tert-butyl peroxide, di-tert-amyl peroxide, di-n-butyl peroxide, dimethyl-2,2'-azobis(2-methylpropionate), and dicumyl peroxide.

Illustrative examples of the photo-acid generator include sulfonium salt, iodonium salt, sulfonyldiazomethane, N-sulfonyloxyimide, and oxime-O-sulfonate type acid generators. Specific examples of the photo-acid generator is described in paragraphs [0122] to [0142] of Japanese Unexamined Patent Application Publication (Kokai) No. 2008-111103 and Japanese Unexamined Patent Application Publication (Kokai) No. 2009-080474.

The amount of radical generator or photo-acid generator is preferably in a range of 0.1 to 50 parts by mass on the basis of 100 parts by mass of the resin.

[Tackifier]

The inventive adhesive composition may contain a tackifier in order to have tackiness to a living body. Illustrative examples of such a tackifier include silicone resin, as well as non-crosslinkable siloxane, non-crosslinkable poly(meth)acrylate, and non-crosslinkable polyether.

[Organic Solvent]

The inventive adhesive composition may contain organic solvent. Illustrative examples of the organic solvent include aromatic hydrocarbon solvent such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, 3,9-dodecadiyne, pentamethylbenzene, hexamethylbenzene, hexylbenzene, and 1,3,5-triethylbenzene; aliphatic hydrocarbon solvent such as n-heptane, isoheptane, 3-methylhexane, 2,3-dimethylpentane, 3-ethylpentane, 1,6-heptadiene, 5-methyl-1-hexyn, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-ectene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylneptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, dicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, isoparaffin; ketone solvent such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvent such as 3-methoxybutanol, 3-methyl-3-methoxybutanol, 1-methoxy-2-propanol, and 1-ethoxy-2-propanol; ether solvent such as propylene glycol monomethyl ether, ethylene glycol monomethyl ether, propylene glycol monoethyl ether, ethylene glycol monoethyl ether, propylene glycol dimethyl ether, diethylene glycol dimethyl ether, diisopropyl ether, diisobutyl ether, diisopentyl ether, di-n-pentyl ether, methyl cylopentyl ether, methyl cyclohexyl ether, di-n-butyl ether, di-sec-butyl ether, diisopentyl ether, di-sec-pentyl ether, di-tert-amyl ether, di-n-hexyl ether, and anisole; ester solvent such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate; lactone solvent such as γ-butyrolactone.

The amount of organic solvent is preferably in a range of 10 to 50,000 parts by mass on the basis of 100 parts by mass of the resin.

[Carbon Material]

The inventive adhesive composition can contain a carbon material as an electric conductivity improver to further enhance the electric conductivity. Illustrative examples of the carbon material include carbon black and carbon nanotube. The carbon nanotube may be either single layer or multilayer, and the surface may be modified with an organic group(s). The amount of carbon material is preferably in a range of 1 to 50 parts by mass on the basis of 100 parts by mass of the resin.

[Electric Conductivity Improver other than Carbon Material]

The inventive adhesive composition also can contain an electric conductivity improver other than the carbon material. Illustrative examples thereof include particles of resin coated with noble metal such as gold, silver, and platinum; nanoparticles of gold, silver, and platinum; as well as particles of metal oxide such as indium-tin oxide (ITO), indium-zinc oxide (IZO), tin oxide, and zinc oxide.

As described above, the inventive adhesive composition can form a living body contact layer for a bio-electrode that can efficiently conduct electric signals from skin to a device (i.e., having excellent electric conductivity), is free from the risk of causing allergies even when it is worn on skin for a long time (i.e., having excellent biocompatibility), is light in weight, can be manufactured at low cost, and does not cause large lowering of the electric conductivity even when it is wetted with water or dried. The elasticity and tackiness to skin can be improved by additives, and can be adjusted by adjusting the composition of the resin and the thickness of the living body contact layer appropriately.

<Bio-Electrode>

The present invention also provides a bio-electrode comprising an electro-conductive base material and a living body contact layer formed on the electro-conductive base material; wherein the living body contact layer is a cured material of the inventive adhesive composition described above.

Hereinafter, the inventive bio-electrode will be specifically described by reference to the FIGS., but the present invention is not limited thereto.

FIG. 1 is a schematic sectional view showing an example of the inventive bio-electrode. The bio-electrode 1 of FIG. 1 has the electro-conductive base material 2 and the living body contact layer 3 formed on the electro-conductive base material 2. The living body contact layer 3 is a layer in which the electro-conductive material (salt) 4 and the carbon material 5 are dispersed in the resin 6.

Figure 2:
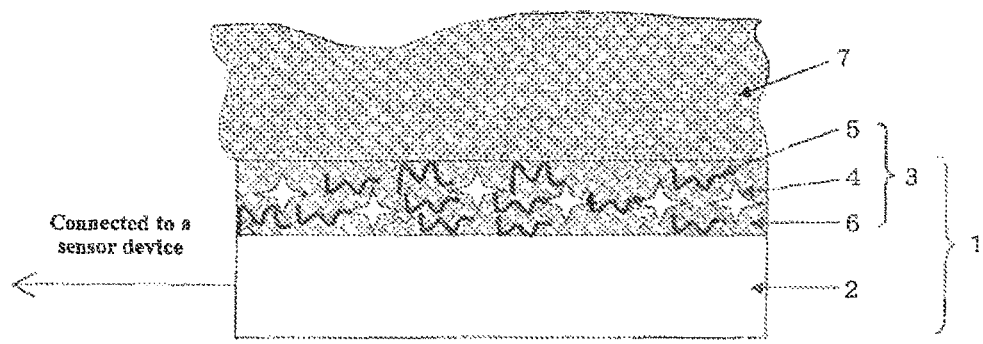
FIG. 2 is a schematic sectional view showing an example of the inventive bio-electrode worn on a living body.

When using the bio-electrode 1 of FIG. 1, electric signals are picked from the living body 7 through the salt 4 and the carbon material 5 while bringing the living body contact layer 3 (i.e., the layer in which the salt 4 and the carbon material 5 are dispersed in the resin 6) into contact win the living body 7, and then conducted to a sensor device (not shown) through the electro-conductive base material 2 as shown in FIG. 2. As described above, the inventive bio-electrode can cope with both electric conductivity and biocompatibility by using the salt described above, can improve the electric conductivity further by adding electric conductivity improver such as a carbon material in accordance with needs, and can obtain electric signals from skin stably in high sensitivity because the contact area with skin is kept constant due to the tackiness thereof.

Hereinafter, each component composing the inventive bio-electrode will be more specifically described.

[Electra-Conductive Base Material]

The inventive bio-electrode comprises an electro-conductive base material. This electro-conductive base material is usually connected electrically with a sensor device and so on, and conduct electrical signals picked from a living body through the living body contact layer to the sensor device and so on.

As the electro-conductive base material, any electro-conductive material can be used without being limited to particular ones. However, it is preferable to comprise one or more species selected from gold, silver, silver chloride, platinum, aluminum, magnesium, tin, tungsten, iron, copper, nickel, stainless steel, chromium, titanium, and carbon, for example.

The electro-conductive base material may be a hard electro-conductive substrate, an electro-conductive film having flexibility, a cloth with the surface being coated with electro-conductive paste, and a cloth into which electro-conductive polymer is kneaded without being limited to particular substrates. The electro-conductive substrate may be flat, uneven, or mesh-form of woven metal wires, which can be appropriately selected in accordance with the use of the bio-electrode.

[Living Body Contact Layer]

The inventive bio-electrode comprises a living body contact layer formed on the electro-conductive base material. This living body contact layer, which is a part to be actually in contact with a living body when using the bio-electrode, has electric conductivity and tackiness. The living body contact layer is a cured material of the inventive adhesive composition described above, that is to say, an adhesive resin layer that contains the resin and the electro-conductive material (salt) described above, together with additives such as a carbon material in accordance with needs.

The living body contact layer preferably has adhesion in a range of 0.5 N/25 mm or more and 20 N/25 mm or less. The adhesion is commonly measured by the method shown in JIS Z 0237, in which a metal substrate such as a stainless steel (SUS) substrate or a polyethylene terephthalate (PET) substrate can be used as a base material or, alternatively, human skin can be used for measuring. Human skin has lower surface energy compared to metals and various plastics, which energy is as low as that of Teflon (registered trade mark), and is hard to adhere.

The living body contact layer of the bio-electrode preferably has a thickness of 1 μm or more and 5 mm or less, more preferably 2 μm or more and 3 mm or less. A thinner living body contact layer has lower adhesion, but has improved flexibility and lighter weight to improve compatibility with skin. The thickness of the living body contact layer can be selected based on the balance of adhesion and texture.

The inventive bio-electrode may be provided with a tacky film separately on the living body contact layer as previous bio-electrodes (e.g., the bio-electrode described in Japanese Unexamined Patent Application Publication No. 2004-033468) in order to prevent peeling off of the bio-electrode from a living body during the use. When the tacky film is prepared separately, the tacky film may be formed by using a raw material for the tacky film such as an acrylic type, an urethane type, and a silicone type. Particularly, the silicone type is suitable because of the high transparency of oxygen, which enables breathing through the skin while pasting the same, the high water repellency, which decreases lowering of tackiness due to perspiration, and the low stimuli to skin. It is to be noted that the inventive bio-electrode does not necessarily require the tacky film that is prepared separately described above, because peeling off from a living body can be prevented by adding tackifier to the adhesive composition or using a resin having good tackiness to a living body as described above.

When the inventive bio-electrode is used as a wearable device, the components such as wiring between the bio-electrode and a sensor device may be any material without being limited to particular ones. For example, it is possible to apply the ones described in Japanese Unexamined Patent publication (Kokai) No. 2004-033468.

As described above, the inventive bio-electrode can efficiently conduct electric signals from skin to a device (i.e., having excellent electric conductivity), is free from the risk of causing allergies even when it is worn on skin for a long time (i.e., having excellent biocompatibility), is light in weight, can be manufactured at low cost, and does not cause large lowering of the electric conductivity even when it is wetted with water or dried, because the living body contact layer is formed from a cured material of the inventive adhesive composition described above. The elasticity and tackiness to skin can be improved by additives, and can be adjusted by adjusting the composition of the resin and the thickness of the living body contact layer appropriately. Accordingly, the inventive bio-electrode described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, comprising: applying the inventive adhesive composition described above onto the electro-conductive base material; and curing the adhesive composition; thereby forming the living body contact layer.

The same electro-conductive base material and adhesive composition as described above can be used for the inventive method for manufacturing a bio-electrode.

As the method for applying the adhesive composition onto the electro-conductive base material, any method can be used without being limited to particular ones; and dip coating, spray coating, spin coating, roll coating, flow coating, doctor coating, screen printing, flexographic printing, gravure printing, and inkjet printing are suitable.

The method for curing the resin can be appropriately selected based on a kind of resin used for the adhesive composition without being limited to particular methods. For example, the resin is preferably cured by either or both of heat and light. The foregoing adhesive composition can also be cured by adding a catalyst to generate acid or base, which causes a crosslinking reaction.

In case of heating, the temperature may be appropriately selected based on a kind of resin used for the adhesive composition without being limited to particular temperature. For example, it is preferable to be about 50 to 250° C.

When the heating and light irradiation are combined, it is possible to perform the heating and the light irradiation simultaneously, to perform the heating after the light irradiation, or to perform the light irradiation after the heating. It is also possible to perform air-drying to evaporate solvent before heating the coating film.

As described above, the inventive method for manufacturing a bio-electrode can manufacture the in bio-electrode easily and at low cost, which has excellent electric conductivity and biocompatibility as well as light weight without causing large lowering of the electric conductivity even when it is wetted with water or dried.

EXAMPLES

Hereinafter, the present invention will be specifically described by reference to Examples and Comparative Examples, but the present invention is not limited thereto. Incidentally, "Me" represents a methyl group, and "Vi" represents a vinyl group.

The following are Salts 1 to 16 and Comparative Salts 1 to 4 each blended to the adhesive composition solution as an electro-conductive material.

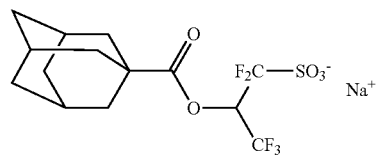

Salt 1

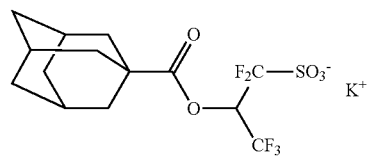

Salt 2

Salt 3
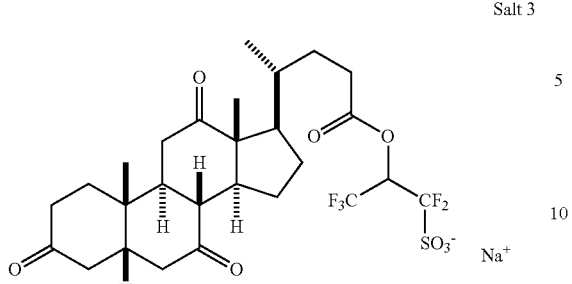
Na⁺
Salt 4
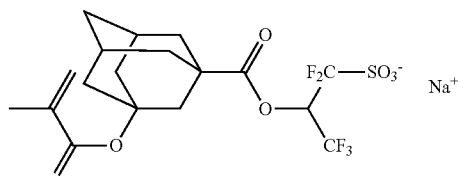
K⁺
Salt 5
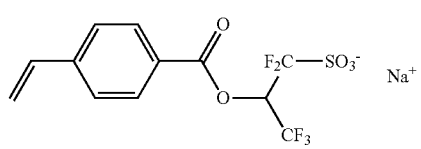
K⁺
Salt 6
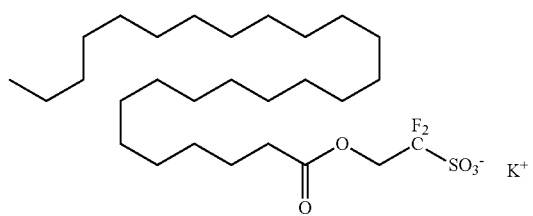
K⁺
Salt 7
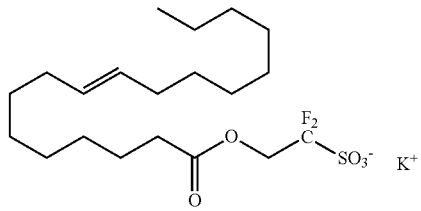
Ca²⁺
Salt 8
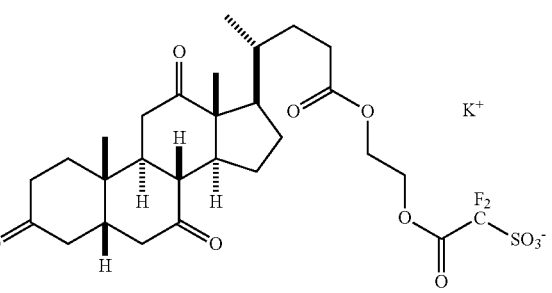
K⁺
Salt 9
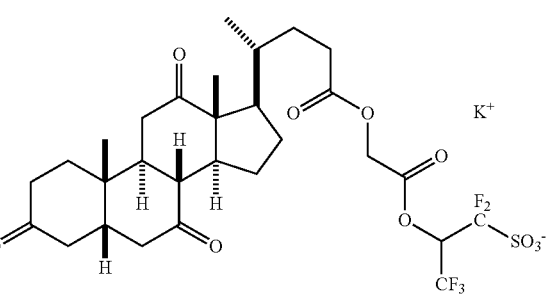
K⁺
Salt 10
Na⁺
Salt 11
Na⁺
Salt 12
K⁺
Salt 13
K⁺
Salt 14
K⁺
Salt 15
K⁺

Salt 16

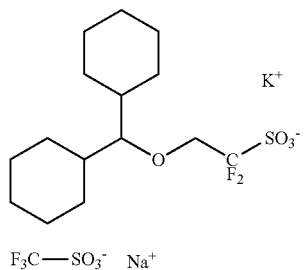

Comparative Salt 1

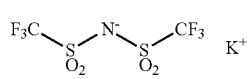

Comparative Salt 2

Comparative Salt 3

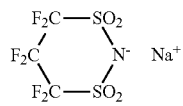

Comparative Salt 4

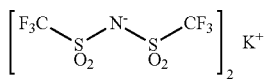

The following are Siloxane Compounds 1 to 3 each blended to the adhesive composition solution as silicone resin.
(Siloxane Compound 1)

Siloxane Compound 1 was vinyl group-containing polydimethylsiloxane having an alkenyl group-content of 0.007 mol/100 g in which the terminals of molecular chains were blocked with $SiMe_2Vi$ groups, with the 30% toluene solution having a viscosity or 27,000 mPa·s.
(Siloxane Compound 2)

Siloxane Compound 2 was a 60% toluene solution of polysiloxane of MQ resin composed of an $Me_3SiO_{0.5}$ unit and an $SiO_2$ unit ($Me_3SiO_{0.5}$ unit/$SiO_2$ unit=0.8).
(Siloxane Compound 3)

Siloxane Compound 3 was a polydimethylsiloxane-bonded MQ resin obtained by heating a solution composed of 40 parts by mass of vinyl group-containing polydimethylsiloxane having an alkenyl group-content of 0.007 mol/100 g in which the terminals of molecular chains were blocked with OH groups, with the 30% toluene solution having a viscosity of 42,000 mPa·s; 100 parts by mass of 60% toluene solution of polysiloxane of MQ resin composed of an $Me_3SiO_{0.5}$ unit and an $SiO_2$ unit ($Me_3SiO_{0.5}$ unit/$SiO_2$ unit=0.8); and 26.7 parts by mass of toluene with refluxing for 4 hours, followed by cooling.

As a silicone resin, KF-353 manufactured by Shin-Etsu Chemical Co., Ltd. was used, which is polyether type silicone oil with the side chain being modified with polyether.

The following is Acrylic polymer 1 blended to the adhesive composition solution as an acrylic type resin.

Acrylic polymer 1

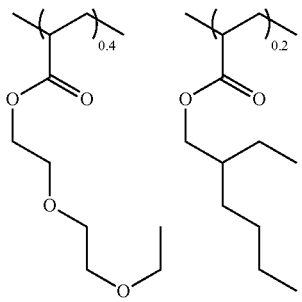

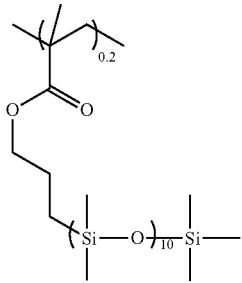

(the repeating number in the formula is an average value)
Acrylic Polymer 1:
  Molecular weight (Mw)=103,000
  Dispersity (Mw/Mn)=2.10

The following are Silicone urethane acrylate 1 and 2 as well as Silicone acrylate 1 to 3 each blended to the adhesive composition solution as a silicone type, an acrylic type, or an urethane type resin.

Silicone urethane acrylate 1

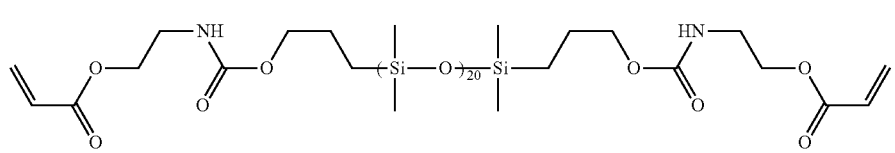

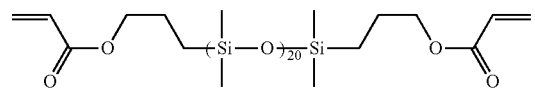
Silicone urethane acrylate 2

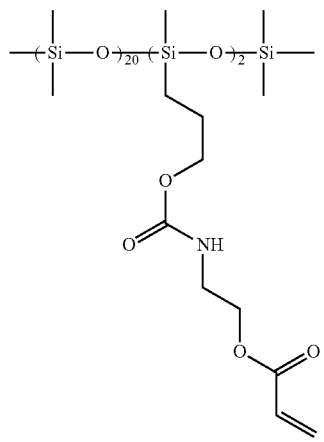

Silicone acrylate 1

Silicone acrylate 2

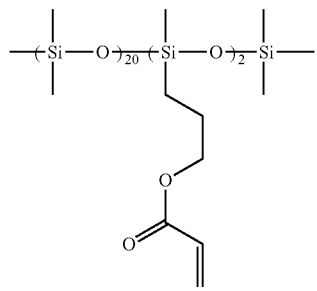

Silicone acrylate 3

(each repeating number in the formulae is an average value).

The following are organic solvents each blended to the adhesive composition solution.
PGMEA: propylene glycol-1-monomethyl ether-2-acetate
PGME: propylene glycol-1-monomethyl ether The following are a platinum catalyst, a radical generator, and electric conductivity improvers (carbon black, carbon nanotube, Au-coated particle, Ag-coated particle, and ITO particle) blended to The adhesive composition solution as an additive.
Platinum catalyst: CAT-PL-50T manufactured by Shin-Etsu Chemical Co., Ltd.
Radical generator: V-601 manufactured by Wako Pure Chemical industries, Ltd.
Carbon black: DENKA BLACK HS-100 manufactured by Denka Co., Ltd.
Carbon nanotube: carbon nanotube having a diameter of 0.7 to 1.1 nm and a length of 300 to 2,300 nm manufactured by Sigma-Aldrich Co. LLC.
Au-coated particle: Micropearl AU (the diameter of 3 μm) manufactured by SEKISUI CHEMICAL CO. LTD.
Ag-coated particle: Ag-coated powder (the diameter of 30 μm) manufactured by Mitsubishi Materials Electronic Chemicals Co., Ltd.
ITO particle: ITO powder (the diameter of 0.03 μm) manufactured by Mitsubishi Materials Electronic Chemicals Co., Ltd.

Examples 1 to 22, Comparative Examples 1 to 5

The electro-conductive material (salt), resin, organic solvent, and additives (a platinum catalyst, a radical generator, electric conductivity improver) were blended on the basis of the composition described in Tables 1 and 2 to prepare each adhesive composition solution (Adhesive composition solutions 1 to 22, Comparative Adhesive composition solutions 1 to 5).

TABLE 1

| Adhesive composition solutions | Electro-conductive materials (parts by mass) | Resin (parts by mass) | Organic solvent (parts by mass) | Additives (parts by mass) |
|---|---|---|---|---|
| Adhesive composition solution 1 | Salt 1 (10) | Siloxane compound 1 (40) Siloxane compound 2 (100) | toluene (30) PGME (14) | Platinum catalyst (1.0) Carbon black (10) |
| Adhesive composition solution 2 | Salt 2 (10) | Siloxane compound 3 (126) | heptane (30) PGME (14) | Platinum catalyst (1.0) Carbon black (10) |
| Adhesive composition solution 3 | Salt 3 (15.0) | Siloxane compound 1 (20) Siloxane compound 2 (100) Acrylic polymer 1 (20) | toluene (30) PGMEA (14) | Platinum catalyst (1.0) Carbon black (10) |
| Adhesive composition solution 4 | Salt 4 (8.4) | Siloxane compound 3 (126) | toluene (30) PGMEA (14) | Platinum catalyst (1.0) Carbon black (10) |
| Adhesive composition solution 5 | Salt 5 (9.6) | Siloxane compound 3 (126) | toluene (30) PGME (14) | Platinum catalyst (1.0) Carbon black (10) |

TABLE 1-continued

| Adhesive composition solutions | Electro-conductive materials (parts by mass) | Resin (parts by mass) | Organic solvent (parts by mass) | Additives (parts by mass) |
|---|---|---|---|---|
| Adhesive composition solution 6 | Salt 6 (13.4) | Siloxane compound 3 (100) KF-353 (26) | toluene (30) 2-heptanone (14) | Platinum catalyst (1.0) Carbon black (10) |
| Adhesive composition solution 7 | Salt 7 (7.8) | Siloxane compound 3 (126) | toluene (30) PGME (14) | Platinum catalyst (1.0) Carbon black (10) |
| Adhesive composition solution 8 | Salt 8 (10) | Siloxane compound 3 (126) | toluene (30) PGME (14) | Platinum catalyst (1.0) Carbon black (10) |
| Adhesive composition solution 9 | Salt 9 (13) | Siloxane compound 3 (126) | toluene (30) PGME (14) | Platinum catalyst (1.0) Carbon black (10) |
| Adhesive composition solution 10 | Salt 2 (10) | Siloxane compound 3 (126) | toluene (30) PGME (14) | Platinum catalyst (1.0) Carbon nanotube (2) |
| Adhesive composition solution 11 | Salt 2 (10) | Siloxane compound 3 (126) | toluene (30) PGME (14) | Radical generator (4) Au-coated particle (20) |
| Adhesive composition solution 12 | Salt 2 (10) | Siloxane compound 3 (126) | toluene (30) PGME (14) | Radical generator (4) Au-coated particle (20) |
| Adhesive composition solution 13 | Salt 2 (10) | Siloxane compound 3 (106) Silicone urethane acrylate 2 (20) | toluene (30) PGME (14) | Radical generator (4) ITO particle (20) |
| Adhesive composition solution 14 | Salt 1 (5) Salt 2 (5) | Siloxane compound 3 (106) Silicone acrylate 1 (20) | toluene (30) PGME (14) | Platinum catalyst (1.0) Radical generator (2.0) Carbon black (10) |
| Adhesive composition solution 15 | Salt 1 (4) Salt 2 (4) Salt 7 (2) | Siloxane compound 3 (106) Silicone acrylate 2 (20) | toluene (30) PGME (14) | Platinum catalyst (1.0) Radical generator (2.0) Carbon black (10) |
| Adhesive composition solution 16 | Salt 10 (20) | Siloxane compound 3 (106) Silicone acrylate 3 (20) | toluene (30) PGME (14) | Platinum catalyst (1.0) Radical generator (2.0) Carbon black (10) |
| Adhesive composition solution 17 | Salt 11 (20) | Siloxane compound 3 (106) Silicone urethane acrylate 1 (20) | toluene (30) PGME (14) | Platinum catalyst (1.0) Radical generator (2.0) Carbon black (10) |
| Adhesive composition solution 18 | Salt 12 (12.0) | Siloxane compound 3 (100) KF-353 (26) | toluene (30) 2-heptanone (14) | Platinum catalyst (1.0) Carbon black (10) |
| Adhesive composition solution 19 | Salt 13 (12.0) | Siloxane compound 3 (100) KF-353 (26) | toluene (30) 2-heptanone (14) | Platinum catalyst (1.0) Carbon black (10) |
| Adhesive composition solution 20 | Salt 14 (12.0) | Siloxane compound 3 (100) KF-353 (26) | toluene (30) 2-heptanone (14) | Platinum catalyst (1.0) Carbon black (10) |
| Adhesive composition solution 21 | Salt 15 (12.0) | Siloxane compound 3 (100) KF-353 (26) | toluene (30) 2-heptanone (14) | Platinum catalyst (1.0) Carbon black (10) |
| Adhesive composition solution 22 | Salt 16 (15.0) | Siloxane compound 3 (100) KF-353 (26) | toluene (30) 2-heptanone (14) | Platinum catalyst (1.0) Carbon black (10) |

TABLE 2

| Adhesive composition solutions | Electro-conductive materials (parts by mass) | Resin (parts by mass) | Organic solvent (parts by mass) | Additives (parts by mass) |
|---|---|---|---|---|
| Comparative Adhesive composition solution 1 | Comparative Salt 1 (4) | Siloxane compound 3 (126) | toluene (30) PGME (14) | Platinum catalyst (1.0) Carbon black (10) |
| Comparative Adhesive composition solution 2 | Comparative Salt 2 (7.4) | Siloxane compound 3 (126) | toluene (30) PGME (14) | Platinum catalyst (1.0) Carbon black (10) |
| Comparative Adhesive composition solution 3 | Comparative Salt 3 (7.4) | Siloxane compound 3 (126) | toluene (30) PGME (14) | Platinum catalyst (1.0) Carbon black (10) |
| Comparative Adhesive composition solution 4 | Comparative Salt 4 (14) | Siloxane compound 3 (126) | toluene (30) PGME (14) | Platinum catalyst (1.0) Carbon black (10) |
| Comparative Adhesive composition solution 5 | — | Siloxane compound 3 (126) | toluene (30) PGME (14) | Platinum catalyst (1.0) Carbon black (10) |

(Evaluation of Electric Conductivity)

Figure 3:
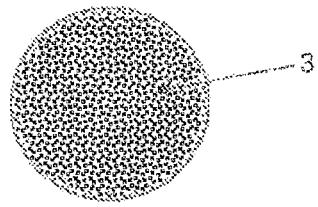
FIG. 3(a) is a schematic view of the bio-electrode produced in Examples of the present invention viewed from the living body contact layer side.
FIG. 3(b) is a schematic view of the bio-electrode produced in Examples of the present invention viewed from the electro-conductive base material side.
Figure 3:
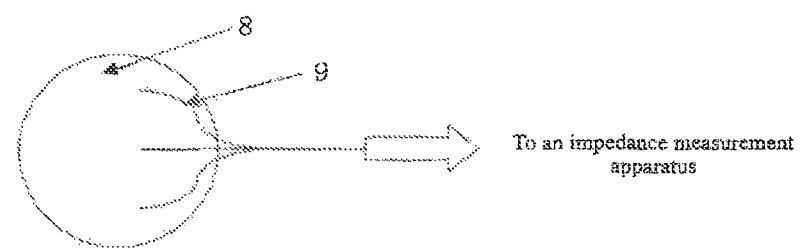
Figure 4:
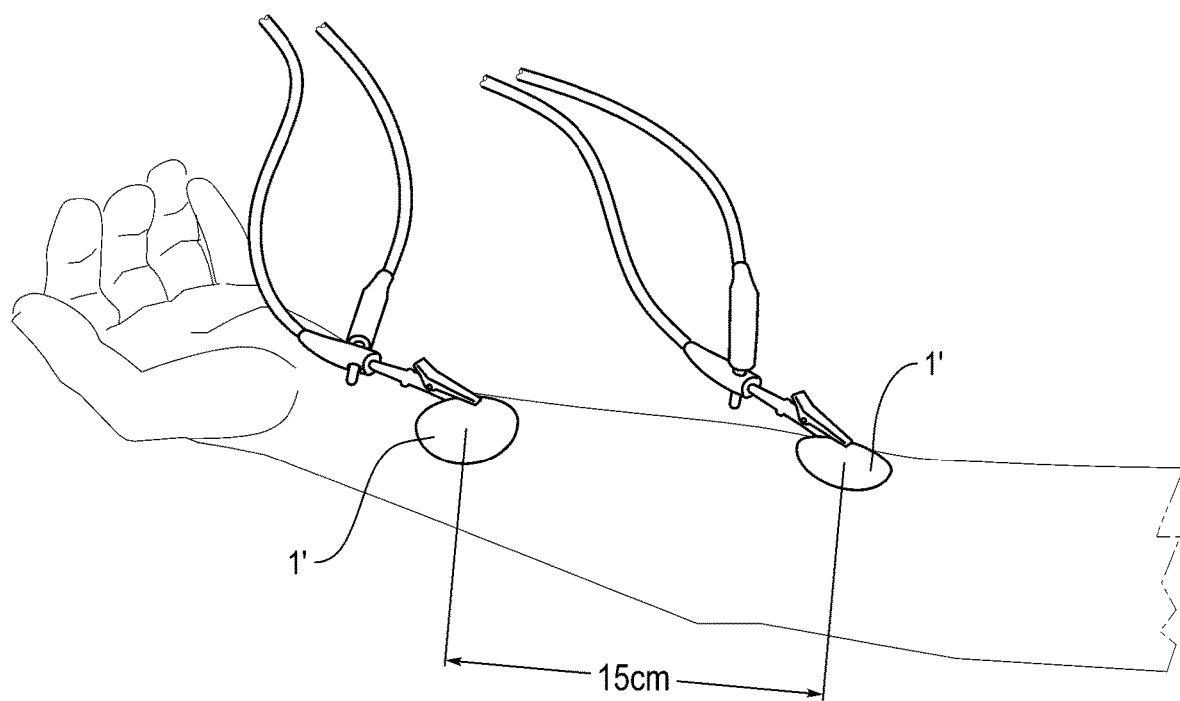
FIG. 4 is a schematic view of a scene of measuring impedance on the surface of skin by using the bio-electrode produced in Examples of the present invention.

Each adhesive composition solution was applied onto an aluminum disk having a diameter of 3 cm and a thickness of 0.2 mm by using an applicator. This was air dried at room temperature for 6 hours, followed by curing through baking at 100° C. for 30 minutes under a nitrogen atmosphere by using an oven to produce four pieces of bio-electrodes for each adhesive composition solution. Thus obtained bio-electrode was provided with the living body contact layer 3 at one side and provided with the aluminum disk 8 at the other side as an electro-conductive base material as shown in FIGS. 3(*a*) and (*b*). Then, the copper wiring 9 was pasted on the surface of the aluminum disk 8 with adhesive tape at the side that had not been coated with the living body contact layer to form a lead-out electrode, which was connected to an impedance measurement apparatus as shown in FIG. 3 (*b*). Two pieces of the bio-electrodes 1' were pasted on a human arm at a distance of 15 cm from each other such that the side of each living body contact layer was in contact with the skin as shown in FIG. 4. The initial impedance was measured while altering the frequency by using an AC impedance measurement apparatus SI1260 manufactured by Solartron. Then, the remained two pieces of the bio-electrodes were immersed in pure water for 1 hour, followed by drying the water, and used for measuring the impedance on skin by the same method described above. Each impedance at the frequency of 1,000 Hz are shown in Table 3.

(Evaluation of Tackiness: Measurement of Adhesion)

Each adhesive composition solution was applied onto a polyethylene naphthalate (PEN) substrate having a thickness of 100 μm by using an applicator. This was air dried at room temperature for 6 hours, followed by curing through baking at 100° C. for 30 minutes under a nitrogen atmosphere by using an oven to produce an adhesive film. From this adhesive film, a tape with a width of 25 mm was cut out. This was pressed to a stainless steel (SUS304) board and allowed to stand at room temperature for 20 hours. Then, the tape having adhesive mass attached thereon was pulled away from the stainless steel board to an angle of 180° at a speed of 300 mm/min by using a tensile tester to measure the force (N/25 mm) for peeling the tape. The results are shown in Table 3.

(Measurement of Thickness of Living Body Contact Layer)

On each bio-electrode produced in the evaluation test of electric conductivity described above, the thickness of the living body contact layer was measured by using a micrometer. The results are shown in Table 3.

As shown in Table 3, in each of Examples 1 to 22, the living body contact layer of which was formed by using the inventive adhesive composition containing the salt with particular structure, the initial impedance was low and did not largely increased by an order of magnitude after the bio-electrodes were immersed to water and dried. That is, Examples 1 to 22 each gave a bio-electrode that had high initial electric conductivity and did not cause large lowering of the electric conductivity even when it is wetted with water or dried. These bio-electrodes of Examples 1 to 22 had good adhesion similar to that of bio-electrode of Comparative Examples 1 to 4, in which previous salt was blended, were light in weight and excellent in biocompatibility, and could be manufactured at low cost.

On the other hand, in each Comparative Examples 1 to 4, the living body contact layer of which was formed by using an adhesive composition containing previous salt, the initial impedance was low, but large increase of the impedance occurred such that the order of magnitude was changed after water immersion and drying. That is, each of Comparative Examples 1 to 4 only gave a bio-electrode, the electric conductivity of which was largely decreased when it was wetted by water and dried, although the initial electric conductivity was high.

Comparative Example 5, in which the living body contact layer was formed by using an adhesive composition without containing salt, did not cause large increase of impedance by an order of magnitude after it was immersed to water and dried because it did not contain salt, but the initial impedance was high. That is, Comparative Example 5 only gave a bio-electrode with low initial electric conductivity.

As described above, it was revealed that bio-electrode, with the living body contact layer being formed by using the

TABLE 3

| | Adhesive composition solutions | Adhesion (N/25 mm) | Thickness of living body contact layer (μm) | Initial impedance ($\Omega$) | Impedance after water immersion ($\Omega$) |
|---|---|---|---|---|---|
| Example 1 | Adhesive composition solution 1 | 2.9 | 505 | $3.1\ E^3$ | $7.3\ E^3$ |
| Example 2 | Adhesive composition solution 2 | 2.8 | 555 | $2.8\ E^3$ | $3.1\ E^3$ |
| Example 3 | Adhesive composition solution 3 | 3.9 | 518 | $4.2\ E^3$ | $6.9\ E^3$ |
| Example 4 | Adhesive composition solution 4 | 2.3 | 470 | $3.8\ E^3$ | $5.2\ E^3$ |
| Example 5 | Adhesive composition solution 5 | 2.8 | 490 | $2.2\ E^3$ | $5.9\ E^3$ |
| Example 6 | Adhesive composition solution 6 | 3.2 | 460 | $1.9\ E^3$ | $3.8\ E^3$ |
| Example 7 | Adhesive composition solution 7 | 2.8 | 520 | $4.8\ E^3$ | $7.5\ E^3$ |
| Example 8 | Adhesive composition solution 8 | 2.5 | 430 | $4.6\ E^3$ | $7.4\ E^3$ |
| Example 9 | Adhesive composition solution 9 | 2.8 | 520 | $3.8\ E^3$ | $4.2\ E^3$ |
| Example 10 | Adhesive composition solution 10 | 2.6 | 450 | $3.2\ E^3$ | $5.5\ E^3$ |
| Example 11 | Adhesive composition solution 11 | 2.6 | 550 | $1.8\ E^3$ | $3.1\ E^3$ |
| Example 12 | Adhesive composition solution 12 | 3.1 | 540 | $1.7\ E^4$ | $3.2\ E^4$ |
| Example 13 | Adhesive composition solution 13 | 1.3 | 550 | $2.5\ E^4$ | $6.8\ E^4$ |
| Example 14 | Adhesive composition solution 14 | 1.8 | 533 | $1.8\ E^3$ | $3.4\ E^3$ |
| Example 15 | Adhesive composition solution 15 | 1.1 | 529 | $1.2\ E^3$ | $3.3\ E^3$ |
| Example 16 | Adhesive composition solution 16 | 1.8 | 555 | $4.8\ E^3$ | $5.4\ E^2$ |
| Example 17 | Adhesive composition solution 17 | 1.4 | 578 | $5.2\ E^3$ | $6.3\ E^2$ |
| Example 18 | Adhesive composition solution 18 | 2.0 | 510 | $1.4\ E^3$ | $2.8\ E^3$ |
| Example 19 | Adhesive composition solution 19 | 2.7 | 490 | $2.5\ E^3$ | $4.9\ E^3$ |
| Example 20 | Adhesive composition solution 20 | 1.2 | 440 | $5.5\ E^3$ | $6.9\ E^3$ |
| Example 21 | Adhesive composition solution 21 | 1.1 | 460 | $8.5\ E^3$ | $6.9\ E^3$ |
| Example 22 | Adhesive composition solution 22 | 2.1 | 390 | $2.5\ E^3$ | $7.9\ E^3$ |
| Comparative Example 1 | Comparative Adhesive composition solution 1 | 1.3 | 520 | $1.2\ E^4$ | $2.3\ E^6$ |
| Comparative Example 2 | Comparative Adhesive composition solution 2 | 2.1 | 530 | $1.2\ E^4$ | $6.3\ E^5$ |
| Comparative Example 3 | Comparative Adhesive composition solution 3 | 2.2 | 520 | $2.2\ E^4$ | $8.6\ E^5$ |
| Comparative Example 4 | Comparative Adhesive composition solution 4 | 2.1 | 530 | $2.6\ E^4$ | $6.3\ E^5$ |
| Comparative Example 5 | Comparative Adhesive composition solution 5 | 4.5 | 540 | $7.9\ E^5$ | $8.9\ E^5$ | inventive adhesive composition, had excellent electric conductivity, biocompatibility, and adhesion properties to an electro-conductive base material; without causing large lowering of electric conductivity even when it was wetted with water and dried because the electro-conductive material was held more securely; is light in weight, and can be manufactured at low cost.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. An adhesive composition comprising a resin and an electro-conductive material,
wherein the electro-conductive material is one or more salts selected from the group consisting of sodium salt, potassium salt, and calcium salt of fluorosulfonic acid having 5 or more carbon atoms shown by the following general formula (1),

$(R^1-X-Y-SO_3^-)_n \, M^{n+}$ (1)

wherein,
$R^1$ represents a linear, branched, or cyclic monovalent hydrocarbon group having 1 to 30 carbon atoms and optionally substituted by a heteroatom or optionally interposed by the heteroatom;
X represents any of a single bond, an ether group, an ester group, and an amide group;
Y represents a linear or branched alkylene group having 2 to 4 carbon atoms, containing 1 to 6 fluorine atoms, and optionally containing a carbonyl group;
$M^{n+}$ represents any of a sodium ion, a potassium ion, and a calcium ion; and
"n" is 1 when $M^{n+}$ is a sodium ion or a potassium ion, or is 2 when $M^{n+}$ is a calcium ion.

2. The adhesive composition according to claim 1, wherein the electro-conductive material is further defined by the following general formulae (1-1), (1-2), or (1-3),

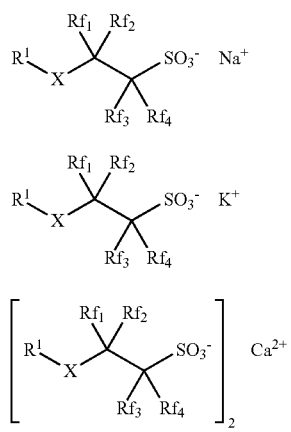

wherein,
each of the general formulae comprises $R^1$ and X;
$Rf_1$ to $Rf_4$ each independently represent an atom or a group selected from a hydrogen atom, a fluorine atom, a methyl group, an ethyl group, and a trifluoromethyl group, with the proviso that one or more of $Rf_1$ to $Rf_4$ is the fluorine atom or the trifluoromethyl group, and $Rf_1$ and $Rf_2$ are optionally combined with each other to form the carbonyl group.

3. The adhesive composition according to claim 1, wherein the electro-conductive material has a polymerizable double bond or a hydroxy group in the anion.

4. The adhesive composition according to claim 2, wherein the electro-conductive material has a polymerizable double bond or a hydroxy group in the anion.

5. The adhesive composition according to claim 1, wherein the resin is one or more resins selected from silicone resin, acrylic resin, and urethane resin.

6. The adhesive composition according to claim 2, wherein the resin is one or more resins selected from silicone resin, acrylic resin, and urethane resin.

7. The adhesive composition according to claim 1, further comprising a carbon material.

8. The adhesive composition according to claim 2, further comprising a carbon material.

9. The adhesive composition according to claim 7, wherein the carbon material is either or both of carbon black and carbon nanotube.

10. The adhesive composition according to claim 8, wherein the carbon material is either or both of carbon black and carbon nanotube.

11. A bio-electrode comprising an electro-conductive base material and a living body contact layer formed on the electro-conductive base material;
wherein the living body contact layer is a cured material of the adhesive composition according to claim 1.

12. A bio-electrode comprising an electro-conductive base material and a living body contact layer formed on the electro-conductive base material;
wherein the living body contact layer is a cured material of the adhesive composition according to claim 2.

13. A bio-electrode comprising an electro-conductive base material and a living body contact layer formed on the electro-conductive base material;
wherein the living body contact layer is a cured material of the adhesive composition according to claim 3.

14. A bio-electrode comprising an electro-conductive base material and a living body contact layer formed on the electro-conductive base material;
wherein the living body contact layer is a cured material of the adhesive composition according to claim 5.

15. The bio-electrode according to claim 11, wherein the electro-conductive base material comprises one or more species selected from gold, silver, silver chloride, platinum, aluminum, magnesium, tin, tungsten, iron, copper, nickel, stainless steel, chromium, titanium, and carbon.

16. A method for manufacturing a bio-electrode having an electro-conductive base material and a living body contact layer formed on the electro-conductive base material, comprising:
applying the adhesive composition according to claim 1 onto the electro-conductive base material; and curing the adhesive composition; thereby forming the living body contact layer.

17. A method for manufacturing a bio-electrode having an electro- conductive base material and a living body contact layer formed on the electro-conductive base material, comprising:
applying the adhesive composition according to claim 2 onto the electro-conductive base material; and curing the adhesive composition; thereby forming the living body contact layer.

18. A method for manufacturing a bio-electrode having an electro- conductive base material and a living body contact layer formed on the electro-conductive base material, comprising:
applying the adhesive composition according to claim 3 onto the electro-conductive base material; and curing the adhesive composition; thereby forming the living body contact layer.

19. A method for manufacturing a bio-electrode having an electro-conductive base material and a living body contact layer formed on the electro-conductive base material, comprising:
applying the adhesive composition according to claim 5 onto the electro-conductive base material; and curing the adhesive composition; thereby forming the living body contact layer.

20. The method for manufacturing a bio-electrode according to claim 16, wherein the electro-conductive base material comprises one or more species selected from gold, silver, silver chloride, platinum, aluminum, magnesium, tin, tungsten, iron, copper, nickel, stainless steel, chromium, titanium, and carbon.

* * * * *